United States Patent
Baba et al.

(10) Patent No.: US 9,985,214 B2
(45) Date of Patent: *May 29, 2018

(54) MONOAMINE COMPOUND, CHARGE TRANSPORT MATERIAL, COMPOSITION FOR CHARGE TRANSPORT FILM, ORGANIC ELECTROLUMINESCENT ELEMENT, ORGANIC EL DISPLAY, AND ORGANIC EL LIGHTING

(71) Applicant: Mitsubishi Chemical Corporation, Tokyo (JP)

(72) Inventors: Tatsushi Baba, Yokohama (JP); Koichiro Iida, Yokohama (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 743 days.

This patent is subject to a terminal disclaimer.

(21) Appl. No.: 14/334,262

(22) Filed: Jul. 17, 2014

(65) Prior Publication Data

US 2014/0330025 A1    Nov. 6, 2014

Related U.S. Application Data

(63) Continuation of application No. 13/405,938, filed on Feb. 27, 2012, now Pat. No. 8,828,558, which is a continuation of application No. PCT/JP2010/064531, filed on Aug. 26, 2010.

(30) Foreign Application Priority Data

Aug. 27, 2009   (JP) .................................. 2009-196782

(51) Int. Cl.
| | |
|---|---|
| *C07D 209/82* | (2006.01) |
| *H01L 51/00* | (2006.01) |
| *C07D 209/86* | (2006.01) |
| *C07D 403/14* | (2006.01) |
| *C07D 405/14* | (2006.01) |
| *C09K 11/06* | (2006.01) |
| *H05B 33/10* | (2006.01) |
| *H01L 51/50* | (2006.01) |

(52) U.S. Cl.
CPC ........ *H01L 51/0061* (2013.01); *C07D 209/86* (2013.01); *C07D 403/14* (2013.01); *C07D 405/14* (2013.01); *C09K 11/06* (2013.01); *H01L 51/006* (2013.01); *H01L 51/0052* (2013.01); *H01L 51/0059* (2013.01); *H01L 51/0072* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *H01L 51/0073* (2013.01); *H01L 51/0085* (2013.01); *H01L 51/5056* (2013.01); *H01L 51/5072* (2013.01); *Y10S 428/917* (2013.01)

(58) Field of Classification Search
None
See application file for complete search history.

(56) References Cited

U.S. PATENT DOCUMENTS

| | | | |
|---|---|---|---|
| 4,920,022 A * | 4/1990 | Sakakibara ........... | C07C 211/54 252/500 |
| 5,616,801 A | 4/1997 | Shimada et al. | |
| 8,395,143 B2 | 3/2013 | Lee et al. | |
| 8,828,558 B2 * | 9/2014 | Baba .................... | C07D 209/86 257/40 |

(Continued)

FOREIGN PATENT DOCUMENTS

| | | |
|---|---|---|
| CN | 1984874 A | 6/2007 |
| CN | 101228647 A | 7/2008 |

(Continued)

OTHER PUBLICATIONS

Notification of Reexamination dated Apr. 20, 2015 in Chinese Patent Application No. 201080018115.3 (with English language translation).
Observations by a third party issued Jul. 14, 2015 in European Patent Application No. 10811971.0.
Office Action dated Jul. 23, 2015 in European Patent Application No. 10 811 971.0.
Office Action dated Sep. 2, 2015 in Chinese Patent Application No. 201080018115.3 (with English language translation).
Third Party Observation issued May 13, 2016 in European Patent Application No. 10811971.0.
Korean Office Action dated Apr. 21, 2016 in Korean Patent Application No. 10-2012-7001894 (with English language translation).
Office Action dated Sep. 20, 2016 in European Patent Application No. 10 811 971.0

(Continued)

*Primary Examiner* — Jeffrey H Murray
(74) *Attorney, Agent, or Firm* — Oblon, McClelland, Maier & Neustadt, L.L.P.

(57) ABSTRACT

A monoamine compound characterized by being represented by the following general formula (1).

[Chem. 1]

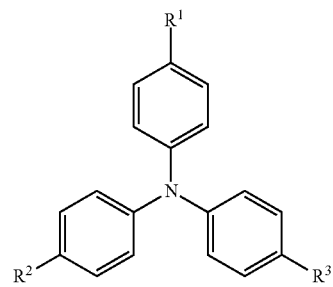

(1)

[In general formula (1), $R^1$ to $R^3$ each independently represent a phenyl group which may have a substituent in at least one of o- and m-positions, in which the substituent may be bonded to each other to form a cyclic structure. $R^1$ to $R^3$ are a group different from each other.]

18 Claims, 1 Drawing Sheet

(56) References Cited

U.S. PATENT DOCUMENTS

| | | | |
|---|---|---|---|
| 8,877,355 B2 * | 11/2014 | Yabe | C07C 211/54 257/40 |
| 2001/0008711 A1 | 7/2001 | Igarashi | |
| 2006/0217572 A1 | 9/2006 | Kawamura et al. | |
| 2007/0215889 A1 | 9/2007 | Kawakami et al. | |
| 2008/0014464 A1 | 1/2008 | Kawamura et al. | |
| 2008/0303417 A1 | 12/2008 | Yabunouchi et al. | |
| 2009/0066235 A1 | 3/2009 | Yabunouchi et al. | |
| 2009/0160323 A1 | 6/2009 | Nomura et al. | |
| 2009/0230846 A1 † | 9/2009 | Yabe | |
| 2010/0001636 A1 † | 1/2010 | Yabunouchi | |
| 2010/0244008 A1 | 9/2010 | Lee et al. | |
| 2011/0095269 A1 | 4/2011 | Zhang et al. | |
| 2011/0127495 A1 | 6/2011 | Hong et al. | |
| 2012/0065432 A1 | 3/2012 | Johansson et al. | |
| 2012/0074395 A1 | 3/2012 | Yabunouchi et al. | |
| 2012/0161119 A1 | 6/2012 | Yabunouchi | |
| 2012/0248426 A1 | 10/2012 | Kato | |
| 2013/0214263 A1 | 8/2013 | Yabe et al. | |
| 2014/0061630 A1 | 3/2014 | Yabunouchi | |
| 2014/0361285 A1 | 12/2014 | Yabe et al. | |
| 2016/0020403 A1 | 1/2016 | Kawamura et al. | |

FOREIGN PATENT DOCUMENTS

| | | | | |
|---|---|---|---|---|
| CN | 101473464 A | | 7/2009 | |
| EP | 1834945 | | 9/2007 | |
| EP | 1885008 | | 2/2008 | |
| EP | 2 031 670 A1 | | 3/2009 | |
| EP | 2 295 421 A1 | | 3/2011 | |
| JP | 01281453 | * | 11/1989 | ............. C09B 57/00 |
| JP | 11-273859 | | 10/1999 | |
| JP | 2006352088 A | † | 12/2006 | |
| JP | 2007-67383 | | 3/2007 | |
| JP | 2007-91719 | | 4/2007 | |
| JP | 2007-110093 | | 4/2007 | |
| JP | 2007-284431 | | 11/2007 | |
| JP | 2008-31068 | | 2/2008 | |
| JP | 2008-112984 | | 5/2008 | |
| JP | 2009-021335 | | 1/2009 | |
| JP | 2009-141336 | | 6/2009 | |
| JP | 2009-141339 | | 6/2009 | |
| JP | 2009-170817 A | | 7/2009 | |
| KR | 10-2008-0014016 A | | 2/2008 | |
| KR | 10-2011-0011647 A | | 2/2011 | |
| KR | 10-2012-0022859 A | | 3/2012 | |
| TW | 200927730 A | | 7/2009 | |
| WO | WO 2006/123667 A1 | | 11/2006 | |
| WO | WO 2009/061145 A1 | | 5/2009 | |
| WO | WO 2009/067419 | | 5/2009 | |
| WO | WO 2009/072587 A1 | | 6/2009 | |
| WO | 2009145016 A1 † | | 12/2009 | |
| WO | WO 2009/145016 A1 | | 12/2009 | |
| WO | 2010114017 A1 † | | 10/2010 | |
| WO | WO 2010/114017 | | 10/2010 | |

OTHER PUBLICATIONS

Extended European Search Report dated Nov. 8, 2016 in Patent Application No. 16183736.4.
Office Action dated Oct. 6, 2014 in European Patent Application No. 10 811 971.0.
Office Action dated Sep. 2, 2014 in Japanese Patent Application No. 2010-189102 (with English translation).
Chinese Office Action dated Aug. 6, 2014 in Patent Application No. 201080018115.3 (with English Translation).
International Search Report dated Nov. 22, 2010 in PCTJP2010/064531.
Tadahiro Echigo, et al., "Sprayed Organic Electrophosphorescent Devices with Small Organic Molecules", Japanese Journal of Applied Physics, vol. 44, No. IB, 2005, pp. 626-629.
Office Action dated Mar. 5, 2013 in Chinese Patent Application No. 201080018115.3 (w/English translation).
Combined Taiwanese Office Action and Search Report dated Jan. 6, 2014 in Patent Application No. 099128805 (with English language translation).
Combined Chinese Office Action and Search Report dated Sep. 30, 2013 in Chinese Patent Application No. 2010800118115.3 with English translation and English translation of category of cited documents.
Translation for JP 2009-021335 (publication date Jan. 2009).
Machine-generated translation for JP 2007-110093 A (publication date Apr. 2007) (printed as Part1 and Part 2).
Office Action dated Jul. 29, 2013 in EP Patent Application No. 10811971.0 filed Aug. 26, 2010.
Office Action dated Feb. 20, 2017 in Korean Patent Application No. 10-2012-7001894 (with English language translation).
Combined Chinese Office Action and Search Report dated Jun. 2, 2017 in Patent Application No. 201510870317.5 (with English language translation and English translation of categories of cited documents).
Office Action dated Dec. 18, 2017 in Korean Patent Application No. 10-2017-7025416 (w/ Computer-generated English translation).
Office Action dated Dec. 15, 2017 in Korean Patent Application No. 10-2017-7025414 (w/ Computer-generated English translation).
Office Action dated Jan. 9, 2018 in Chinese Patent Application No. 201510870317.5 (w/ English translation).
Office Action dated Mar. 21, 2018 in European Patent Application No. 16 183 736.4.

* cited by examiner
† cited by third party

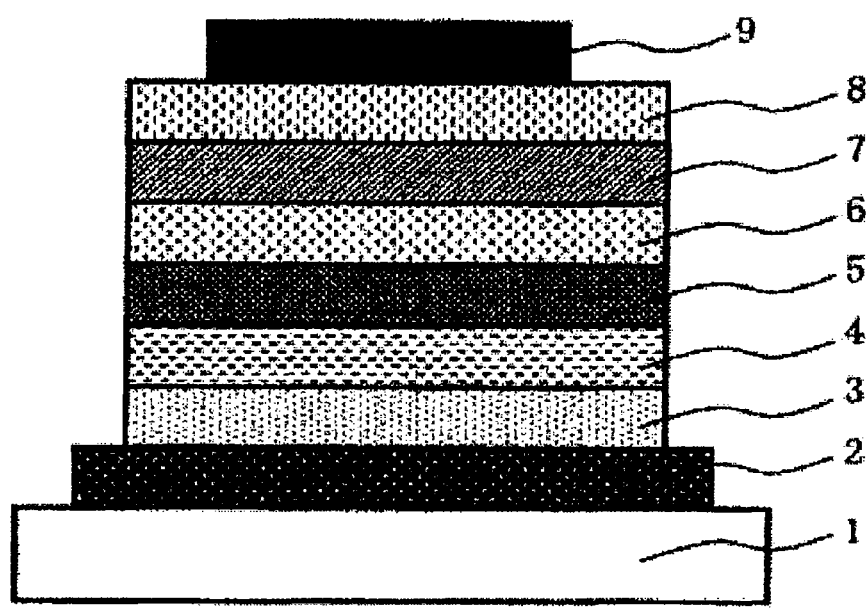

MONOAMINE COMPOUND, CHARGE TRANSPORT MATERIAL, COMPOSITION FOR CHARGE TRANSPORT FILM, ORGANIC ELECTROLUMINESCENT ELEMENT, ORGANIC EL DISPLAY, AND ORGANIC EL LIGHTING

CROSS REFERENCE TO RELATED APPLICATIONS

The present application is a continuation of U.S. patent application Ser. No. 13/405,938 filed Feb. 27, 2012, now allowed, which is a 35 U.S.C. § 371 national stage continuation application of International Patent Application No. PCT/JP10/64531 filed Aug. 26, 2010, which claims priority to Japanese Patent Application No. 2009-196782 filed Aug. 27, 2009, the contents of which are incorporated herein by reference in their entireties.

TECHNICAL FIELD

The present invention relates to a monoamine compound which is thermally and electrochemically stable and is soluble in various solvents, a charge transport material including the monoamine compound, a composition for charge transport film which contains the charge transport material, an organic electroluminescent element which includes a layer containing the charge transport material and has high luminescent efficiency and high driving stability, and an organic EL display and an organic EL lighting each equipped with the element.

BACKGROUND ART

In recent years, electroluminescent elements employing an organic thin film (organic electroluminescent elements) are being developed. Examples of methods for forming an organic thin film include a vacuum deposition method and a wet film formation method. Of these, the wet film formation method has advantages, for example, that no vacuum process is necessary and film formation in a larger area is easy, and that it is easy to incorporate a mixture of a plurality of materials having various functions into one layer (coating fluid).

Mainly used as the materials of luminescent layers formed by a wet film formation method are high-molecular materials such as poly(p-phenylenevinylene) derivatives and polyfluorene derivatives. However, high-molecular materials have problems including the following: (1) it is difficult to regulate the degree of polymerization and molecular weight distribution of the high-molecular materials, (2) deterioration due to residual end groups occurs during continuous drivings, and (3) it is difficult to highly purify the materials themselves and the materials contain impurities.

Due to those problems, the organic electroluminescent elements produced by a wet film formation method have poorer driving stability than organic electroluminescent elements produced by a vacuum deposition method, and have not reached a practical level at present, except some elements.

In patent document 1 is described an organic electroluminescent element employing an organic thin film formed by a wet film formation method from not a high-molecular compound but a mixture of a plurality of low-molecular materials (charge transport materials or luminescent materials) in an attempt to overcome those problems. As charge transport materials having the property of transporting holes, compounds H-1 and H-2 shown below are used therein.

[Chem. 1]

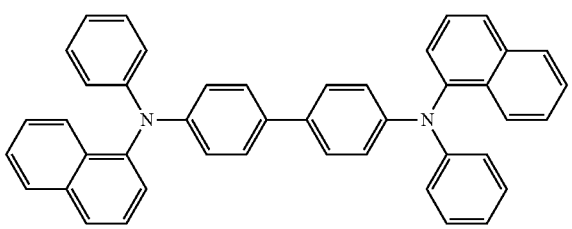

H-1

[Chem. 2]

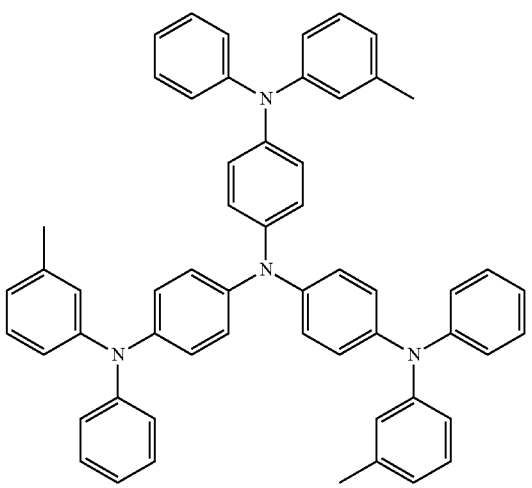

H-2

Meanwhile, with respect to organic electroluminescent elements employing an organic thin film which contains a plurality of low-molecular materials and has been formed by a wet film formation method, non-patent document 1 and patent document 2 describe an organic electroluminescent element which utilizes phosphorescence so as to have enhanced luminescent efficiency. Compounds H-3, H-4, and H-5 shown below are used as charge transport materials therein.

[Chem. 3]

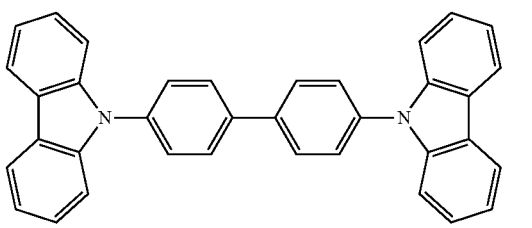

H-3

[Chem. 4]

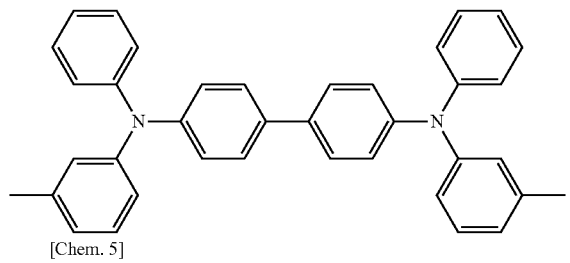

H-4

[Chem. 5]

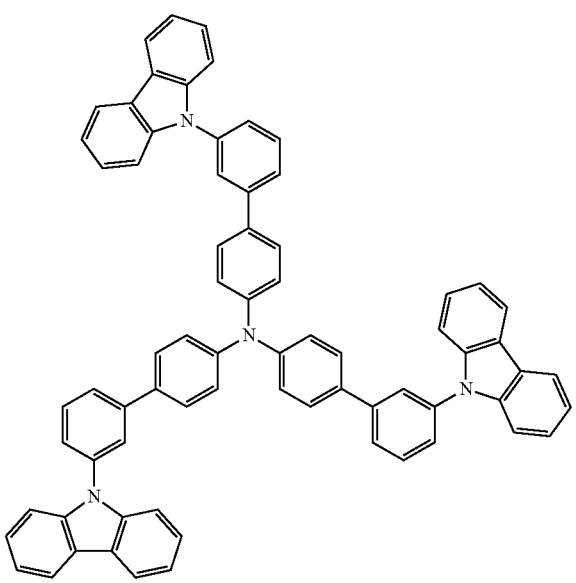

H-5

CONVENTIONAL-ART DOCUMENTS

Patent Documents

Patent Document 1: JP-A-11-273859
Patent Document 2: JP-A-2007-110093

Non-Patent Document

Non-Patent Document 1: *Japanese Journal of Applied Physics*, Vol. 44, No. 1B, pp. 626-629, 2005

SUMMARY OF THE INVENTION

Problems that the Invention is to Solve

However, the compounds H-1, H-2, H-3, H-4, and H-5 do not always have sufficient solubility in solvents. Although it is therefore necessary to use a halogenated solvent, e.g., chloroform, as a coating-fluid solvent, such halogenated solvents impose a heavy environmental burden. Furthermore, there is a possibility that impurities contained in the halogenated solvent might deteriorate the materials. It is thought that organic electroluminescent elements produced by a wet film formation method using a halogenated solvent do not have sufficient driving stability.

In addition, the compounds H-1, H-2, H-3, and H-4 have a low glass transition temperature and, hence, it is thought that the organic electroluminescent elements disclosed in patent document 1 and non-patent document 1 have room for improvement in heat resistance. Moreover, the compounds H-1, H-2, H-3, H-4, and H-5 are exceedingly apt to crystallize, and it is not easy to obtain an even amorphous film therefrom by a wet film formation method.

Furthermore, in the case where a phosphorescent material is used as a luminescent material, an organic electroluminescent element formed using a composition containing the compound H-1 and the phosphorescent material is thought to have low luminescent efficiency because the compound H-1 has a low triplet excitation level.

Consequently, the invention has been achieved in view of the state of the conventional-art techniques, and a subject for the invention is to provide a charge transport material which is thermally and electrochemically stable and is soluble in solvents and a composition for charge transport film which contains the charge transport material.

Another object of the invention is to provide an organic electroluminescent element having high luminescent efficiency and high driving stability and an organic EL display and an organic EL lighting which each are equipped with the element.

Means for Solving the Problems

The present inventors diligently made investigations. As a result, the inventors have found that a monoamine compound represented by the following general formula (1) has excellent solubility in solvents, is highly noncrystalline, can hence be formed into a thin film by a wet film formation method, and further has excellent charge-transporting properties, excellent durability concerning electrical oxidation/reduction, and a high triplet excitation level, and that use of the monoamine compound in an organic electroluminescent element can hence impart high luminescent efficiency and high driving stability thereto. The invention has been thus completed.

Namely, essential points of the invention reside in the following 1 to 11.

1. A monoamine compound characterized by being represented by the following general formula (1).

[Chem. 6]

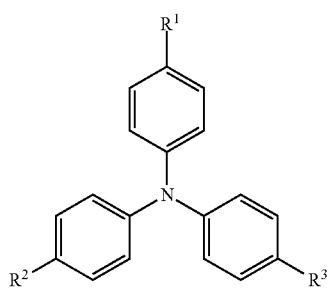

(1)

[In general formula (1), $R^1$ to $R^3$ each independently represent a phenyl group which may have a substituent in at least one of o- and m-positions, in which the substituent may be bonded to each other to form a cyclic structure, and $R^1$ to $R^3$ is a group different from each other.]

2. The monoamine compound according to 1 above, which further comprises a partial structure represented by the following structural formula (2-1).

[Chem. 7]

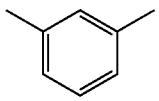

(2-1)

[In structural formula (2-1), the phenyl group may further have a substituent, in which the substituent may have been bonded to each other to form a cyclic structure.]

3. The monoamine compound according to 1 or 2 above, wherein in the general formula (1), $R^1$ to $R^3$ each independently are a phenyl group which may have a substituent in an m-position.

4. The monoamine compound according to any one of 1 to 3 above, wherein in the general formula (1), at least one of $R^1$ to $R^3$ is a group including a partial structure represented by the following general formula (2-2).

[Chem. 8]

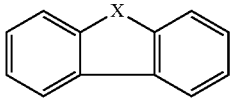

(2-2)

[X in general formula (2-2) represents any one of —NR⁴— (where $R^4$ represents an aryl group which may have a substituent), —O—, and —S—. The X-containing fused ring in general formula (2-2) may further have a substituent, in which the substituent may have been bonded to each other to form a cyclic structure.]

5. The monoamine compound according to 4 above, wherein the partial structure represented by general formula (2-2) is a partial structure represented by the following structural formula (3).

[Chem. 9]

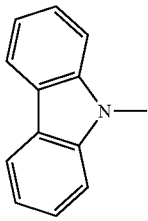

(3)

[In structural formula (3), the N-carbazole ring may further have a substituent, and the substituent may have been bonded to each other to form a cyclic structure.]

6. The monoamine compound according to any one of 1 to 5 above, wherein in the general formula (1), at least one of $R^1$ to $R^3$ is a group represented by the following general formula (11).

[Chem. 10]

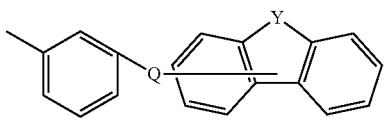

(11)

[In general formula (11), Q represents a direct bond or any linking group. Y has the same meaning as the X contained in the general formula (2-2). The Y-containing fused ring in general formula (11) may have a substituent, and the substituent may be bonded to each other to form a cyclic structure.]

7. The monoamine compound according to any one of 1 to 6 above, which has a solubility in m-xylene of 5% by mass or more at 25° C. and atmospheric pressure.

8. A charge transport material comprising the monoamine compound according to any one of 1 to 7 above.

9. A composition for charge transport film, which comprises the charge transport material according to 8 above and a solvent.

10. An organic electroluminescent element which comprises a substrate and, disposed thereover, an anode, a cathode, and a luminescent layer interposed between the electrodes, wherein the luminescent layer contains the charge transport material according to 8 above.

11. An organic EL display comprising the organic electroluminescent element according to 10 above.

12. An organic EL lighting comprising the organic electroluminescent element according to 10 above.

Effects of the Invention

According to the monoamine compound of the invention, the charge transport material including the monoamine compound, and the composition for charge transport film which contains the charge transport material, it is possible to easily form, by a wet film formation method, an organic thin film containing a material which is thermally and electrochemically stable and has a high triplet excitation level, and this facilitates production of an organic electroluminescent element having a larger area.

Furthermore, the organic electroluminescent element obtained using the charge transport material of the invention and using the composition for charge transport film which contains the charge transport material can be made to luminesce at a high luminance and high efficiency and has improved stability, in particular, improved driving stability.

Since the charge transport material of the invention has excellent film-forming properties, charge-transporting properties, luminescent characteristics, and heat resistance, the charge transport material can be applied to not only film formation by a vacuum deposition method but also film formation by a wet film formation method.

Moreover, since the charge transport material of the invention and the composition for charge transport film which contains the charge transport material have excellent film-forming properties, charge-transporting properties, luminescent characteristics, and heat resistance, the material and the composition can be applied to the formation of organic layers such as a hole injection layer, hole transport layer, luminescent layer, electron injection layer, and electron transport layer according to the layer configuration of the element.

Consequently, the organic electroluminescent element obtained using the charge transport material of the invention and using the composition for charge transport film which contains the charge transport material is thought to be applied to flat panel displays (e.g., displays for OA computers and wall-mounted TV receivers), vehicle-mounted display elements, cell phone displays, light sources taking advantage of the feature of a surface light emitter (e.g., the light source of a copier and the backlights of a liquid-crystal display and instrument), display panels, and marker lights, and have a high technical value.

Furthermore, the charge transport material of the invention and the composition for charge transport film which contains the charge transport material can be effectively utilized not only in organic electroluminescent elements but also in electrophotographic photoreceptors and the like because the material and the composition essentially have excellent stability to oxidation and reduction.

BRIEF DESCRIPTION OF THE DRAWING

FIG. 1 is a sectional view diagrammatically illustrating an example of the structure of an organic electroluminescent element of the invention.

MODES FOR CARRYING OUT THE INVENTION

Modes for carrying out the invention will be explained below in detail. However, the following explanations on constituent elements are for embodiments (representative embodiments) of the invention, and the invention should not be construed as being limited to the embodiments unless the invention departs from the spirit thereof.

<Monoamine Compound>

The monoamine compound of the invention (hereinafter referred to also as "compound (1)") is characterized by being represented by the following general formula (1).

[Chem. 11]

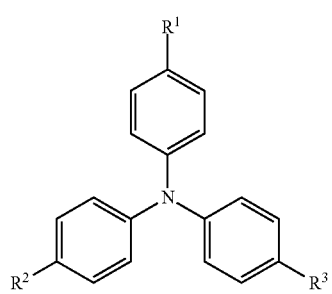

(1)

In general formula (1), $R^1$ to $R^3$ each independently represent a phenyl group which may have a substituent in at least one of o- and m-positions, and the substituents may be bonded to each other to form a cyclic structure. $R^1$ to $R^3$ are groups different from each other.

[1. Structural Features]

Since compound (1) has a triphenylamine structure, this compound has the excellent ability to transport charges (holes) and has a high triplet excitation level and high heat resistance.

$R^1$ to $R^3$ in compound (1), i.e., the three substituents possessed by the triphenylamine structure, differ from each other, and compound (1) hence has no axis of symmetry. Consequently, compound (1) is exceedingly highly noncrystalline, has excellent solubility in various organic solvents, and can form an organic thin film which is amorphous and does not crystallize readily.

Furthermore, since $R^1$ to $R^3$ each independently are a phenyl group which may have a substituent in at least one of o- and m-positions (hereinafter, such structure is sometimes referred to as "non-p-position-substituted partial structure"), compound (I) has further improved noncrystalline properties and better solubility.

In addition, the non-p-position-substituted partial structure has such properties that $R^1$ to $R^3$ are less apt to receive an electron as compared with phenyl groups having a substituent in the p-position. It is thought that compound (1), which contains the partial structure, is hence less apt to be decomposed (namely, the compound is electrochemically stable) and this leads to prevention of a decrease in the working life of organic electroluminescent elements.

From the standpoint of further improving the solubility, it is preferred that $R^1$ to $R^3$ should each independently be a phenyl group which may have a substituent in an m-position.

[2. Range of Molecular Weight]

The molecular weight of compound (1) is generally preferably 5,000 or lower, more preferably 4,000 or lower, even more preferably 3,000 or lower, and is generally preferably 200 or higher, more preferably 300 or higher, even more preferably 400 or higher.

Compound (1) having a molecular weight within that range is easy to purify and has satisfactory heat resistance because the glass transition temperature, melting point, vaporization temperature, and the like of the compound are high.

[3. Properties]

(1) Glass Transition Temperature

It is preferred that compound (1) should have a glass transition temperature of generally 50° C. or higher. From the standpoint of heat resistance, the glass transition temperature thereof is preferably 80° C. or higher, more preferably 110° C. or higher.

(2) Vaporization Temperature

It is preferred that compound (1) should have a vaporization temperature of generally 300° C. to 800° C. It is preferred that the charge transport material of the invention should have no crystallization temperature between the glass transition temperature and the vaporization temperature.

(3) Solubility

It is preferred that compound (1) should be a compound which can dissolve in m-xylene in an amount of 5% by mass or more under the conditions of 25° C. and atmospheric pressure, from the standpoints of ensuring solubility in solvents and obtaining the property of forming films in a wet film formation method. The solubility thereof is preferably 10% by mass or more, more preferably 15% by mass or more. Although there is no particular upper limit on the solubility thereof, the solubility is generally preferably 50% by mass or less.

[4] Axis of Symmetry

In case where two or more of the substituents of a triphenylamine are the same, this compound has an axis of symmetry in the molecule like the compounds represented by the following general formulae (I-1) to (I-3).

[Chem. 12]

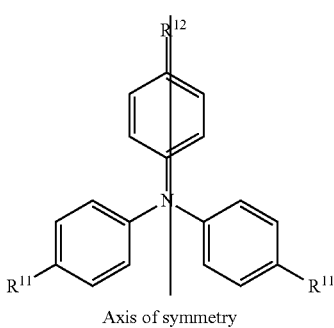

(I-1)

Axis of symmetry

[Chem. 13]

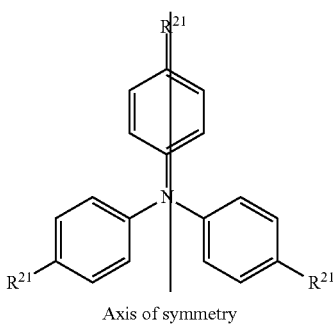

(I-2)

Axis of symmetry

[Chem. 14]

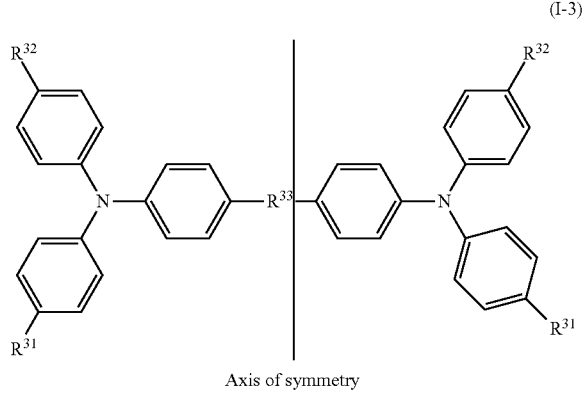

(I-3)

Axis of symmetry

In general formulae (I-1) to (I-3), $R^{11}$, $R^{12}$, $R^{21}$, $R^{31}$, $R^{32}$, and $R^{33}$ each independently represent a phenyl group which may have a substituent, and the substituents may have been bonded to each other to form a ring.

In contrast, all of $R^1$ to $R^3$ in compound (1) differ from each other and, hence, compound (1) has no axis of symmetry in the molecule. Consequently, the charge transport material of the invention is highly noncrystalline and has enhanced solubility in solvents.

[5. $R^1$ to $R^3$]

In formula (1), $R^1$ to $R^3$ each independently represent a phenyl group which may have a substituent in at least one of o- and m-positions, and the substituents may have been bonded to each other to form a cyclic structure. However, none of $R^1$, $R^2$, and $R^3$ is a group which is the same as any of the others.

Examples of the substituents possessed by the phenyl groups represented by $R^1$ to $R^3$ include alkyl groups which may have a substituent, alkenyl groups which may have a substituent, alkynyl groups which may have a substituent, aralkyl groups which may have a substituent, an amino group which may have a substituent, arylamino groups having an aromatic hydrocarbon group which has 6-12 carbon atoms and may have a substituent, heteroarylamino groups having a 5- or 6-membered aromatic heterocycle which may have a substituent, acylamino groups having an acyl group which has 2-10 carbon atoms and may have a substituent, alkoxy groups which may have a substituent, aryloxy groups which may have a substituent, heteroaryloxy groups which may have a substituent, acyl groups which may have a substituent, alkoxycarbonyl groups which may have a substituent, aryloxycarbonyl groups which may have a substituent, alkylcarbonyloxy groups which may have a substituent, halogen atoms, carboxy, cyano, hydroxy, mercapto, alkylthio groups which may have a substituent, arylthio groups which may have a substituent, sulfonyl groups which may have a substituent, silyl group which may have a substituent, boryl group which may have a substituent, phosphino group which may have a substituent, aromatic hydrocarbon groups which may have a substituent, and aromatic heterocyclic groups which may have a substituent.

The alkyl groups which may have a substituent preferably are linear or branched alkyl groups having 1-8 carbon atoms. Examples thereof include methyl, ethyl, n-propyl, 2-propyl, n-butyl, isobutyl, and tert-butyl.

The alkenyl groups which may have a substituent preferably are alkenyl groups having 2-9 carbon atoms. Examples thereof include vinyl, allyl, and 1-butenyl.

The alkynyl groups which may have a substituent preferably are alkynyl groups having 2-9 carbon atoms. Examples thereof include ethynyl and propargyl.

The aralkyl groups which may have a substituent preferably are aralkyl groups having 7-15 carbon atoms. Examples thereof include benzyl.

The amino group which may have a substituent preferably is an alkylamino group having one or more alkyl groups which each have 1-8 carbon atoms and may have a substituent. Examples thereof include methylamino, dimethylamino, diethylamino, and dibenzylamino.

Examples of the arylamino groups having an aromatic hydrocarbon group which has 6-12 carbon atoms and may have a substituent include phenylamino, diphenylamino, and ditolylamino.

Examples of the heteroarylamino groups having a 5- or 6-membered aromatic heterocycle which may have a substituent include pyridylamino, thienylamino, and dithienylamino.

Examples of the acylamino groups having an acyl group which has 2-10 carbon atoms and may have a substituent include acetylamino and benzoylamino.

The alkoxy groups which may have a substituent preferably are alkoxy groups which have 1-8 carbon atoms and may have a substituent. Examples thereof include methoxy, ethoxy, and butoxy.

The aryloxy groups which may have a substituent preferably are aryloxy groups which have an aromatic hydrocarbon group having 6-12 carbon atoms. Examples thereof include phenyloxy, 1-naphthyloxy, and 2-naphthyloxy.

The heteroaryloxy groups which may have a substituent preferably are heteroaryloxy groups having a 5- or 6-membered aromatic heterocyclic group. Examples thereof include pyridyloxy and thienyloxy.

The acyl groups which may have a substituent preferably are acyl groups which have 2-10 carbon atoms and may have a substituent. Examples thereof include formyl, acetyl, and benzoyl.

The alkoxycarbonyl groups which may have a substituent preferably are alkoxycarbonyl groups which have 2-10 carbon atoms and may have a substituent. Examples thereof include methoxycarbonyl and ethoxycarbonyl.

The aryloxycarbonyl groups which may have a substituent preferably are aryloxycarbonyl groups which have 7-13 carbon atoms and may have a substituent. Examples thereof include phenoxycarbonyl.

The alkylcarbonyloxy groups which may have a substituent preferably are alkylcarbonyloxy groups which have 2-10 carbon atoms and may have a substituent. Examples thereof include acetoxy.

The halogen atoms preferably are a fluorine atom and a chlorine atom.

The alkylthio groups which may have a substituent (preferably alkylthio groups having 1-8 carbon atoms; examples thereof include methylthio and ethylthio.), The arylthio groups which may have a substituent preferably are arylthio groups having 6-12 carbon atoms. Examples thereof include phenylthio and 1-naphthylthio.

Examples of the sulfonyl groups which may have a substituent include mesyl and tosyl.

Examples of the silyl group which may have a substituent include trimethylsilyl and triphenylsilyl.

Examples of the boryl group which may have a substituent include dimesitylboryl.

Examples of the phosphino group which may have a substituent include diphenylphosphino.

Examples of the aromatic hydrocarbon groups which may have a substituent include monovalent groups derived from 5- or 6-membered monocycles or di- to pentacyclic fused rings, such as a benzene ring, naphthalene ring, anthracene ring, phenanthrene ring, perylene ring, tetracene ring, pyrene ring, benzpyrene ring, chrysene ring, triphenylene ring, and fluoranthene ring.

Examples of the aromatic heterocyclic groups which may have a substituent include monovalent groups derived from 5- or 6-membered monocycles or di- to tetracyclic fused rings, such as a furan ring, benzofuran ring, thiophene ring, benzothiophene ring, pyrrole ring, pyrazole ring, imidazole ring, oxadiazole ring, indole ring, carbazole ring, pyrroloimidazole ring, pyrrolopyrazole ring, pyrrolopyrrole ring, thienopyrrole ring, thienothiophene ring, furopyrrole ring, furofuran ring, thienofuran ring, benzisoxazole ring, benzisothiazole ring, benzimidazole ring, pyridine ring, pyrazine ring, pyridazine ring, pyrimidine ring, triazine ring, quinoline ring, isoquinoline ring, cinnoline ring, quinoxaline ring, benzimidazole ring, perimidine ring, and quinazoline ring.

In the case where those substituents further have substituents, examples of the substituents include the substituents shown above as examples.

From the standpoints of improving electrochemical durability and improving heat resistance, the substituents of the phenyl groups represented by $R^1$ to $R^3$ are as follows. Preferred examples thereof are aromatic hydrocarbon groups which may have a substituent and aromatic heterocyclic groups which may have a substituent, and more preferred examples thereof are a phenyl group which may have a substituent and monovalent groups derived from the 5- or 6-membered monocycles or di- to tetracyclic fused rings. Even more preferred examples thereof are a phenyl group which is unsubstituted or has one or two substituents and an unsubstituted carbazole ring or benzofuran ring. The substituents of $R^1$ to $R^3$ may have two or more of the substituents shown above as examples, and may have been bonded to each other.

From the standpoint of further improving solubility and noncrystalline properties, it is preferred that the substituents of the phenyl groups represented by $R^1$ to $R^3$ should be alkyl groups which may have a substituent. More preferred are methyl, ethyl, n-propyl, 2-propyl, n-butyl, isobutyl, and tert-butyl. Even more preferred are methyl and ethyl.

The phenyl groups represented by $R^1$ to $R^3$ differ in the substituent introduced to the benzene ring of the phenyl group or differ with respect to the presence or absence of a substituent. $R^1$ to $R^3$ hence differ from each other.

$R^1$ to $R^3$ are phenyl groups which differ from each other as described above. It is preferred that the difference in the number of carbon atoms between the group among $R^1$ to $R^3$ which has a largest total number of carbon atoms, including the carbon atoms of the substituent, and the group which has a smallest total number of carbon atoms (hereinafter referred to as "carbon number difference in $R^1$-$R^3$") should be 10 or more.

It is preferred that the difference in the number of carbon atoms between the group among $R^1$ to $R^3$ which has a largest total number of carbon atoms, including the carbon atoms of the substituent, and the group which has a second largest total number of carbon atoms should be 5 or more. It is preferred that the difference in the number of carbon atoms between the group among $R^1$ to $R^3$ which has a smallest total number of carbon atoms, including the carbon atoms of the substituent, and the group which has a second largest total number of carbon atoms should be 5 or more.

Furthermore, it is more preferred that the difference in the number of carbon atoms between the group having a largest total number of carbon atoms and the group having a second largest total number of carbon atoms and the difference in the number of carbon atoms between the latter group and the group having a smallest total number of carbon atoms each should be 5 or more.

Compound (1) in which the carbon number difference in $R^1$-$R^3$ is 10 or more and each difference in the number of carbon atoms between two of $R^1$ to $R^3$ is 5 or more has even higher noncrystalline properties and even better solubility in various organic solvents. This compound (1) can form an organic thin film which is highly noncrystalline and does not crystallize readily.

The upper limit of the carbon number difference in $R^1$-$R^3$ is preferably 300, more preferably 150. By regulating the carbon number difference in $R^1$-$R^3$ to a value not larger than the upper limit, the charge-transporting ability can be prevented from decreasing.

Furthermore, the upper limit of each difference in the number of carbon atoms between two of $R^1$ to $R^3$ is preferably 200, more preferably 100. By regulating each difference in the number of carbon atoms between two of $R^1$ to $R^3$ to a value not larger than the upper limit, the charge-transporting ability can be prevented from decreasing.

Incidentally, the upper limit of the total number of carbon atoms in each of $R^1$ to $R^3$ is preferably 350, more preferably 150.

[6] Especially Preferred Partial Structures

In the case where the monoamine compound of the invention is to be used as the charge transport material which will be described later, it is especially preferred that compound (1) should have an m-phenylene group, which is represented by the following structural formula (2-1), in the molecule, from the standpoint of further improving solubility in solvents. It is preferred that the m-phenylene group should be contained as a partial structure of any one of $R^1$ to $R^3$.

[Chem. 15]

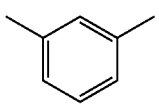
(2-1)

In structural formula (2-1), the phenyl group may further have one or more substituents, and the substituents may have been bonded to each other to form a cyclic structure.

In the case where the monoamine compound of the invention is to be used as a charge transport material, it is especially preferred that compound (1) should have in the molecule a group including a partial structure represented by the following general formula (2-2), from the standpoint of improving heat resistance while maintaining a high triplet excitation level.

In the case where the charge transport material of the invention contains a group including a partial structure represented by the following general formula (2-2), it is preferred that at least one of $R^1$ to $R^3$ in compound (1) should be a group including the partial structure represented by the following general formula (2-2).

[Chem. 16]

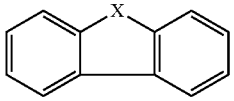
(2-2)

X in general formula (2-2) represents any one of —NR$^4$— (where $R^4$ represents an aryl group which may have a substituent), —O—, and —S—. The X-containing fused ring in general formula (2-2) may further have one or more substituents, and the substituents may have been bonded to each other to form a cyclic structure.

From the standpoints of heat resistance and solubility, it is preferred that X in general formula (2-2) should be —NR$^4$— (where $R^4$ represents an aryl group which may have a substituent) or —O—.

The X-containing fused ring in general formula (2-2) may further have one or more substituents. Examples of the substituents include the same groups as the substituents which may be possessed by the above-described phenyl groups represented by $R^1$ to $R^3$ contained in compound (1). In the invention, it is preferred that the X-containing fused ring in general formula (2-2) should have no substituent.

From the standpoint of enabling the charge transport material of the invention to more effectively exhibit excellent electron-transporting ability, which is a feature of the material, it is preferred that any one of $R^1$ to $R^3$ in compound (1) should contain a group including a partial structure represented by general formula (2-2) as stated above.

It is preferred that the partial structure represented by general formula (2-2) should be an N-carbazolyl group, which is represented by the following structural formula (3), from the standpoints of charge-transporting properties and heat resistance.

[Chem. 17]

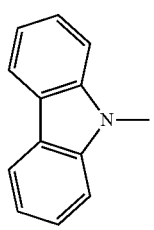
(3)

In structural formula (3), the N-carbazole ring may further have one or more substituents, and the substituents may have been bonded to each other to form a cyclic structure.

From the standpoint of further improving solubility in solvents, it is especially preferred that at least one of $R^1$ to $R^3$ in compound (1) should be a group represented by the following general formula (11).

[Chem. 18]

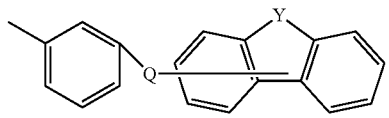
(11)

In general formula (11), Q represents a direct bond or any linking group. Y has the same meaning as the X contained in general formula (2-2). The Y-containing fused ring in general formula (11) may have one or more substituents, and the substituents may be bonded to each other to form a cyclic structure.

The Y-containing fused ring in general formula (11) may further have a substituent, and examples of the substituent include the same groups as the substituents which may be possessed by the above-described phenyl groups represented by $R^1$ to $R^3$. In the invention, it is preferred that the Y-containing fused ring in general formula (11) should have no substituent.

Q is a direct bond or any linking group. In the case where Q is any linking group, this group preferably is a divalent aromatic hydrocarbon group. Specifically, the linking group preferably is a phenylene group or is two or more phenylene groups linked to each other.

Examples of the two or more phenylene groups linked to each other include a biphenylene group and a terphenylene group.

It is most preferred that Q should be directly bonded to a meta-position atom of the benzene ring bonded to the main framework of the compound represented by general formula (1), as shown in general formula (11).

Namely, it is most preferred that the part (Y-containing fused ring) which mainly serves to transport holes should be bonded through a benzene ring in a meta position. As a result, not only compound (1) has improved solubility in solvents, but also the excellent electrochemical stability, excellent heat resistance, and high triplet excitation level are not impaired because of the excellent heat resistance, excellent electrochemical stability, and high triplet excitation level of the benzene ring. Consequently, it is preferred that Q should be a group composed of m-phenylene groups linked to each other. The number of such m-phenylene groups linked to each other is preferably 1-5, more preferably 2-3.

It is especially preferred that compound (1) in the invention should be a compound which is represented by the following general formula (4) and has no axis of symmetry (hereinafter often referred to as "compound (4)").

[Chem. 19]

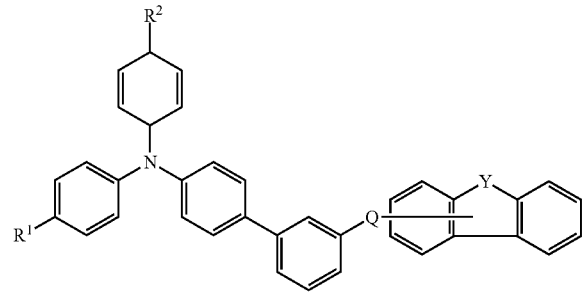

(4)

In general formula (4), $R^1$ and $R^2$ have the same meanings as the $R^1$ and $R^2$ contained in general formula (1). Q and Y have the same meanings as in general formula (11).

$R^1$ and $R^2$ in general formula (4) have the same meanings as the $R^1$ and $R^2$ contained in general formula (1), and preferred examples thereof are as explained above in the section [5. $R^1$ to $R^3$].

It is especially preferred that the partial structure in general formula (4) which corresponds to the $R^3$ contained in general formula (1) should be a group represented by the following general formula (6) or (7), from the standpoint of improving solubility in solvents and heat resistance.

[Chem. 20]

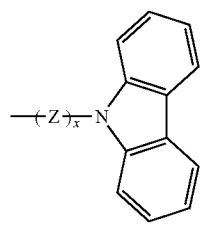

(6)

In general formula (6), Z represents a phenylene group which may have a substituent; at least the first phenylene group, among the x phenylene groups, that is bonded to the main framework of the compound represented by general formula (1) is an m-phenylene group; and x represents an integer of 2-6.

In general formula (6), x is 2-6 and is preferably 2-4, especially preferably 2-3.

[Chem. 21]

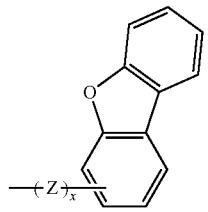

(7)

In general formula (7), Z represents a phenylene group which may have a substituent; at least the first phenylene group, among the x phenylene groups, that is bonded to the main framework of the compound represented by general formula (1) is an m-phenylene group; and x represents an integer of 2-6.

In general formula (7), x is 2-4 and is preferably 2-3.

On the other hand, it is especially preferred that $R^1$ in general formula (4) should be a group represented by the following general formula (8) or (9).

[Chem. 22]

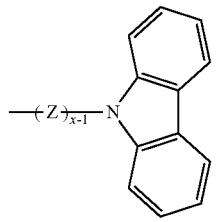

(8)

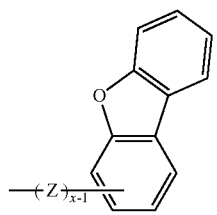

(9)

In general formulae (8) and (9), Z represents a phenylene group which may have a substituent; at least the first phenylene group, among the x-1 phenylene groups, that is bonded to the main framework of the compound represented by general formula (1) is an m-phenylene group; and x represents an integer of 2-6.)

Furthermore, it is especially preferably that $R^2$ should be a group represented by the following general formula (10).

—$(Z)_y$-Ph (10)

In general formula (10), Z represents a phenylene group which may have a substituent; at least the first phenylene group, among the y phenylene groups, that is bonded to the main framework of the compound represented by general formula (1) is an m-phenylene group; Ph represents a phenyl group which may have a substituent; and y represents an integer of 1-5.

Here, y is 1-5, and is preferably 1-3.

[8. Exemplification]

Preferred examples of the monoamine compound of the invention are shown below. However, the invention should not be construed as being limited to the following examples.

[Chem. 23]

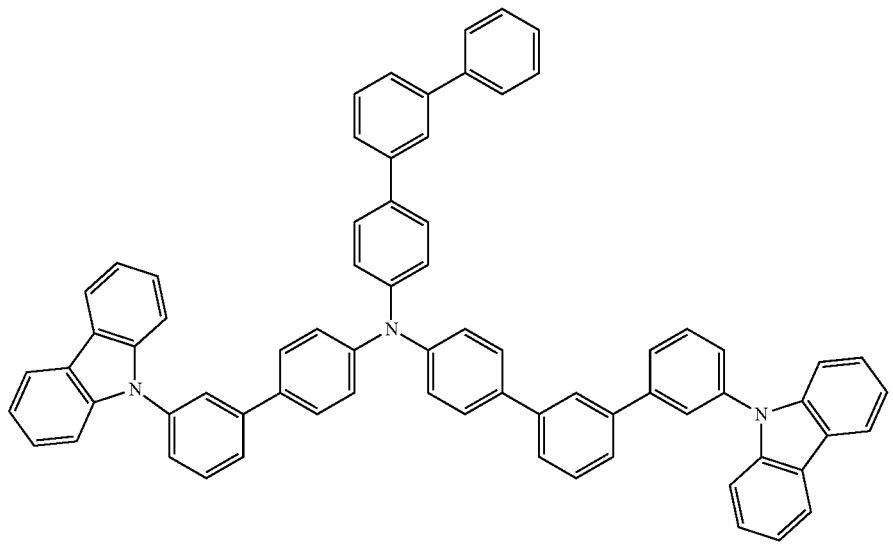

(1-1)

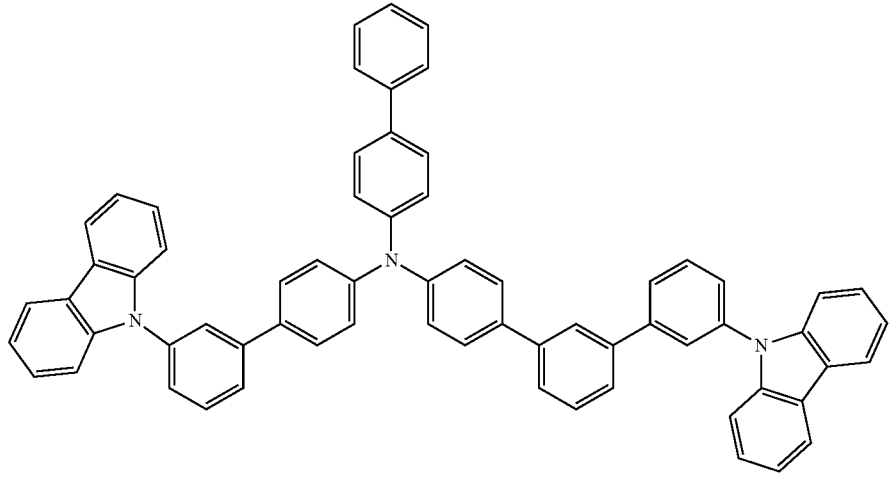

(1-2)

(1-3)
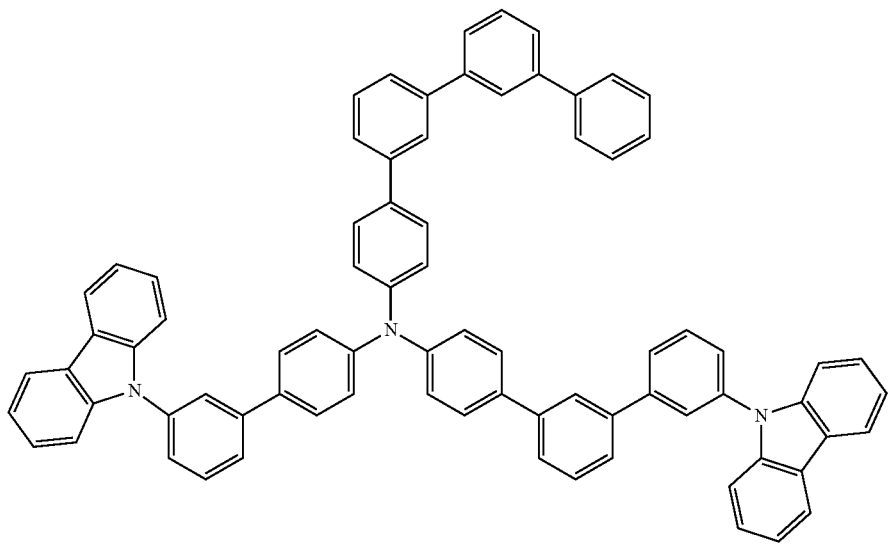
(1-4)
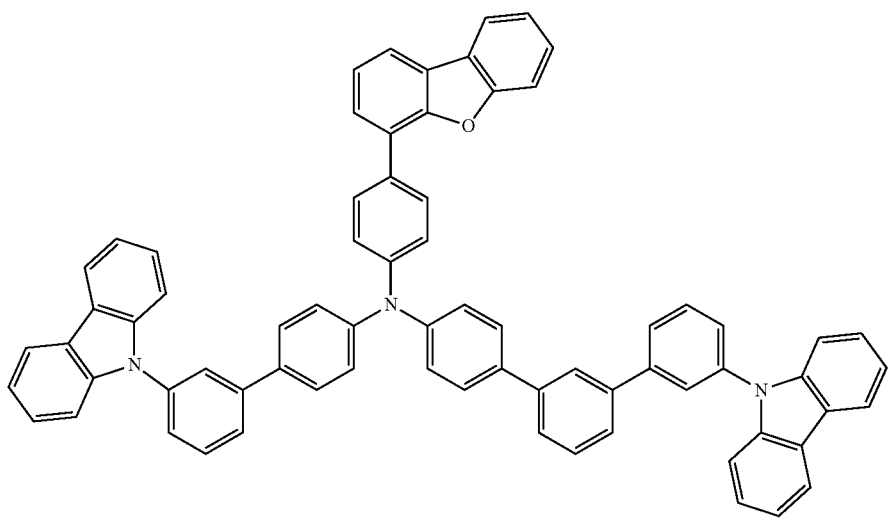
(1-5)
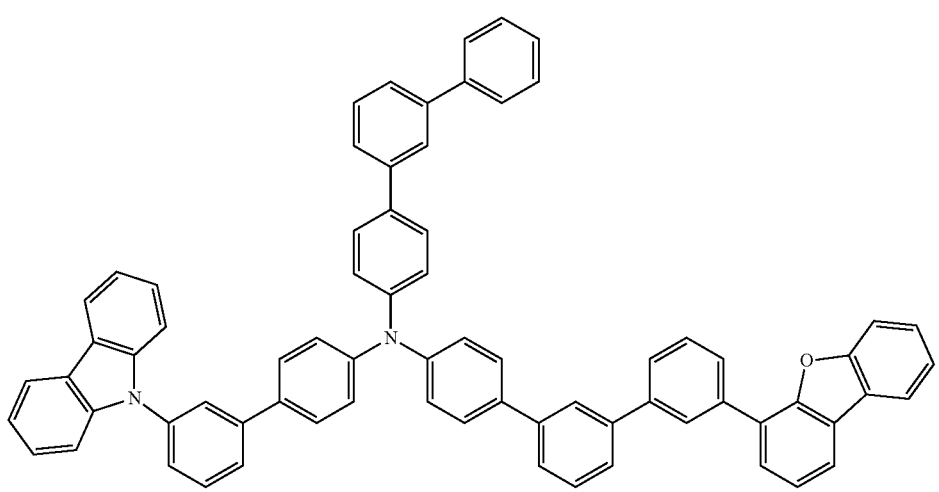

(1-6)
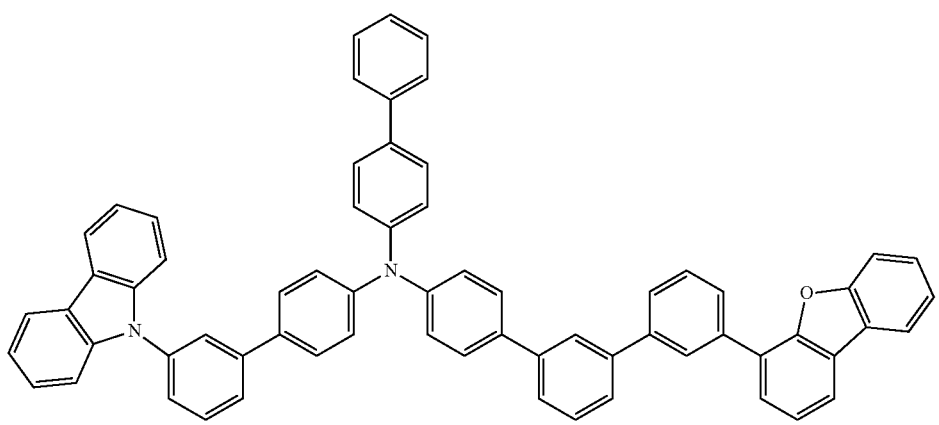
(1-7)
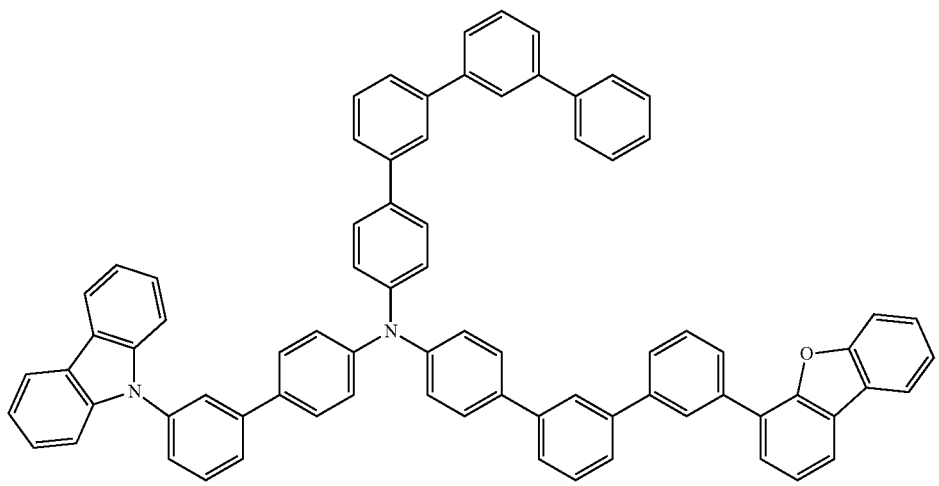
(1-8)
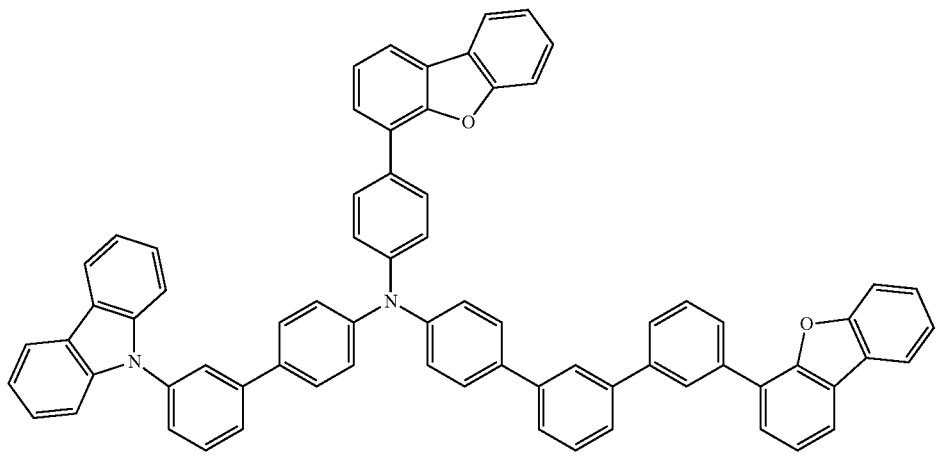

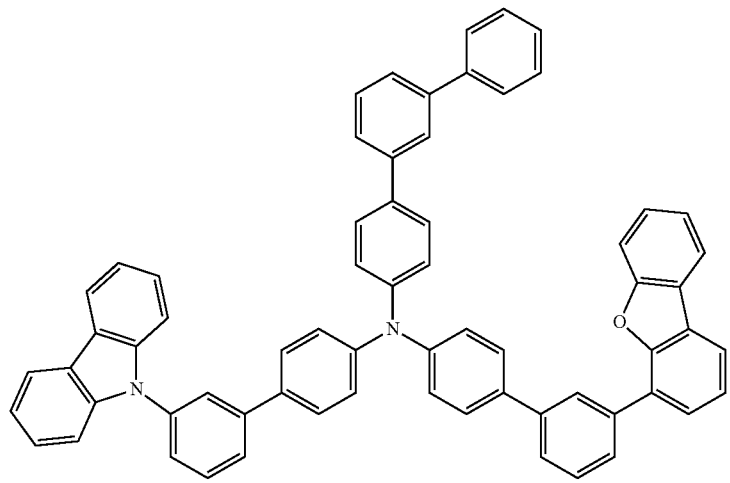
(1-9)
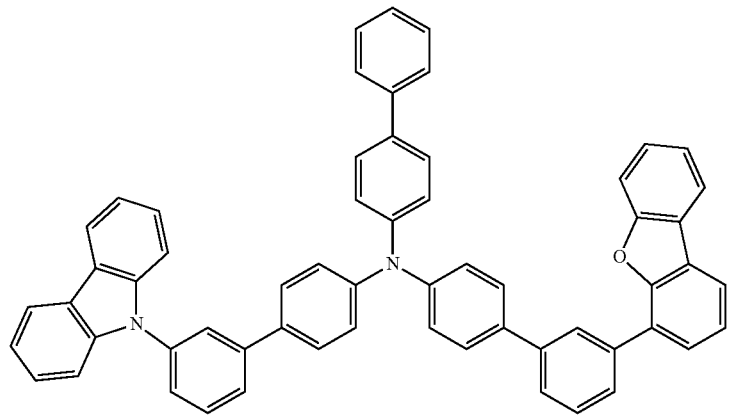
(1-10)
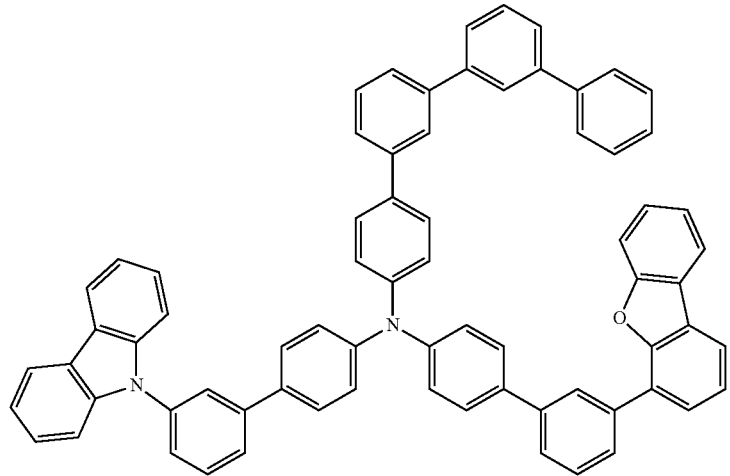
(1-11)

(1-12)
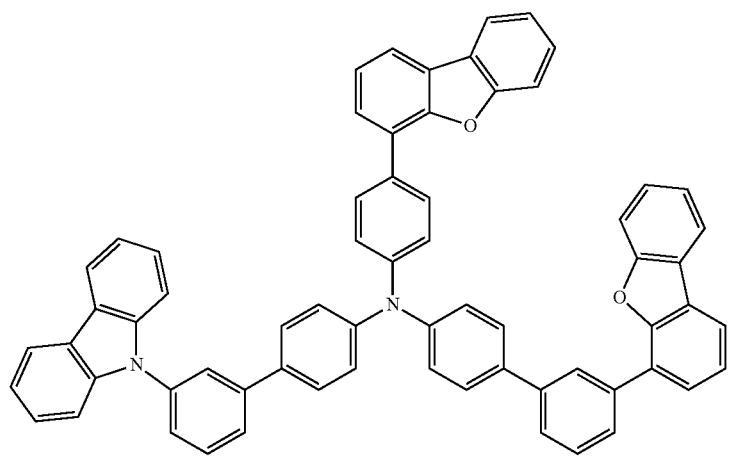
[Chem. 24]
(1-13)
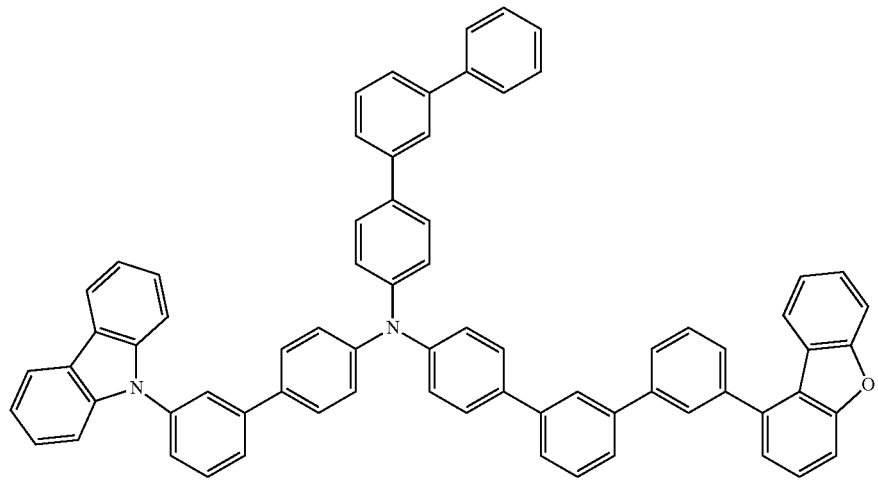
(1-14)
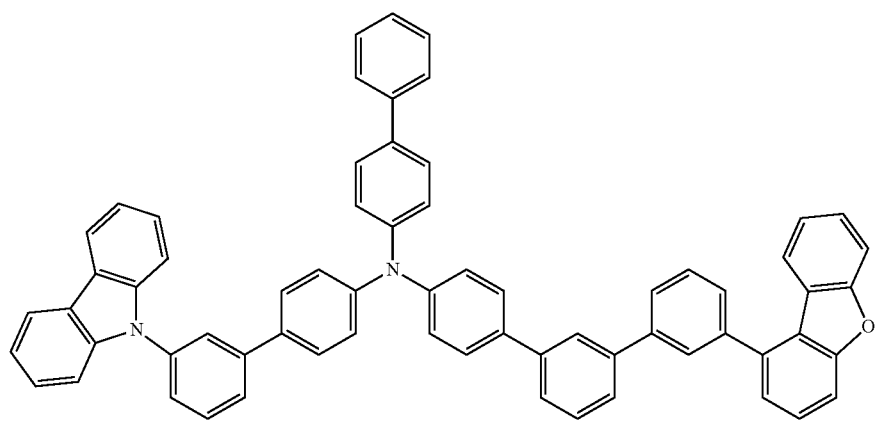

(1-15)
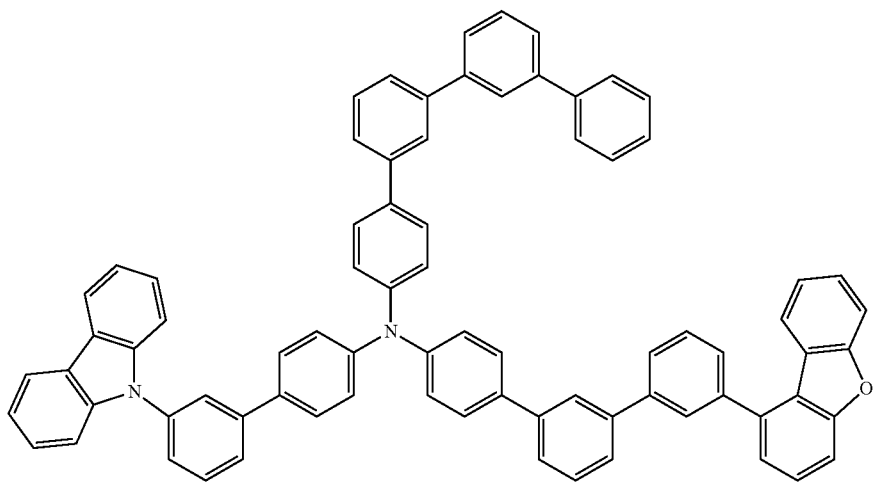
(1-16)
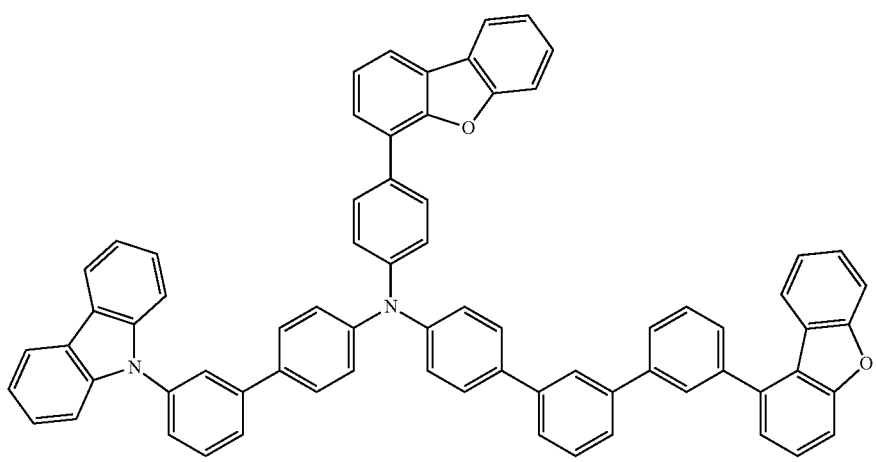
(1-17)
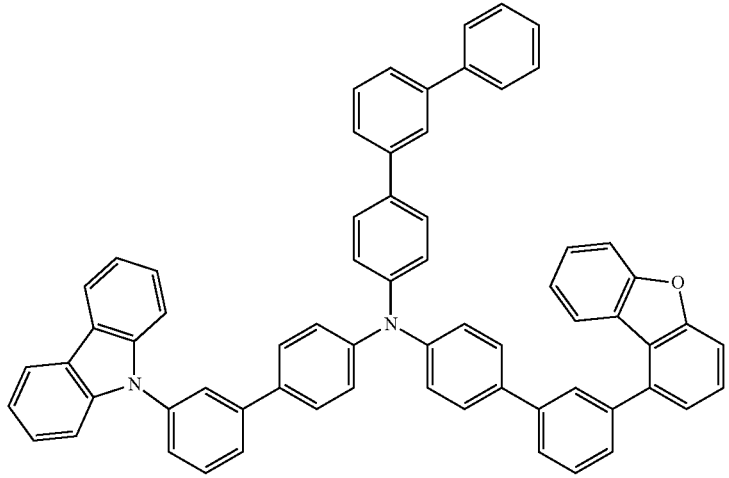

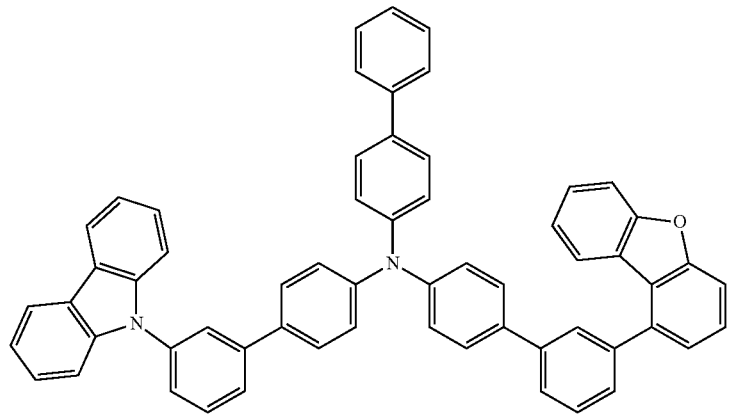
(1-18)
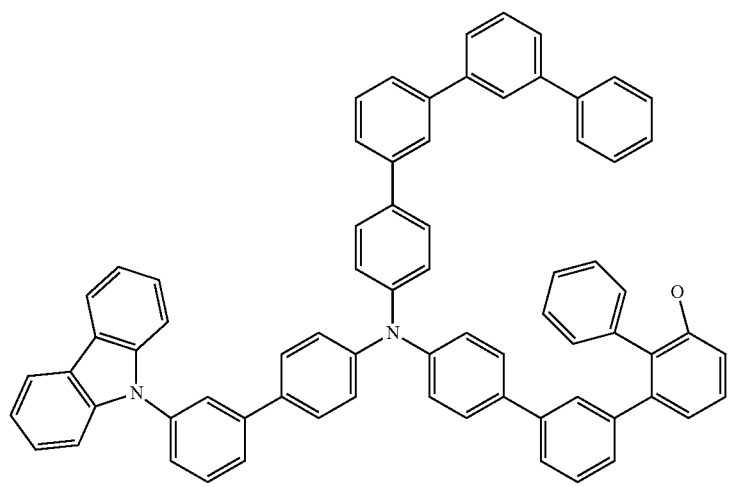
(1-19)
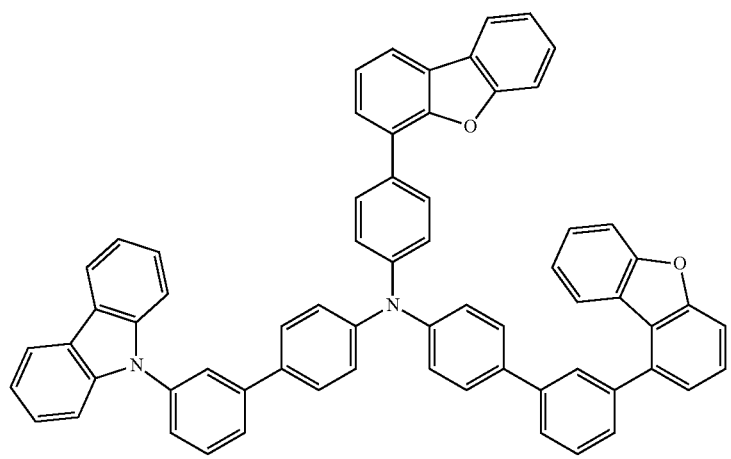
(1-20)

[Chem. 25]
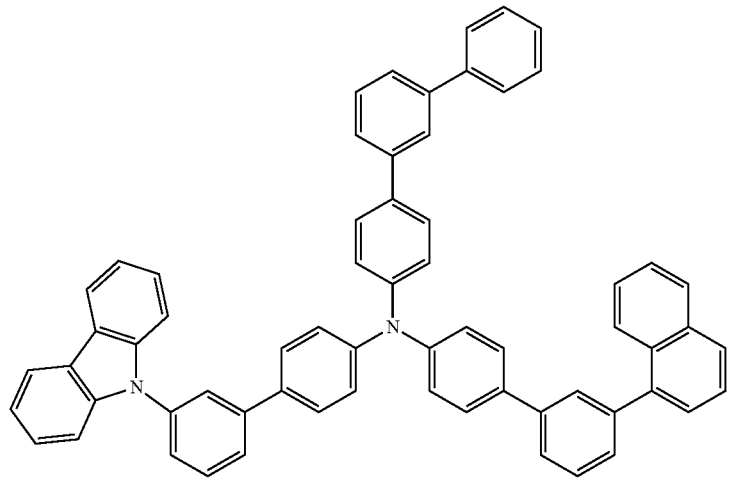
(1-21)
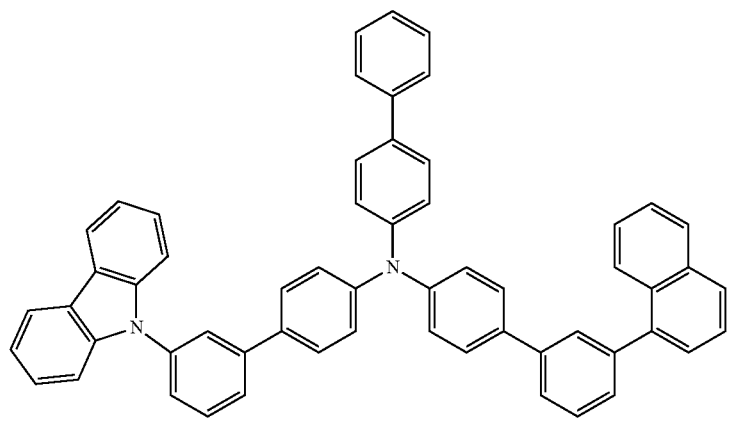
(1-22)
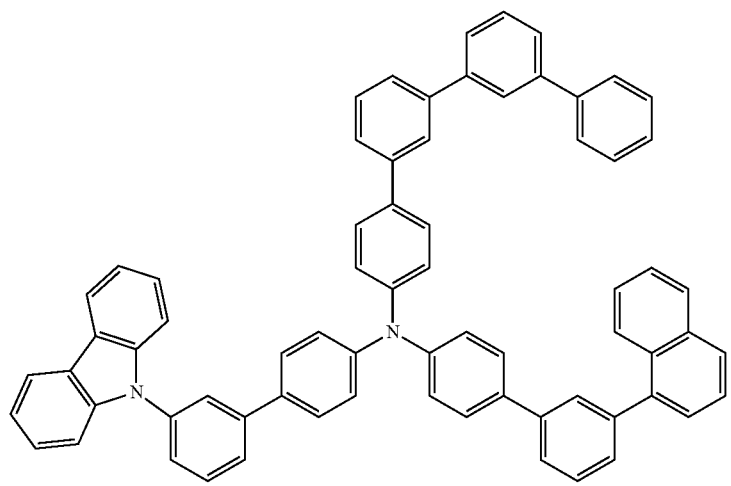
(1-23)

(1-24)
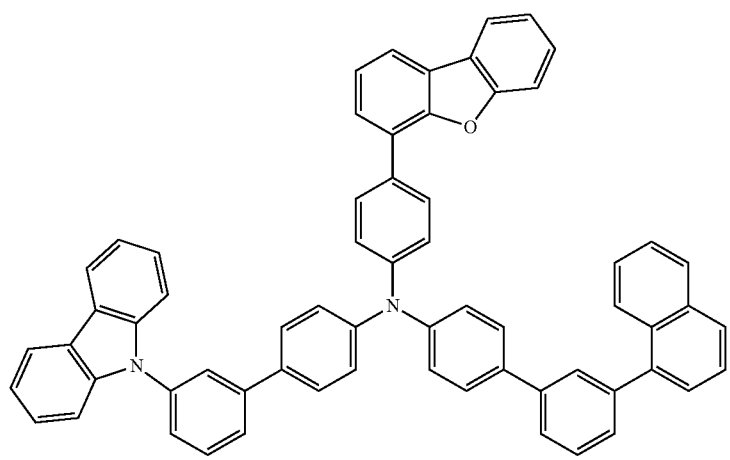
(1-25)
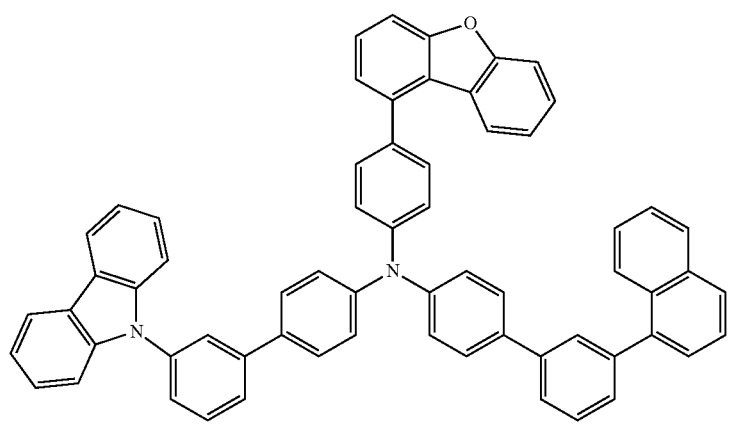
(1-26)
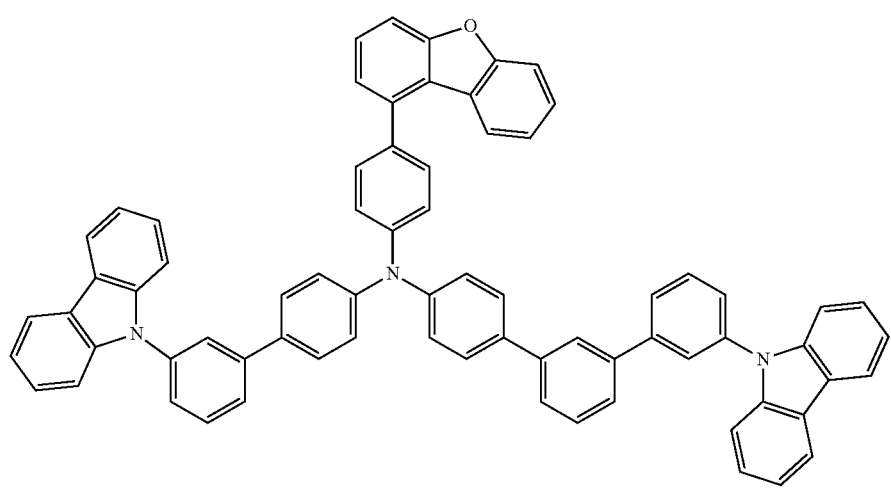

[9. Synthesis Methods]

The charge transport material of the invention can be synthesized, for example, from an arylamine compound as a starting material by successively introducing aromatic rings.

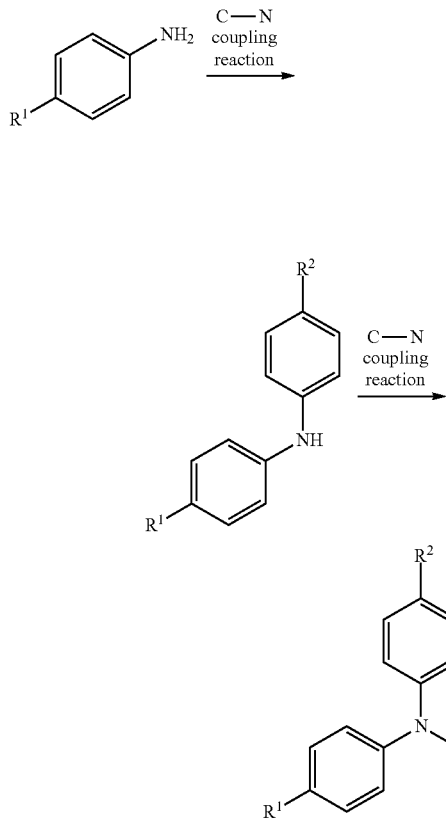

[Chem. 26]

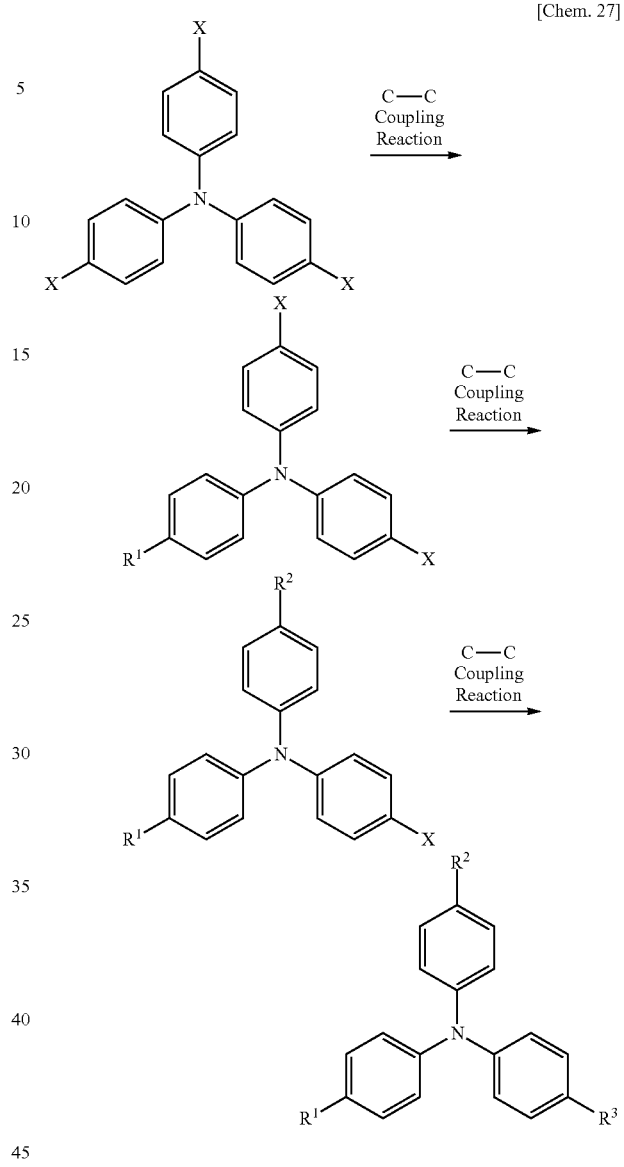

[Chem. 27]

(C—N Coupling Reaction)

The substrate is reacted with a halide or trifluoromethanesulfonic acid ester reagent which has an aromatic hydrocarbon group, in the presence of a base using a transition metal element catalyst. Thus, an amino group can be introduced to the aromatic hydrocarbon group.

Isolation and purification can be conducted by means of a combination of operations, such as, e.g., distillation, filtration, extraction, recrystallization, reprecipitation, suspension washing, and chromatography.

Examples of the transition metal element catalyst include palladium catalysts and copper catalysts. Palladium catalysts are preferred from the standpoints of ease of the reaction and high yield.

The base is not particularly limited. For example, use can be made of potassium carbonate, cesium carbonate, tert-butoxysodium, triethylamine, and the like.

With respect to a solvent, toluene is preferred when a palladium catalyst is used. When a copper catalyst is used, pyridine, N,N-dimethylformamide (DMF), dimethyl sulfoxide (DMSO), and the like are preferred.

Compound (1) according to the invention can be synthesized also from a trihalide of a triarylamine as a starting material by successively conducting coupling reactions.

(C—C Coupling Reaction)

The substrate is reacted with an organometallic reagent having an aromatic hydrocarbon group in a nonpolar or polar solvent in the presence of a base using a transition metal element catalyst. Thus, the aromatic hydrocarbon group can be introduced to the substrate.

Isolation and purification can be conducted by means of a combination of operations, such as, e.g., distillation, filtration, extraction, recrystallization, reprecipitation, suspension washing, and chromatography.

Examples of the organometallic reagent include organoboron reagents, organomagnesium reagents, and organozinc reagents. Of these, organoboron reagents are preferred from the standpoint of ease of handling.

Examples of the transition metal element catalyst include organopalladium catalysts, organonickel catalysts, organocopper catalysts, organoplatinum catalysts, organorhodium catalysts, organoruthenium catalysts, and organoiridium catalysts. Of these, organopalladium catalysts are preferred from the standpoints of ease of the reaction and high yield.

The base is not particularly limited. However, metal hydroxides, metal salts, organic alkali metal reagents, and the like are preferred.

The solvent to be used is not particularly limited so long as the solvent does not act on the substrate. Examples thereof include aliphatic hydrocarbons such as hexane, heptane, and cyclohexane; aromatic hydrocarbons such as benzene, toluene, and xylene; ethers such as dimethoxyethane, tetrahydrofuran, and dioxane; alcohols such as ethanol and propanol; and water. These solvents can be used alone or as a mixture thereof.

According to need, a surfactant can be added in an amount of 1-100 mol %.

[Charge Transport Material]

The charge transport material of the invention includes a monoamine compound represented by general formula (1). Since the monoamine compound has excellent solubility in solvents and high noncrystalline properties, a thin film can be formed by a wet film formation method.

Furthermore, since the monoamine compound included in the charge transport material of the invention further has excellent charge-transporting properties and excellent durability concerning electrical oxidation/reduction and has a high triplet excitation level, use of the charge transport material in organic electroluminescent elements renders a high luminescent efficiency and high driving stability possible.

[Composition for Charge Transport Film]

The composition for charge transport film of the invention contains the charge transport material of the invention described above, and it is preferred that the composition should be used for organic electroluminescent elements.

[1] Solvent

It is preferred that the composition for charge transport film of the invention, in particular, the composition for charge transport film to be used as a composition for organic electroluminescent elements, should contain a solvent.

The solvent to be contained in the composition for charge transport film of the invention is not particularly limited so long as the solutes including the charge transport material of the invention satisfactorily dissolve therein.

Since the charge transport material of the invention has exceedingly high solubility in solvents, various solvents can be applied. For example, use can be made of aromatic hydrocarbons such as toluene, xylene, mesitylene, cyclohexylbenzene, and tetralin; halogenated aromatic hydrocarbons such as chlorobenzene, dichlorobenzene, and trichlorobenzene; aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, and 2,4-dimethylanisole; aromatic esters such as phenyl acetate, phenyl propionate, methyl benzoate, ethyl benzoate, propyl benzoate, and n-butyl benzoate; alicyclic ketones such as cyclohexanone and cyclooctanone; aliphatic ketones such as methyl ethyl ketone and dibutyl ketone; alicyclic alcohols such as methyl ethyl ketone, cyclohexanol, and cyclooctanol; aliphatic alcohols such as butanol and hexanol; aliphatic ethers such as ethylene glycol dimethyl ether, ethylene glycol diethyl ether, and propylene glycol 1-monomethyl ether acetate (PGMEA); aliphatic esters such as ethyl acetate, n-butyl acetate, ethyl lactate, and n-butyl lactate; and the like.

Of these, aromatic hydrocarbons such as toluene, xylene, mesitylene, cyclohexylbenzene, and tetralin are preferred from the standpoints of low solubility of water therein and little tendency to alter.

Organic electroluminescent elements employ a large number of materials which deteriorate considerably by the action of moisture, e.g., the cathode. There is hence a possibility that when moisture is present in the composition, the film formed through drying might contain moisture remaining therein and the residual moisture might reduce the characteristics of the element. It is therefore preferred to reduce the water content of the composition.

Examples of methods for reducing the water content of the composition include sealing with nitrogen gas, use of a drying agent, solvent dehydration conducted beforehand, and use of a solvent in which water is poorly soluble. Use of a solvent in which water is poorly soluble is preferred of these methods because the phenomenon in which during a wet film formation step, the coating film of the solution absorbs atmospheric moisture to blush can be prevented in this case.

From such a standpoint, the solvent to be contained in the composition for charge transport film of the invention should have a water solubility therein at 25° C. of preferably 1% by mass or less, more preferably 0.1% by mass or less. It is also preferred that this solvent should be contained in the composition in an amount of 10% by mass or more.

From the standpoint of inhibiting film formation stability from being reduced by solvent vaporization from the composition during wet film formation, the boiling point of the solvent of the composition for charge transport film is preferably 100° C. or higher, more preferably 150° C. or higher, even more preferably 200° C. or higher.

For obtaining a more even film, it is necessary that the solvent should vaporize at an appropriate rate from the liquid film immediately after formation of the film. In order for the solvent to satisfy this, the lower limit of the boiling point of the solvent is generally preferably 80° C., more preferably 100° C., even more preferably 120° C. The upper limit thereof is generally preferably lower than 270° C., more preferably lower than 250° C., even more preferably lower than 230° C.

A solvent which satisfies those requirements, i.e., the requirements concerning solubility of solutes therein, vaporization rate, and water solubility therein, may be used alone. However, in the case where it is impossible to select a solvent which satisfy all the requirements, a mixture of two or more solvents can be used.

[2] Luminescent Material

It is preferred that the composition for charge transport film of the invention, in particular, the composition for charge transport film which is to be used as a composition for organic electroluminescent elements, should contain a luminescent material.

The term luminescent material means an ingredient which mainly luminesces in the composition of charge transport layer formation of the invention, and the luminescent material corresponds to a dopant ingredient in organic electroluminescent devices. Namely, when generally 10-100%, preferably 20-100%, more preferably 50-100%, and most preferably 80-100% of the quantity of light (unit: $cd/m^2$) emitted from a composition for charge transport film is ascertained to be attributable to luminescence from a certain ingredient material, then the ingredient is defined as a luminescent material.

As the luminescent material, any desired known material can be used. For example, one of fluorescent materials or one of phosphorescent materials can be used alone, or a mixture of two or more of these materials can be used. From the standpoint of inner-quantum efficiency, phosphorescent materials are preferred.

It is preferred that the luminescent material should have a maximum luminescence peak wavelength in the range of 390-490 nm.

It is possible to reduce the symmetry or stiffness of the molecule of a luminescent material or to introduce an oleophilic substituent such as an alkyl group thereto, for the purpose of improving solubility in solvents.

Examples of fluorescent dyes which give blue luminescence include perylene, pyrene, anthracene, coumarin, p-bis (2-phenylethenyl)benzene, and derivatives of these.

Examples of green fluorescent dyes include quinacridone derivatives and coumarin derivatives.

Examples of yellow fluorescent dyes include rubrene and perimidone derivatives.

Examples of red fluorescent dyes include DCM type compounds, benzopyran derivatives, Rhodamine derivatives, benzothioxanthene derivatives, and azabenzothioxanthene.

Examples of phosphorescent materials include organometallic complexes containing a metal selected from Groups 7 to 11 of the periodic table.

Preferred examples of the metal in the phosphorescent organometallic complexes containing a metal selected from Groups 7 to 11 of the periodic table include ruthenium, rhodium, palladium, silver, rhenium, osmium, iridium, platinum, and gold. Preferred as these organometallic complexes are compounds represented by the following general formula (V) and formula (VI).

(V)

In general formula (V), M represents a metal and q represents the valence of the metal. L and L' represent a bidentate ligand. Symbol j represents an integer of 0-2.

[Chem. 28]

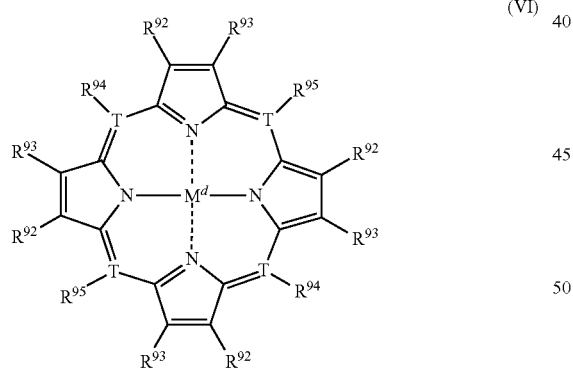
(VI)

In general formula (VI), $M^d$ represents a metal, and T represents a carbon atom or a nitrogen atom. $R^{92}$ to $R^{95}$ each independently represent a substituent. However, when T is a nitrogen atom, $R^{94}$ and $R^{95}$ are absent.

The compounds represented by general formula (V) are explained first below.

In general formula (V), M represents any metal. Preferred examples thereof include the metals enumerated above as metals selected from Groups 7 to 11 of the periodic table.

The bidentate ligands L and L' in general formula (V) each represent a ligand including the following partial structure.

[Chem. 29]

L: 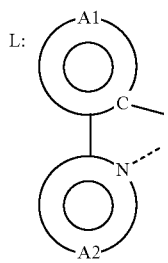

[Chem. 30]

L': 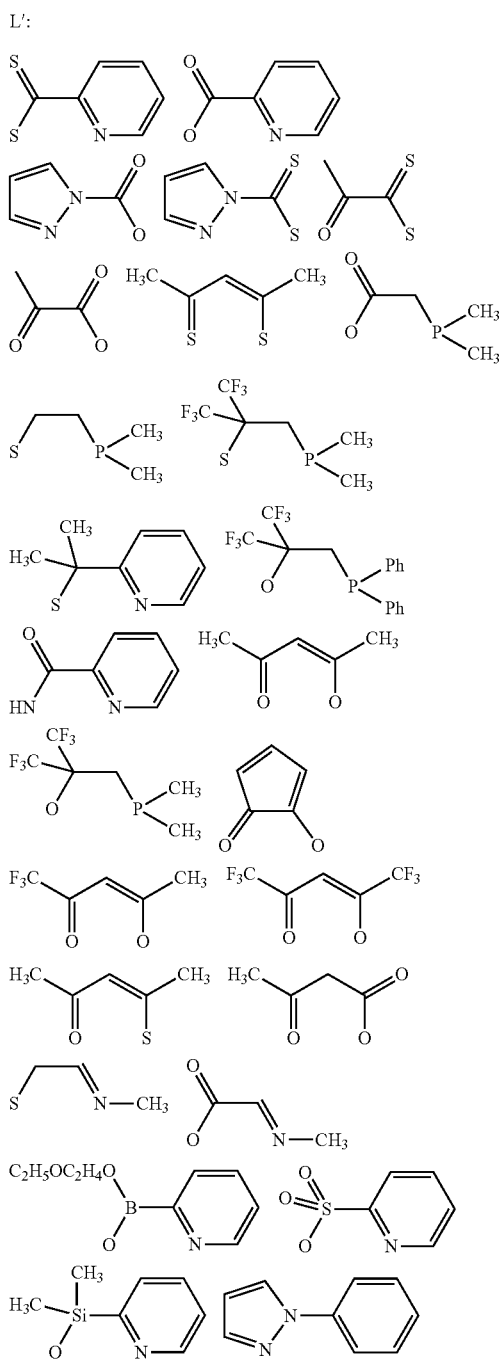

-continued

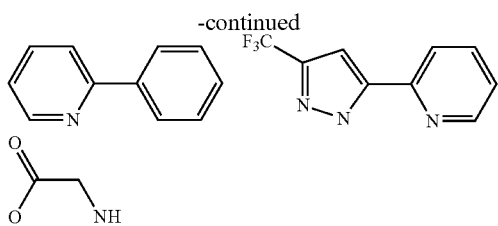

The following are especially preferred as L' from the standpoint of the stability of the complex.

[Chem. 31]

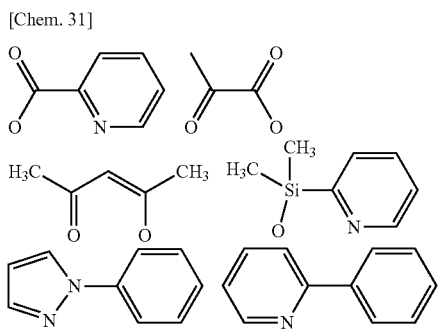

In the partial structures of L and L', ring A1 represents an aromatic hydrocarbon group or an aromatic heterocyclic group, and ring A2 represents a nitrogen-containing aromatic heterocyclic group. These groups may have substituents.

In the case where rings A1 and A2 have substituents, suitable examples of the substituents include halogen atoms such as a fluorine atom; alkyl groups such as methyl and ethyl; alkenyl groups such as vinyl; alkoxycarbonyl groups such as methoxycarbonyl and ethoxycarbonyl; alkoxy groups such as methoxy and ethoxy; aryloxy groups such as phenoxy and benzyloxy; dialkylamino groups such as dimethylamino and diethylamino; diarylamino groups such as diphenylamino; carbazolyl; acyl groups such as acetyl; haloalkyl groups such as trifluoromethyl; cyano; and aromatic hydrocarbon groups such as phenyl, naphthyl, and phenanthyl.

Suitable examples of the compounds represented by general formula (V) include compounds represented by the following formulae (Va), (Vb), and (Vc).

[Chem. 32]

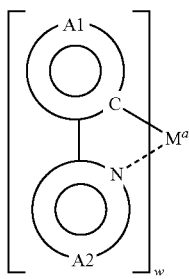

(Va)

In general formula (Va), $M^a$ represents a metal, and w represents the valence of the metal. Ring A1 represents an aromatic hydrocarbon group which may have a substituent, and ring A2 represents a nitrogen-containing aromatic heterocyclic group which may have a substituent.

[Chem. 33]

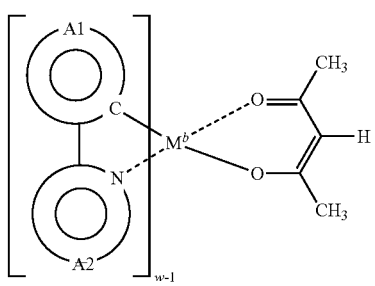

(Vb)

In general formula (Vb), $M^b$ represents a metal, and w represents the valence of the metal. Ring A1 represents an aromatic hydrocarbon group which may have a substituent or an aromatic heterocyclic group which may have a substituent, and ring A2 represents a nitrogen-containing aromatic heterocyclic group which may have a substituent.

[Chem. 34]

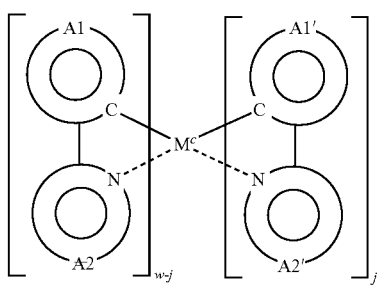

(Vc)

In general formula (Vc), $M^c$ represents a metal, and w represents the valence of the metal. Symbol j represents an integer of 0-2. Ring A1 and ring A1' each independently represent an aromatic hydrocarbon group which may have a substituent or an aromatic heterocyclic group which may have a substituent. Furthermore, ring A2 and ring A2' each independently represent a nitrogen-containing aromatic heterocyclic group which may have a substituent.

Suitable examples of the groups constituting ring A1 and ring A1' in general formulae (Va), (Vb), and (Vc) include phenyl, biphenyl, naphthyl, anthryl, thienyl, furyl, benzothienyl, benzofuryl, pyridyl, quinolyl, isoquinolyl, and carbazolyl.

Suitable examples of the groups constituting ring A2 and ring A2' include pyridyl, pyrimidyl, pyrazyl, triazyl, benzothiazole group, benzoxazole group, benzimidazole group, quinolyl, isoquinolyl, quinoxalyl, and phenanthridyl.

Furthermore, examples of the substituents which may be possessed by ring A1, ring A1', ring A2, and ring A2' include halogen atoms such as a fluorine atom; alkyl groups such as methyl and ethyl; alkenyl groups such as vinyl; alkoxycarbonyl groups such as methoxycarbonyl and ethoxycarbonyl; alkoxy groups such as methoxy and ethoxy; aryloxy groups such as phenoxy and benzyloxy; dialkylamino groups such as dimethylamino and diethylamino; diarylamino groups such as diphenylamino; carbazolyl; acyl groups such as acetyl; haloalkyl groups such as trifluoromethyl; and cyano.

In the case where the substituents are alkyl groups, it is preferred that the groups each should have generally 1-6 carbon atoms.

In the case where the substituents are alkenyl groups, it is preferred that the groups each should have generally 2-6 carbon atoms.

In the case where the substituents are alkoxycarbonyl groups, it is preferred that the groups each should have generally 2-6 carbon atoms.

In the case where the substituents are alkoxy groups, it is preferred that the groups each should have generally 1-6 carbon atoms.

In the case where the substituents are aryloxy groups, it is preferred that the groups each should have generally 6-14 carbon atoms.

In the case where the substituents are dialkylamino groups, it is preferred that the groups each should have generally 2-24 carbon atoms.

In the case where the substituents are diarylamino groups, it is preferred that the groups each should have generally 12-28 carbon atoms.

In the case where the substituents are acyl groups, it is preferred that the groups each should have generally 1-14 carbon atoms.

In the case where the substituents are haloalkyl groups, it is preferred that the groups each should have generally 1-12 carbon atoms.

Those substituents may be bonded to each other to form a ring. For example, the substituent possessed by ring A1 and the substituent possessed by ring A2 may be bonded to each other to form a fused ring, or the substituent possessed by ring A1' and the substituent possessed by ring A2' may be bonded to each other to form a fused ring. Examples of such fused rings include a 7,8-benzoquinoline group.

Preferred of those substituents of ring A1, ring A1', ring A2, and ring A2' are alkyl groups, alkoxy groups, aromatic hydrocarbon groups, cyano, halogen atoms, haloalkyl groups, diarylamino groups, and carbazolyl.

Examples of $M^a$, $M^b$, and $M^c$ include the same metals as the metals enumerated above with regard to M. Preferred of these are ruthenium, rhodium, palladium, silver, rhenium, osmium, iridium, platinum, and gold.

Specific examples of the organometallic complexes represented by general formula (V), (Va), (Vb), or (Vc) are shown below. However, the complexes should not be construed as being limited to the following compounds (wherein Ph' represents phenyl).

[Chem. 35]

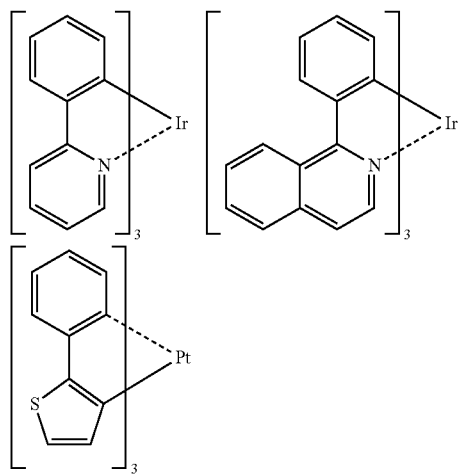

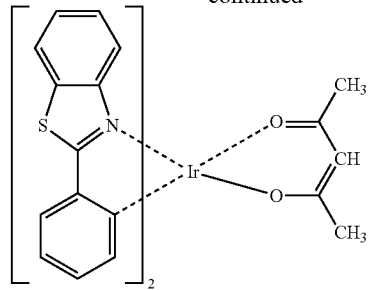

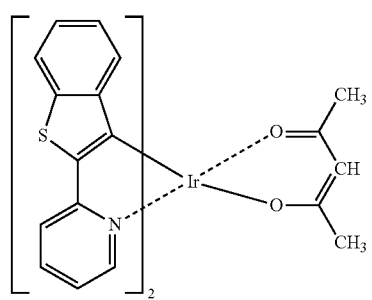

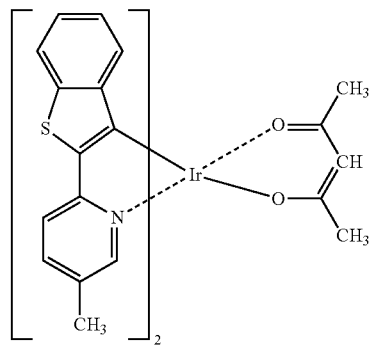

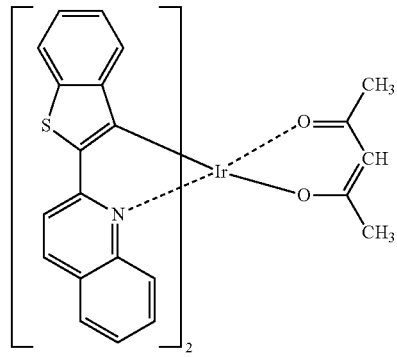

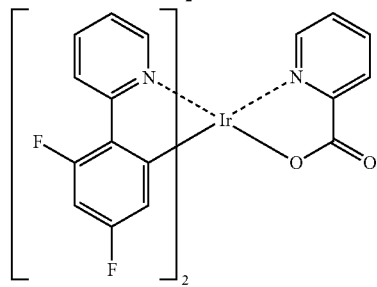

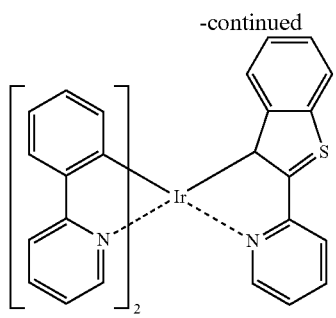
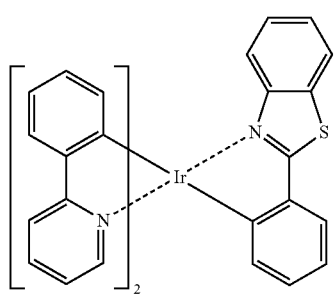
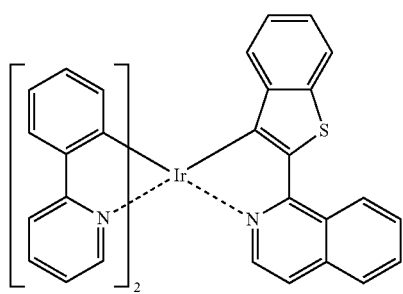
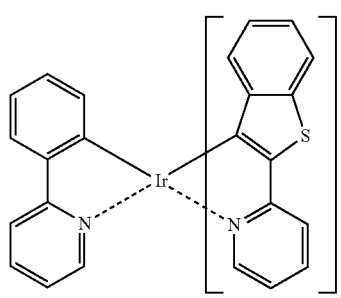
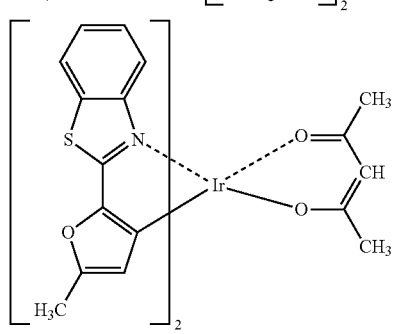
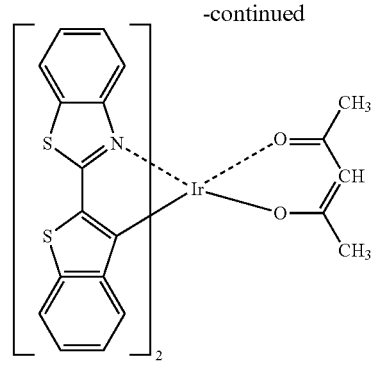
[Chem. 36]
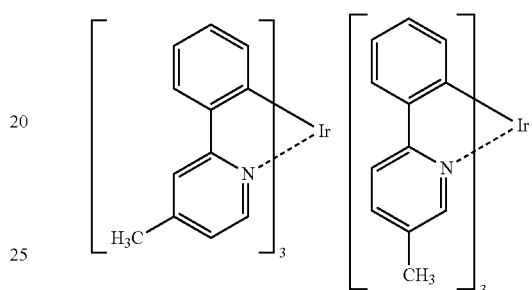
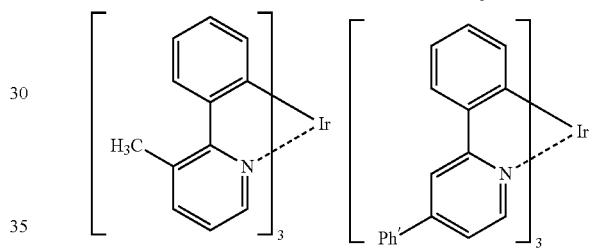
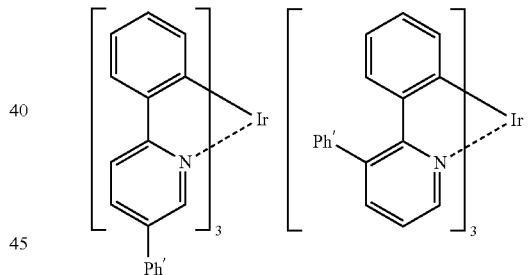
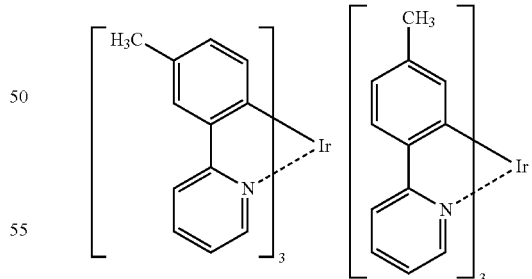
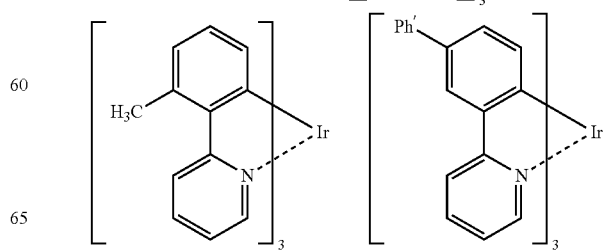

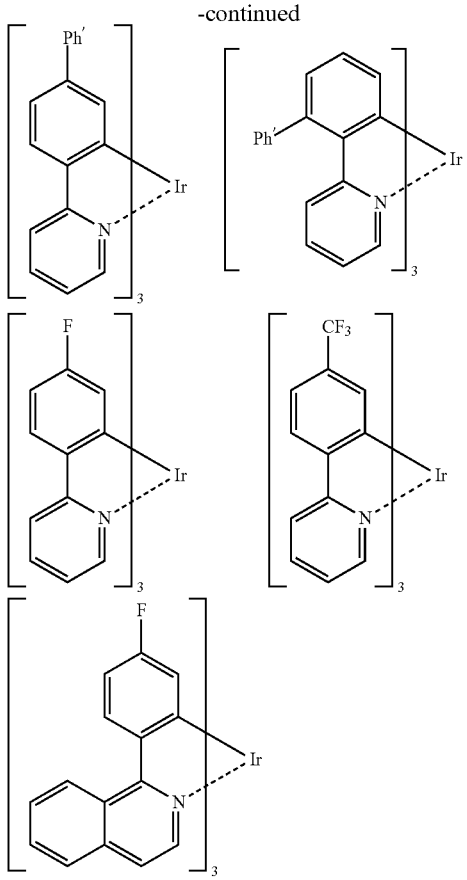

Especially preferred of the organometallic complexes represented by general formulae (V), (Va), (Vb), and (Vc) are: complexes having a 2-arylpyridine type ligand, i.e., 2-arylpyridine, as at least one of the ligands L and L'; such complexes in which one or more substituents have been bonded to the 2-arylpyridine; and such complexes in which the substituents have been bonded to each other to form a fused ring.

Furthermore, the compounds described in International Publication No. 2005/019373 are also usable.

Next, the compounds represented by general formula (VI) are explained.

$M^d$ in general formula (VI) represents a metal, and examples thereof include the metals enumerated above as metals selected from Groups 7 to 11 of the periodic table. Of these, suitable examples include ruthenium, rhodium, palladium, silver, rhenium, osmium, iridium, platinum, and gold. Preferred are divalent metals such as platinum and palladium.

In general formula (VI), $R^{92}$ and $R^{93}$ each independently represent a hydrogen atom, halogen atom, alkyl, aralkyl, alkenyl, cyano, amino, acyl, alkoxycarbonyl, carboxyl, alkoxy, alkylamino, aralkylamino, haloalkyl, hydroxy, aryloxy, aromatic hydrocarbon group, or aromatic heterocyclic group.

In the case where T is a carbon atom, $R^{94}$ and $R^{95}$ each independently represent a substituent examples of which are the same as in the case of $R^{92}$ and $R^{93}$. As stated above, $R^{94}$ and $R^{95}$ are absent when T is a nitrogen atom.

$R^{92}$ to $R^{95}$ may further have a substituent. The substituent in this case is not particularly limited, and the substituent can be any desired group.

Furthermore, $R^{92}$ to $R^{95}$ may be bonded to each other to form a ring, and this ring may further have any desired substituent.

Specific examples (T-1 and T-10 to T-15) of the organometallic complexes represented by general formula (VI) are shown below. However, the complexes should not be construed as being limited to the following example compounds, wherein Me represents methyl and Et represents ethyl.

[Chem. 37]

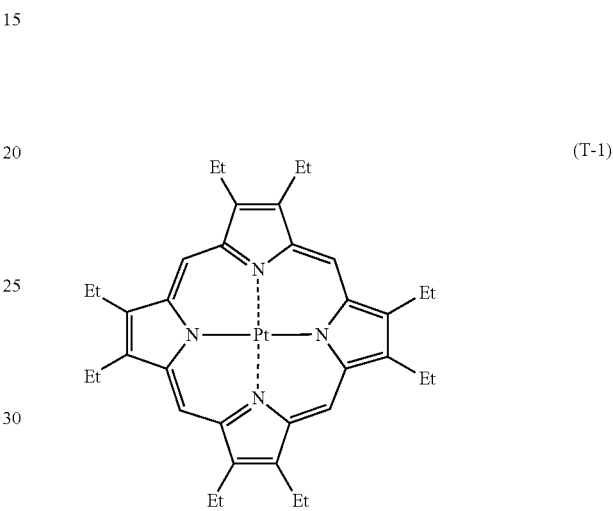

(T-1)

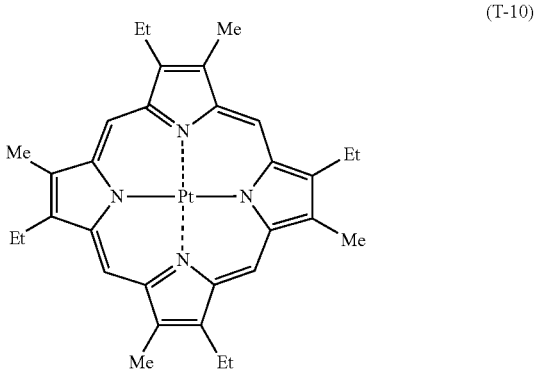

(T-10)

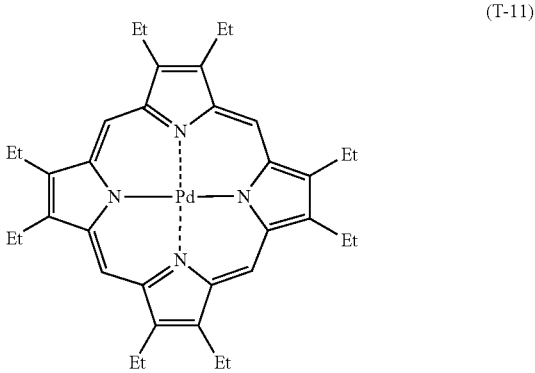

(T-11)

-continued

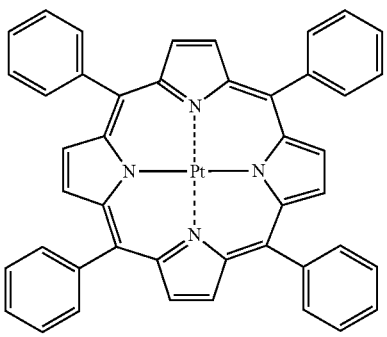

(T-12)

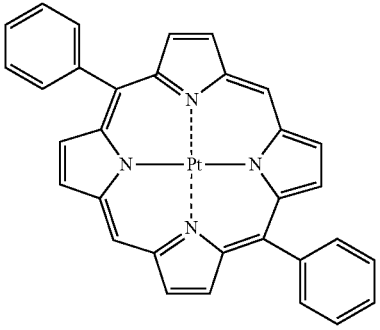

(T-13)

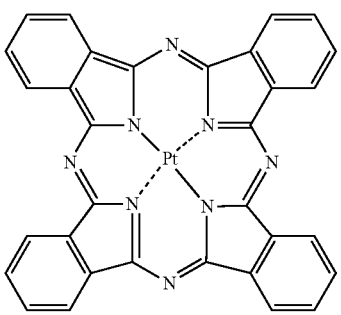

(T-14)

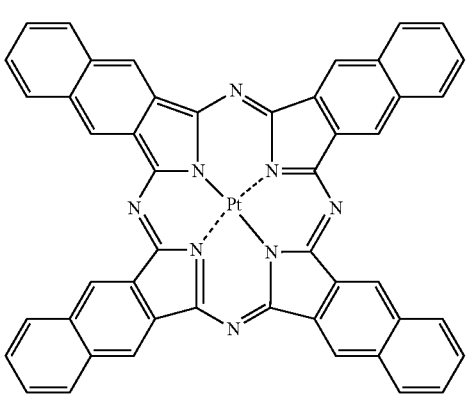

(T-15)

[3] Other Ingredients

The composition for charge transport film of the invention, in particular, the composition for charge transport film which is to be used as a composition for organic electroluminescent elements, may contain other various solvents according to need besides the solvent and luminescent material described above. Examples of the other solvents include amides, such as N,N-dimethylformamide and N,N-dimethylacetamide, and dimethyl sulfoxide. The composition may further contain various additives including a leveling agent and an antifoamer.

Furthermore, in order to prevent two or more layers from being compatible with each other when these layers are superposed by a wet film formation method, a photocurable resin or a thermosetting resin may be incorporated beforehand for the purpose of curing and insolubilizing any of the layers after formation thereof.

[4] Concentration of Materials in the Composition for Charge Transport Film and Incorporation Ratio Thereof.

In the composition for charge transport film, in particular, in the composition for organic electroluminescent elements, the concentration of solids such as the charge transport material, the luminescent material, and the ingredients which can be added according to need (e.g., a leveling agent) is as follows. The lower limit of the concentration thereof is generally preferably 0.01% by mass, more preferably 0.05% by mass, even more preferably 0.1% by mass, especially preferably 0.5% by mass, most preferably 1% by mass.

The upper limit thereof is generally preferably 80% by mass, more preferably 50% by mass, even more preferably 40% by mass, especially preferably 30% by mass, most preferably 20% by mass.

Regulating the concentration thereof to a value not lower than the lower limit makes it easy to form a thick film in thin-film formation. On the other hand, regulating the concentration thereof to a value not higher than the upper limit makes it easy to form a thin film.

In the composition for charge transport film of the invention, in particular, in the composition for organic electroluminescent elements, the content ratio by mass of the luminescent material to the charge transport material is as follows. The lower limit of the content ratio is generally preferably 0.1/99.9, more preferably 0.5/99.5, even more preferably 1/99, most preferably 2/98.

The upper limit thereof is generally preferably 50/50, more preferably 40/60, even more preferably 30/70, most preferably 20/80.

By regulating the mass ratio thereof to a value within that range, a sufficient luminescent efficiency can be obtained.

[5] Method for Preparing the Composition for Charge Transport Film

The composition for charge transport film of the invention, in particular, the composition for organic electroluminescent elements, can be prepared by dissolving solutes including the charge transport material, the luminescent material, and various additives which can be added according to need, such as a leveling agent and an antifoamer, in a suitable solvent.

It is usually preferred to dissolve the solutes while stirring the solution, in order to reduce the time period required for the dissolution step and to keep the concentration of the solutes in the composition constant. The dissolution step may be conducted at ordinary temperature. However, when the rate of dissolution is low, the solutes can be dissolved while heating the mixture. After completion of the dissolution step, a filtration step such as filtering may be conducted according to need.

[6] Properties, Etc. Of the Composition for Charge Transport Film (Water Concentration)

In the case where an organic electroluminescent element is produced through film formation by a wet film formation method using the composition for charge transport film of the invention (composition for organic electroluminescent elements), the presence of moisture in the composition for organic electroluminescent elements to be used results in the formation of a film which contains moisture and has impaired evenness. It is therefore preferred that the water content of the composition for charge transport film of the invention, in particular, the composition for organic electroluminescent elements, should be as low as possible.

In general, organic electroluminescent elements employ a large number of materials which deteriorate considerably by the action of moisture, e.g., the cathode. There is hence a possibility that when moisture is present in the composition for charge transport film, the film formed through drying might contain moisture remaining therein and the residual moisture might reduce the characteristics of the element. The presence of moisture in the composition is hence undesirable.

Specifically, the water content of the composition for charge transport film of the invention, in particular, the composition for organic electroluminescent elements, is generally preferably 1% by mass or lower, more preferably 0.1% by mass or lower, even more preferably 0.01% by mass or lower.

With respect to methods for determining the water concentration in the composition for charge transport film, the method described in Japanese Industrial Standards under "Method of Determining Moisture Content of Chemical Product" (JIS K0068: 2001) is preferred. For example, the composition can be analyzed by the Karl Fischer's reagent method (JIS K0211-1348) or the like.

(Evenness)

It is preferred that the composition for charge transport film of the invention, in particular, the composition for organic electroluminescent elements, should be in the state of a liquid which is even at ordinary temperature, from the standpoint of enhancing stability in a wet film formation process, e.g., stability in ejection from nozzles in film formation by ink-jet printing.

The term "state of a liquid which is even at ordinary temperature" means that the composition is a liquid constituted of an even phase and this composition contains no particulate ingredient having a particle diameter of 0.1 μm or more.

(Properties)

The viscosity at 25° C. of the composition for charge transport film of the invention, in particular, the composition for organic electroluminescent elements, is as follows. The lower limit thereof is generally preferably 2 mPa·s, more preferably 3 mPa·s, even more preferably 5 mPa·s. The upper limit thereof is generally preferably 1,000 mPa·s, more preferably 100 mPa·s, even more preferably 50 mPa·s.

The composition having a viscosity regulated so as to be not lower than the lower limit is less apt to arouse troubles such as, for example, excessive flow of the liquid film in a film formation step and the resultant unevenness of the coating surface and nozzle ejection failures in film formation by ink-jet printing. Furthermore, the composition for charge transport film, in particular, the composition for organic electroluminescent elements, that has a viscosity regulated so as to be not higher than the upper limit is less apt to cause nozzle clogging in film formation by ink-jet printing.

The surface tension at 20° C. of the composition for charge transport film of the invention, in particular, the composition for organic electroluminescent elements, is generally preferably less than 50 mN/m, more preferably less than 40 mN/m.

By regulating the surface tension thereof so as to be lower than the upper limit, the composition can be prevented from posing, for example, a problem that the liquid for film formation has reduced substrate-wetting properties, i.e., the liquid film has impaired leveling properties, and this is apt to result in a disordered film surface through drying.

The vapor pressure at 25° C. of the composition for charge transport film of the invention, in particular, the composition for organic electroluminescent elements, is generally preferably 50 mmHg or less, more preferably 10 mmHg or less, even more preferably 1 mmHg or less.

By regulating the vapor pressure thereof so as to be not higher than the upper limit, problems such as a change in solute concentration due to solvent vaporization can be prevented.

<Configuration of the Organic Electroluminescent Element>

The organic electroluminescent element of the invention is not particularly limited so long as the element includes a substrate and, formed thereover, a pair of electrodes and one or more organic layers, at least one of which contains the charge transport material of the invention.

The organic layers vary depending on the layer configuration of the organic electroluminescent element. However, examples thereof include a hole injection layer, a hole transport layer, a luminescent layer, a hole blocking layer, an electron transport layer, and an electron injection layer.

In the case where the organic electroluminescent element of the invention includes one organic layer, this means that the organic layer is a luminescent layer, and this luminescent layer has charge-transporting ability and contains the charge transport material of the invention.

On the other hand, in the case of an organic electroluminescent element including a plurality of organic layers, this element may be one in which at least one of the hole injection layer, hole transport layer, luminescent layer, hole blocking layer, electron transport layer, and electron injection layer contains the charge transport material of the invention.

The layer configuration of the organic layers in the organic electroluminescent element having a plurality of organic layers is not particularly limited so long as the element can luminesce. However, examples of the element include organic electroluminescent elements having the following layer configurations.

1) An organic electroluminescent element configured at least of a luminescent layer and an electron transport layer.
2) An organic electroluminescent element configured at least of a hole transport layer and a luminescent layer.
3) An organic electroluminescent element configured at least of a hole transport layer, a luminescent layer, and an electron transport layer.

A layer configuration of the organic electroluminescent element of the invention and general methods for forming the layers, etc. are explained below by reference to FIG. 1. Incidentally, for reasons of the convenience of illustration, the dimensional proportions in the drawing are not always the same as in the dimensional proportions explained below.

FIG. 1 is a diagrammatic sectional view illustrating one example of the organic electroluminescent element according to the invention. The organic electroluminescent element shown in FIG. 1 has a structure including a substrate 1 and, successively formed thereon, an anode 2, a hole injection layer 3, a hole transport layer 4, a luminescent layer 5, a hole blocking layer 6, an electron transport layer 7, an electron injection layer 8, and a cathode 9.

The term "wet film formation method" in the invention means a method in which a film is formed by a wet process or the like, such as, for example, spin coating, dip coating, die coating, bar coating, blade coating, roll coating, spray coating, capillary coating, ink-jet printing, screen printing, gravure printing, or flexographic printing.

Preferred of these film formation methods are spin coating, spray coating, and ink-jet printing. This is because these techniques suit with the liquid nature of the coating composition to be used for producing the organic electroluminescent element.

(Substrate)

The substrate 1 serves as the support of the organic electroluminescent element, and use may be made of a plate of quartz or glass, a metal plate, a metal foil, a plastic film or sheet, or the like.

Especially preferred are a glass plate and plates of transparent synthetic resins such as a polyester, polymethacrylate, polycarbonate, polysulfone, and the like.

In the case of using a synthetic-resin substrate, it is necessary to take account of gas barrier properties. In case where the substrate has too low gas barrier properties, there are cases where the surrounding air might pass through the substrate to deteriorate the organic electroluminescent element.

Consequently, one of preferred methods is to form a dense silicon oxide film or the like on at least one surface of a synthetic-resin substrate to ensure gas barrier properties.

(Anode)

The anode 2 serves to inject holes into layers located on the luminescent layer side. The anode 2 is usually constituted of a metal, e.g., aluminum, gold, silver, nickel, palladium, platinum, etc., a metal oxide, e.g., an indium and/or tin oxide, a metal halide, e.g., copper iodide, carbon black, a conductive polymer, e.g., poly(3-methylthiophene), polypyrrole, or polyaniline, or the like.

Usually, the anode 2 is frequently formed by sputtering, vacuum deposition, or the like. In the case where an anode 2 is to be formed using fine particles of a metal, e.g., silver, fine particles of copper iodide or the like, carbon black, fine particles of a conductive metal oxide, fine particles of a conductive polymer, or the like, use may be made of a method in which such fine particles are dispersed in an appropriate binder resin solution and the dispersion is applied to a substrate 1 to form an anode 2.

Furthermore, in the case of a conductive polymer, an anode 2 can be formed by directly forming a thin film on a substrate 1 through electrolytic polymerization or by applying the conductive polymer to a substrate 1 (*Appl. Phys. Lett.*, Vol. 60, p. 2711, 1992).

The anode 2 usually has a single-layer structure. However, the anode 2 can have a multilayer structure composed of a plurality of materials, according to need.

The thickness of the anode 2 varies depending on the degree of transparency required. When transparency is required, it is preferred that the anode 2 should be regulated so as to have a visible-light transmittance of generally preferably 60% or higher, more preferably 80% or higher. In this case, the thickness of the anode 2 is generally preferably 5 nm or more, more preferably 10 nm or more, and is generally preferably 1,000 nm or less, more preferably 500 nm or less.

When the anode 2 may be opaque, this anode 2 can have any desired thickness and may be identical with the substrate 1. Furthermore, it is possible to superpose a different conductive material on the anode 2.

It is preferred that the surface of the anode 2 should be subjected to an ultraviolet (UV)/ozone treatment or a treatment with an oxygen plasma or argon plasma for the purposes of removing impurities adherent to the anode 2 and regulating ionization potential to improve hole injection properties.

(Hole Injection Layer)

The hole injection layer 3 is a layer which transports holes from the anode 2 to the luminescent layer 5, and is usually formed on the anode 2.

Methods for forming the hole injection layer 3 according to the invention are not particularly limited, and either a vacuum deposition method or a wet film formation method may be used. However, from the standpoint of diminishing dark spots, it is preferred to form the hole injection layer 3 by a wet film formation method.

The thickness of the hole injection layer 3 is generally preferably 5 nm or more, more preferably 10 nm or more, and is generally preferably 1,000 nm or less, more preferably 500 nm or less.

<Formation of Hole Injection Layer by Wet Film Formation Method>

In the case where a hole injection layer 3 is to be formed by a wet process, materials for constituting the hole injection layer 3 are usually mixed with an appropriate solvent (solvent for hole injection layer) to prepare a composition for film formation (composition for hole injection layer formation).

Subsequently, this composition for hole injection layer formation is applied by a suitable technique to the layer (usually, the anode) which is to underlie the hole injection layer 3, and the resultant coating film is dried to thereby form a hole injection layer 3.

(Hole-Transporting Compound)

The composition for hole injection layer formation usually contains a hole-transporting compound, as a material for constituting the hole injection layer, and a solvent.

The hole-transporting compound may usually be a high-molecular compound such as a polymer or a low-molecular compound such as a monomer so long as the compound has hole-transporting properties and is for use in the hole injection layers of organic electroluminescent elements. It is, however, preferred that the hole-transporting compound should be a high-molecular compound.

From the standpoint of a barrier to charge injection from the anode 2 into the hole injection layer 3, it is preferred that the hole-transporting compound should be a compound having an ionization potential of 4.5 eV to 6.0 eV.

Examples of the hole-transporting compound include aromatic amine derivatives, phthalocyanine derivatives, porphyrin derivatives, oligothiophene derivatives, polythiophene derivatives, benzylphenyl derivatives, a compound including tertiary amines linked with a fluorene group, hydrazone derivatives, silazane derivatives, silanamine derivatives, phosphamine derivatives, quinacridone derivatives, polyaniline derivatives, polypyrrole derivatives, polyphenylenevinylene derivatives, polythienylenevinylene derivatives, polyquinoline derivatives, polyquinoxaline derivatives, and carbon.

Incidentally, the term "derivative" in the invention has the following meaning. In the case of an aromatic amine derivative, for example, that term includes the aromatic amine itself and compounds having the aromatic amine as the main framework, and these compounds may be polymers or monomers.

Any one of such hole-transporting compounds may be contained alone as a material for the hole injection layer 3, or two or more thereof may be contained as the material.

In the case where two or more hole-transporting compounds are contained, any desired combination of such compounds may be used. However, it is preferred to use one or more aromatic tertiary amine high-molecular compounds in combination with one or more other hole-transporting compounds.

Of the compounds shown above as examples, aromatic amine compounds are preferred from the standpoints of noncrystallinity and visible-light transmittance. In particular, aromatic tertiary amine compounds are preferred. The term aromatic tertiary amine compound means a compound having an aromatic tertiary amine structure, and includes a compound having a group derived from an aromatic tertiary amine.

The kind of aromatic tertiary amine compound is not particularly limited. However, a high-molecular compound (polymeric compound made up of consecutive repeating units) having a weight-average molecular weight of 1,000-1,000,000 is more preferred from the standpoint of even luminescence based on the effect of surface smoothing.

Preferred examples of the aromatic tertiary amine high-molecular compound include high-molecular compounds having a repeating unit represented by the following formula (VII).

[Chem. 38]

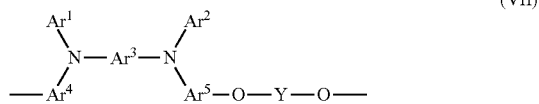

(VII)

In general formula (VII), $Ar^1$ and $Ar^2$ each independently represent an aromatic hydrocarbon group which may have a substituent or an aromatic heterocyclic group which may have a substituent. $Ar^3$ to $Ar^5$ each independently represent an aromatic hydrocarbon group which may have a substituent or an aromatic heterocyclic group which may have a substituent. Y represents a linking group selected from the following linking groups. Of $Ar^1$ to $Ar^5$, two groups bonded to the same nitrogen atom may be bonded to each other to form a ring.

[Chem. 39]

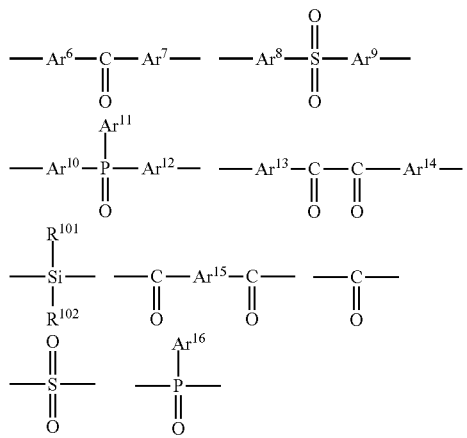

In the general formulae, $Ar^6$ to $Ar^{16}$ each independently represent an aromatic hydrocarbon group which may have a substituent or an aromatic heterocyclic group which may have a substituent. $R^{101}$ and $R^{102}$ each independently represent a hydrogen atom or any desired substituent.

The aromatic hydrocarbon groups and aromatic heterocyclic groups represented by $Ar^1$ to $Ar^{16}$ preferably are groups derived from any of a benzene ring, naphthalene ring, phenanthrene ring, thiophene ring, and pyridine ring, from the standpoints of the solubility, heat resistance, and suitability for hole injection and transport of the high-molecular compound. More preferred are groups derived from a benzene ring and a naphthalene ring.

The aromatic hydrocarbon groups and aromatic heterocyclic groups represented by $Ar^1$ to $Ar^{16}$ may have further substituents. The molecular weights of the substituents are generally preferably 400 or lower, more preferably 250 or lower.

Preferred examples of the substituents are alkyl groups, alkenyl groups, alkoxy groups, aromatic hydrocarbon groups, aromatic heterocyclic groups, and the like.

In the case where $R^{101}$ and $R^{102}$ are any desired substituents, examples of the substituents include alkyl groups, alkenyl groups, alkoxy groups, silyl group, siloxy group, aromatic hydrocarbon groups, and aromatic heterocyclic groups.

Specific examples of the aromatic tertiary amine high-molecular compounds having a repeating unit represented by formula (VII) include the compounds described in International Publication No. 2005/089024.

Also preferred as a hole-transporting compound is a conductive polymer (PEDOT/PSS) obtained by polymerizing 3,4-ethylenedioxythiophene, which is a derivative of polythiophene, in high-molecular poly(styrenesulfonic acid). This polymer may have been modified by capping the ends thereof with a methacrylate or the like.

The hole-transporting compound may be the crosslinkable polymer which will be described later in the section [Hole Transport Layer]. In the case of using the crosslinkable polymer, the same method for film formation may be used.

The concentration of the hole-transporting compound in the composition for hole injection layer formation is not limited unless the effects of the invention are considerably lessened. However, from the standpoint of the evenness of film thickness, the lower limit thereof is generally preferably 0.01% by mass, more preferably 0.1% by mass, even more preferably 0.5% by mass. The upper limit thereof is generally preferably 70% by mass, more preferably 60% by mass, even more preferably 50% by mass.

By regulating the concentration of the hole-transporting compound so as to be not higher than the upper limit, thickness unevenness can be prevented from occurring. By regulating the concentration thereof so as to be not lower than the lower limit, a hole injection layer having no defect is formed.

(Electron-Accepting Compound)

It is preferred that the composition for hole injection layer formation should contain an electron-accepting compound as a constituent material for the hole injection layer.

The electron-accepting compound preferably is a compound which has oxidizing ability and has the ability to accept one electron from the hole-transporting compound described above. Specifically, compounds having an electron affinity of 4 eV or higher are preferred, and compounds having an electron affinity of 5 eV or higher are more preferred.

Examples of such electron-accepting compounds include one or more compounds selected from the group consisting of triarylboron compounds, metal halides, Lewis acids, organic acids, onium salts, salts of an arylamine with a metal halide, and salts of an arylamine with a Lewis acid.

More specifically, examples thereof include onium salts substituted with organic groups, such as 4-isopropyl-4'-methyldiphenyliodonium tetrakis(pentafluorophenyl)borate and triphenylsulfonium tetrafluoroborate (International Publication No. 2005/089024); inorganic compounds having a high valence, such as iron(III) chloride (JP-A-11-251067) and ammonium peroxodisulfate; cyano compounds such as tetracyanoethylene; aromatic boron compounds such as tris (pentafluorophenyl)borane (JP-A-2003-31365); fullerene derivatives; iodine; and sulfonic acid ions such as poly (styrenesulfonic acid) ions; alkylbenzenesulfonic acid ions, and camphorsulfonic acid ions.

These electron-accepting compounds oxidize the hole-transporting compound and can thereby improve the conductivity of the hole injection layer.

In the hole injection layer or in the composition for hole injection layer formation, the content of the electron-accepting compound is generally preferably 0.1% by mole or higher, more preferably 1% by mole or higher, based on the hole-transporting compound. The content thereof is generally preferably 100% by mole or lower, more preferably 40% by mole or lower.

(Other Constituent Materials)

Besides the hole-transporting compound and electron-accepting compound described above, other ingredients may be incorporated as materials for the hole injection layer unless the incorporation thereof considerably lessens the effects of the invention.

Examples of the other ingredients include various luminescent materials, electron-transporting compounds, binder resins, and applicability improvers. One of such other ingredients may be used alone, or two or more thereof may be used in any desired combination and proportion.

(Solvent)

It is preferred that the solvent(s) contained in the composition for use in hole injection layer formation by a wet film formation method should include at least one solvent in which the constituent materials for the hole injection layer described above can dissolve.

The boiling point of this solvent is generally preferably 110° C. or higher, more preferably 140° C. or higher. In particular, a solvent having a boiling point which is 200° C. or higher and is 400° C. or lower, especially 300° C. or lower, is preferred.

By using a solvent having a boiling point not lower than the lower limit, a moderate drying rate is attained and satisfactory film quality is obtained. On the other hand, use of a solvent having a boiling point not higher than the higher limit eliminates the necessity of using a high temperature in the drying step and can prevent the drying from adversely affecting other layers or the substrate.

Examples of the solvent include ethers, esters, aromatic hydrocarbons, and amides. Dimethyl sulfoxide and the like are also usable. Specific examples of these solvents are as explained above.

One of these solvents may be used alone, or two or more thereof may be used in any desired combination and proportion.

(Methods of Film Formation)

After the composition for hole injection layer formation has been prepared, this composition is applied, by a wet process, to the layer (usually, the anode 2) which is located on the outer surface of the base, and the resultant coating film is dried. Thus, a hole injection layer 3 is formed.

The temperature to be used in the application step is preferably 10° C. or higher and is preferably 50° C. or lower, from the standpoint of preventing crystals from generating in the composition and thereby causing film defects.

The relative humidity in the application step is not limited unless the effects of the invention are considerably lessened. However, the relative humidity is generally preferably 0.01 ppm or higher and is generally preferably 80% or less.

After the application, the film of the composition for hole injection layer formation is dried usually by heating, etc. Examples of means for heating usable in the heating step include a clean oven, hot plate, infrared rays, halogen lamp heater, and irradiation with microwaves.

Of these, a clean oven and a hot plate are preferred from the standpoint of evenly heating the whole film.

With respect to heating temperature in the heating step, it is preferred to heat the film at a temperature not lower than the boiling point of the solvent used in the composition for hole injection layer formation, unless this drying considerably lessens the effects of the invention.

In the case where the solvent used for hole injection layer formation is a mixed solvent including two or more solvents, it is preferred to heat the film at a temperature not lower than the boiling point of at least one solvent contained in the mixed solvent. When an increase in the boiling point of solvents is taken into account, it is preferred that the temperature to be used in the heating step should be 120° C. to 410° C.

Heating period in the heating step is not limited so long as the heating temperature is not lower than the boiling point of the solvent of the composition for hole injection layer formation and the coating film is not sufficiently insolubilized. However, the heating period is preferably from 10 seconds to 180 minutes.

By regulating the heating period so as to be not longer than the upper limit, components of other layers can be prevented from diffusing. By regulating the heating period so as to be not shorter than the lower limit, the hole injection layer can be prevented from being inhomogeneous. Heating may be conducted two times.

<Formation of Hole Injection Layer by Vacuum Deposition>

In the case where a hole injection layer 3 is to be formed by vacuum deposition, one or more constituent materials (e.g., the hole-transporting compound and electron-accepting compound described above) for the hole injection layer 3 are placed in one or more crucibles disposed within a vacuum vessel (when two or more materials are used, the materials are placed in respective crucibles). The inside of the vacuum vessel is evacuated with an appropriate vacuum pump to about $10^{-4}$ Pa, and the crucibles are then heated (when two or more materials are used, the respective crucibles are heated) to vaporize the materials while controlling vaporization amount (when two or more materials are used, the materials are vaporized while independently controlling the amounts of the materials being vaporized) to form a hole injection layer 3 on the anode 2 of a substrate placed so as to face the crucibles.

Incidentally, in the case where two or more materials are used, use may be made of a method in which a mixture of these materials is placed in a crucible, heated, and vaporized to form a hole injection layer 3.

The degree of vacuum during the deposition is not limited unless the effects of the invention are considerably lessened. However, the degree of vacuum is generally preferably $0.1 \times 10^{-6}$ Torr ($0.13 \times 10^{-4}$ Pa) or higher, and is generally preferably $9.0 \times 10^{-6}$ Torr ($12.0 \times 10^{-4}$ Pa) or lower.

The rate of deposition is not limited unless the effects of the invention are considerably lessened. However, the rate of deposition is generally preferably 0.1 Å/sec or higher, and is generally preferably 5.0 Å/sec or lower.

Film formation temperature during the deposition is not limited unless the effects of the invention are considerably lessened. However, the temperature is preferably 10° C. or higher and is preferably 50° C. or lower.

[Hole Transport Layer]

Methods for forming the hole transport layer 4 according to the invention are not particularly limited, and either a vacuum deposition method or a wet film formation method may be used. However, from the standpoint of diminishing dark spots, it is preferred to form the hole transport layer 4 by a wet film formation method.

In the case where there is a hole injection layer, a hole transport layer 4 can be formed on the hole injection layer 3. When there is no hole injection layer 3, then a hole transport layer 4 can be formed on the anode 2. The organic electroluminescent element of the invention may have a configuration in which the hole transport layer has been omitted.

For forming the hole transport layer 4, it is preferred to use a material which has high hole-transporting properties and can efficiently transport injected holes. In order for a material to have such properties, it is preferred that the material should have a low ionization potential, be highly transparent to visible light, and have a high hole mobility and excellent stability, and that impurities functioning as a trap do not generate during production of the material or during use.

Furthermore, since the hole transport layer 4 is in contact with the luminescent layer 5 in many cases, it is preferred that the material constituting the hole transport layer 4 should not function to cause extinction of luminescence from the luminescent layer 5 or to form an exciplex with the luminescent layer 5 and thereby reduce efficiency.

As such a material for the hole transport layer 4, use may be made of materials which have conventionally been used as constituent materials for hole transport layers. Examples thereof include the materials enumerated above as examples of the hole-transporting compound to be used in the hole injection layer 3 described above.

Examples thereof further include arylamine derivatives, fluorene derivatives, Spiro derivatives, carbazole derivatives, pyridine derivatives, pyrazine derivatives, pyrimidine derivatives, triazine derivatives, quinoline derivatives, phenanthroline derivatives, phthalocyanine derivatives, porphyrin derivatives, silole derivatives, oligothiophene derivatives, fused-ring aromatic derivatives, and metal complexes.

Examples thereof furthermore include polyvinylcarbazole derivatives, polyarylamine derivatives, polyvinyltriphenylamine derivatives, polyfluorene derivatives, polyarylene derivatives, poly(arylene ether sulfone) derivatives containing tetraphenylbenzidine, polyarylenevinylene derivatives, polysiloxane derivatives, polythiophene derivatives, and poly(p-phenylenevinylene) derivatives.

These derivatives may be any of alternating copolymers, random polymers, block polymers, and graft copolymers. Furthermore, the derivatives may be high-molecular compounds in which the main chain has one or more branches and which have three or more ends, or may be the so-called dendrimers.

Preferred of those are polyarylamine derivatives and polyarylene derivatives.

The polyarylamine derivatives preferably are polymers containing a repeating unit represented by the following general formula (VIII). Especially preferred are polymers each comprising repeating units represented by the following general formula (VIII). In this case, such a polymer may be one in which the repeating units differ in $Ar^a$ or $Ar^b$.

[Chem. 40]

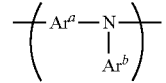

(VIII)

In general formula (VIII), $Ar^a$ and $Ar^b$ each independently represent an aromatic hydrocarbon group or aromatic heterocyclic group which may have a substituent.

Examples of the aromatic hydrocarbon group which may have a substituent include groups derived from 6-membered monocycles or di- to pentacyclic fused rings, such as a benzene ring, naphthalene ring, anthracene ring, phenanthrene ring, perylene ring, tetracene ring, pyrene ring, benzpyrene ring, chrysene ring, triphenylene ring, acenaphthene ring, fluoranthene ring, and fluorene ring. Examples thereof further include groups each made up of two or more rings selected from these rings and linked together through a direct bond.

Examples of the aromatic heterocyclic group which may have a substituent include groups derived from 5- or 6-membered monocycles or di- to tetracyclic fused rings, such as a furan ring, benzofuran ring, thiophene ring, benzothiophene ring, pyrrole ring, pyrazole ring, imidazole ring, oxadiazole ring, indole ring, carbazole ring, pyrroloimidazole ring, pyrrolopyrazole ring, pyrrolopyrrole ring, thienopyrrole ring, thienothiophene ring, furopyrrole ring, furofuran ring, thienofuran ring, benzisoxazole ring, benzisothiazole ring, benzimidazole ring, pyridine ring, pyrazine ring, pyridazine ring, pyrimidine ring, triazine ring, quinoline ring, isoquinoline ring, cinnoline ring, quinoxaline ring, phenanthridine ring, benzimidazole ring, perimidine ring, quinazoline ring, quinazolinone ring, and azulene ring. Examples thereof further include groups each made up of two or more rings selected from these rings and linked together through a direct bond.

From the standpoints of solubility and heat resistance, it is preferred that $Ar^a$ and $Ar^b$ should each independently be a group derived from a ring selected from the group consisting of a benzene ring, naphthalene ring, anthracene ring, phenanthrene ring, triphenylene ring, pyrene ring, thiophene ring, pyridine ring, and fluorene ring, or be a group made up of two or more benzene rings linked together [e.g., a biphenyl group (biphenylene group) and a terphenyl group (terphenylene group)].

Preferred of these are a group derived from a benzene ring (phenyl group), a group made up of two benzene rings linked together (biphenyl group), and a group derived from a fluorene ring (fluorenyl group).

Examples of the substituents which may be possessed by the aromatic hydrocarbon groups and aromatic heterocyclic groups represented by $Ar^a$ and $Ar^b$ include alkyl groups, alkenyl groups, alkynyl groups, alkoxy groups, aryloxy groups, alkoxycarbonyl groups, dialkylamino groups, diarylamino groups, acyl groups, halogen atoms, haloalkyl groups, alkylthio groups, arylthio groups, silyl, siloxy, cyano, aromatic hydrocarbon ring groups, and aromatic heterocyclic groups.

Examples of the polyarylene derivatives include polymers having a repeating unit including an arylene group, such as an aromatic hydrocarbon group or an aromatic heterocyclic group, that may have substituents shown above as examples with regard to the Ar$^a$ and Ar$^b$.

It is preferred that the polyarylene derivatives should be polymers having repeating units of the following general formula (IX-1) and/or the following formula (IX-2).

[Chem. 41]

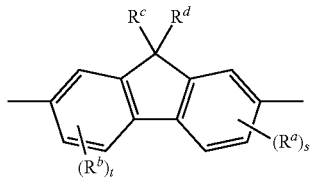

(IX-1)

In general formula (IX-1), R$^a$, R$^b$, R$^c$, and R$^d$ each independently represent an alkyl group, alkoxy group, phenylalkyl group, phenylalkoxy group, phenyl group, phenoxy group, alkylphenyl group, alkoxyphenyl group, alkylcarbonyl group, alkoxycarbonyl group, or carboxy group. Symbols t and s each independently represent an integer of 0-3. When t or s is 2 or larger, then the multiple R$^a$s or R$^b$s contained in each molecule may be the same or different, and adjacent R$^a$s or R$^b$s may have been bonded to each other to form a ring.

[Chem. 42]

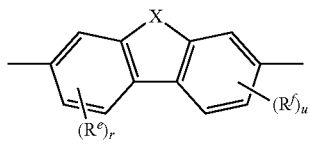

(IX-2)

In general formula (IX-2), R$^e$ and R$^f$ each independently have the same meaning as the R$^a$, R$^b$, R$^c$, or R$^d$ contained in general formula (IX-1). Symbols r and u each independently represent an integer of 0-3. When r or u is 2 or larger, then the multiple R$^e$s and R$^f$s contained in each molecule may be the same or different, and adjacent R$^e$s or R$^f$s may have been bonded to each other to form a ring. X represents an atom or a group of atoms as a component of the five-membered ring or six-membered ring.

Examples of X include —O—, —BR$^{103}$—, —NR$^{103}$—, —SiR$^{103}_2$—, —PR$^{103}$—, —SR$^{103}$—, —CR$^{103}_2$—, and a group made up of these atoms or groups bonded together. R$^{103}$ represents a hydrogen atom or any desired organic group. The term "organic group" in the invention means a group containing at least one carbon atom.

It is also preferred that the polyarylene derivatives should have a repeating unit represented by the following general formula (IX-3) besides the repeating units of general formula (IX-1) and/or general formula (IX-2).

[Chem. 43]

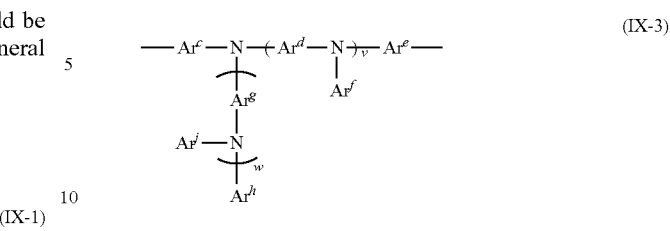

(IX-3)

In general formula (IX-3), Ar$^c$ to Ar$^j$ each independently represent an aromatic hydrocarbon group or aromatic heterocyclic group which may have a substituent. Symbols v and w each independently represent 0 or 1.

Examples of Ar$^c$ to Ar$^j$ are the same as the examples of the Ar$^a$ and Ar$^b$ contained in general formula (VIII).

Examples of general formulae (IX-1) to (IX-3), examples of the polyarylene derivatives, etc. include the examples given in JP-A-2008-98619.

In the case where the hole transport layer 4 is to be formed by a wet film formation method, a composition for hole transport layer formation is prepared, subsequently formed into a film by a wet process, and then heated and dried, as in the formation of the hole injection layer 3.

The composition for hole transport layer formation contains a solvent besides the hole-transporting compound described above. The solvent to be used may be the same as the solvent used in the composition for hole injection layer formation. Film formation conditions, heating/drying conditions, and the like also are the same as in the formation of the hole injection layer 3.

Also in the case where a hole transport layer is to be formed by a vacuum deposition method, conditions for the deposition and other conditions may be the same as in the formation of the hole injection layer 3.

The hole transport layer 4 may contain various luminescent materials, electron-transporting compounds, binder resins, applicability improvers, etc., besides the hole-transporting compound.

The hole transport layer 4 may also be a layer formed by crosslinking a crosslinkable compound. The crosslinkable compound is a compound which has a crosslinkable group and forms a network high-molecular compound through crosslinking.

Examples of the crosslinkable group include groups derived from cyclic ethers, such as oxetane and epoxy; groups derived from an unsaturated double bond, such as vinyl, trifluorovinyl, styryl, acryloyl, methacryloyl, and cinnamoyl; and groups derived from benzocyclobutene.

The crosslinkable compound may be any of a monomer, an oligomer, and a polymer. One crosslinkable compound may be contained alone, or two or more crosslinkable compounds may be contained in any desired combination and proportion.

As the crosslinkable compound, it is preferred to use a hole-transporting compound having a crosslinkable group. Examples of the hole-transporting compound include nitrogen-containing aromatic compound derivatives such as pyridine derivatives, pyrazine derivatives, pyrimidine derivatives, triazine derivatives, quinoline derivatives, phenanthroline derivatives, carbazole derivatives, phthalocyanine derivatives, and porphyrin derivatives, triphenylamine derivatives, silole derivatives, oligothiophene derivatives, fused-ring aromatic derivatives, and metal complexes.

Preferred of these are nitrogen-containing aromatic derivatives such as pyridine derivatives, pyrazine derivatives, pyrimidine derivatives, triazine derivatives, quinoline derivatives, phenanthroline derivatives, and carbazole derivatives, triphenylamine derivatives, silole derivatives, fused-ring aromatic derivatives, and metal complexes. In particular, triphenylamine derivatives are preferred.

Examples of the crosslinkable compound include those hole-transporting compounds in which a crosslinkable group has been bonded to the main chain or a side chain thereof. It is especially preferred that a crosslinkable group should have been bonded to the main chain through a linking group such as, for example, an alkylene group.

Furthermore, it is especially preferred that the hole-transporting compound should be a polymer containing a repeating unit having a crosslinkable group, and should be a polymer having a repeating unit represented by any of general formulae (VIII) and (IX-1) to (IX-3) to which a crosslinkable group has been bonded either directly or through a linking group.

For forming a hole transport layer 4 through crosslinking of a crosslinkable compound, use is generally made of a method which includes dissolving or dispersing the crosslinkable compound in a solvent to prepare a composition for hole transport layer formation, forming this composition into a film by a wet process, and crosslinking the crosslinkable compound.

The composition for hole transport layer formation may contain an additive which accelerates the crosslinking reaction, besides the crosslinkable compound. Examples of the additive which accelerates the crosslinking reaction include polymerization initiators such as alkylphenone compounds, acylphosphine oxide compounds, metallocene compounds, oxime ester compounds, azo compounds, and onium salts; polymerization accelerators; and photosensitizers such as fused-ring hydrocarbons, porphyrin compounds, and diaryl ketone compounds.

The composition may further contain an applicability improver such as a leveling agent or an antifoamer, an electron-accepting compound, a binder resin, and the like.

The content of the crosslinkable compound in the composition for hole transport layer formation is generally preferably 0.01% by mass or higher, more preferably 0.05% by mass or higher, even more preferably 0.1% by mass or higher. The content thereof is generally preferably 50% by weight or lower, more preferably 20% by weight or lower, even more preferably 10% by weight or lower.

It is preferred that the composition for hole transport layer formation which contains a crosslinkable compound in that concentration should be applied to the layer to be an underlying layer (usually, the hole injection layer 3) to form a film and the crosslinkable compound should be thereafter crosslinked by means of heating and/or irradiation with actinic energy, such as light, to thereby form a network high-molecular compound.

Conditions including temperature and humidity for the film formation are the same as in the wet film formation for forming the hole injection layer 3.

Techniques for heating to be conducted after film formation are not particularly limited. With respect to heating temperature conditions, the temperature is generally preferably 120° C. or higher and is more preferably 400° C. or lower.

The heating period is generally preferably 1 minute or longer and is more preferably 24 hours or shorter.

Although methods for heating are not particularly limited, use may be made, for example, of a method in which the multilayer structure having the layer formed is put on a hot plate or heated in an oven. For example, use can be made of conditions under which the multilayer structure is heated on a hot plate at 120° C. or higher for 1 minute or longer.

In the case of irradiation with actinic energy such as light, examples of methods therefor include a method in which an ultraviolet, visible, or infrared light source, e.g., an ultra-high-pressure mercury lamp, high-pressure mercury lamp, halogen lamp, or infrared lamp, is used to directly irradiate the layer and a method in which a mask aligner or conveyor type irradiator that has any of those light sources built therein is used to irradiate the layer.

With respect to irradiation with actinic energy other than light, examples of methods therefor include a method in which an apparatus for irradiating with microwaves generated by a magnetron, i.e., the so-called electronic oven, is used for the irradiation.

With respect to irradiation period, it is preferred to set conditions necessary for reducing the solubility of the film. However, the irradiation period is generally preferably 0.1 sec or longer and is more preferably 10 hours or shorter.

Heating and irradiation with actinic energy, e.g., light, may be conducted alone or in combination. In the case where heating and the irradiation are conducted in combination, the sequence of performing these is not particularly limited.

The thickness of the hole transport layer 4 thus formed is generally preferably 5 nm or more, more preferably 10 nm or more, and is generally preferably 300 nm or less, more preferably 100 nm or less.

[Luminescent Layer]

A luminescent layer 5 is usually disposed on the hole injection layer 3. The luminescent layer 5, for example, is a layer containing the luminescent material described above. The luminescent layer 5 is a layer which, between the electrodes placed in an electric field, is excited by recombination of holes injected from the anode 2 through the hole injection layer 3 with electrons injected from the cathode 9 through the electron transport layer 7 and which thus functions as the main luminescent source.

It is preferred that the luminescent layer 5 should contain a luminescent material (dopant) and one or more host materials. It is more preferred that the luminescent layer 5 should contain the charge transport material of the invention as a host material.

Although the luminescent layer 5 may be formed by a vacuum deposition method, it is especially preferred that the luminescent layer 5 should be a layer formed from the composition for organic electroluminescent elements of the invention by a wet film formation method.

As stated above, the wet film formation method is a technique for forming a film from a solvent-containing composition by spin coating, spray coating, dip coating, die coating, flexographic printing, screen printing, ink-jet printing, etc.

The luminescent layer 5 may contain other materials or ingredients so long as the performance of the invention is not impaired thereby.

In general, organic electroluminescent elements having a smaller thickness of films interposed between the electrodes have a stronger effective electric field when the same materials are used. As a result, a larger amount of current is injected and the operating voltage decreases. Consequently, the smaller the total thickness of films interposed between the electrodes, the lower the operating voltage of the organic electroluminescent element. However, too small thicknesses thereof may result in short-circuiting due to projections attributable to an electrode, e.g., ITO. Some degree of film thickness is therefore necessary.

In the invention, when the organic electroluminescent element has organic layers such as the hole injection layer 3 and the electron transport layer 7 which will be described later, besides the luminescent layer 5, then the total thickness of the luminescent layer 5 and the other organic layers including the hole injection layer 3 and the electron transport layer 7 is generally preferably 30 nm or more, more preferably 50 nm or more, even more preferably 100 nm or more. The upper limit of the total thickness thereof is generally preferably 1,000 nm, more preferably 500 nm, even more preferably 300 nm.

In the case where a layer other than the luminescent layer 5, e.g., the hole injection layer 3 or the electron injection layer 8 which will be described later, has high conductivity, an increased amount of charges are injected into the luminescent layer 5. It is therefore possible to lower the operating voltage while maintaining some degree of total film thickness, by increasing the thickness of, for example, the hole injection layer 3 and reducing the thickness of the luminescent layer 5.

Consequently, the thickness of the luminescent layer 5 is generally preferably 10 nm or more, more preferably 20 nm or more. The thickness thereof is generally preferably 300 nm or less, more preferably 200 nm or less.

In the case where the element of the invention has the luminescent layer 5 as the only layer interposed between the anode and the cathode, the thickness of this luminescent layer 5 is generally preferably 30 nm or more, more preferably 50 nm or more. The thickness thereof is generally preferably 500 nm or less, more preferably 300 nm or less.

[Hole Blocking Layer]

A hole blocking layer 6 may be disposed between the luminescent layer 5 and the electron injection layer 8 which will be described later. The hole blocking layer 6 is a layer superposed on the luminescent layer 5 so as to be in contact with that interface of the luminescent layer 5 which faces the cathode 9.

This hole blocking layer 6 serves to block holes sent from the anode 2 and prevent the holes from reaching the cathode 9, and further serves to efficiently transport, toward the luminescent layer 5, electrons injected from the cathode 9.

Examples of properties which are required of the material constituting the hole blocking layer 6 include a high electron mobility and a low hole mobility, a large energy gap (difference between HOMO and LUMO), and a high excited-triplet level (T1).

Examples of materials for the hole blocking layer which satisfy such requirements include metal complexes such as mixed-ligand complexes, e.g., bis(2-methyl-8-quinolinolato)(phenolato)aluminum and bis(2-methyl-8-quinolinolato)(triphenylsilanolato)aluminum, and dinuclear metal complexes such as bis(2-methyl-8-quinolato)aluminum-µ-oxobis(2-methyl-8-quinolilato)aluminum, styryl compounds such as distyrylbiphenyl derivatives (JP-A-11-242996), triazole derivatives such as 3-(4-biphenylyl)-4-phenyl-5-(4-tert-butylphenyl)-1,2,4-triazole (JP-A-7-41759), and phenanthroline derivatives such as bathocuproine (JP-A-10-79297).

Furthermore, the compound having at least one pyridine ring substituted in the 2-, 4-, and 6-positions which is described in International Publication No. 2005/022962 is also preferred as a material for the hole blocking layer 6.

One material only may be used for forming the hole blocking layer 6, or two or more materials may be used for forming the layer 6 in any desired combination and proportion.

Methods for forming the hole blocking layer 6 are not limited. Consequently, the hole blocking layer 6 can be formed by a wet film formation method, vapor deposition method, or another method.

The thickness of the hole blocking layer 6 is not limited unless the effects of the invention are considerably lessened. However, the thickness thereof is generally preferably 0.3 nm or more, more preferably 0.5 nm or more, and is generally preferably 100 nm or less, more preferably 50 nm or less.

[Electron Transport Layer]

An electron transport layer 7 may be disposed between the luminescent layer 5 and the electron injection layer 8 which will be described later.

The electron transport layer 7 is disposed for the purpose of further improving the luminescent efficiency of the element, and is constituted of one or more compounds which, between the electrodes placed in an electric field, can efficiently transport, toward the luminescent layer 5, electrons injected from the cathode 9.

As electron-transporting compounds for the electron transport layer 7, use is generally made of compounds which attain a high efficiency of electron injection from the cathode 9 or electron injection layer 8 and which have a high electron mobility and can efficiently transport injected electrons.

Examples of compounds satisfying such requirements include metal complexes such as an aluminum complex of 8-hydroxyquinoline (JP-A-59-194393), metal complexes of 10-hydroxybenzo[h]quinoline, oxadiazole derivatives, distyrylbiphenyl derivatives, silole derivatives, 3-hydroxyflavone metal complexes, 5-hydroxyflavone metal complexes, benzoxazole metal complexes, benzthiazole metal complexes, trisbenzimidazolylbenzene (U.S. Pat. No. 5,645,948), quinoxaline compounds (JP-A-6-207169), phenanthroline derivatives (JP-A-5-331459), 2-t-butyl-9,10-N,N'-dicyanoanthraquinonediimine, n-type amorphous silicon hydride carbide, n-type zinc sulfide, and n-type zinc selenide.

One material only may be used for forming the electron transport layer 7, or two or more materials may be used for forming the layer 7 in any desired combination and proportion.

Methods for forming the electron transport layer 7 are not limited. Consequently, the electron transport layer 7 can be formed by a wet film formation method, vapor deposition method, or another method.

The thickness of the electron transport layer 7 is not limited unless the effects of the invention are considerably lessened. However, the thickness thereof is generally preferably 1 nm or more, more preferably 5 nm or more, and is generally preferably 300 nm or less, more preferably 100 nm or less.

[Electron Injection Layer]

The electron injection layer 8 serves to efficiency inject, into the luminescent layer 5, electrons injected from the cathode 9. From the standpoint of efficiently injecting electrons, it is preferred that the material constituting the electron injection layer 8 should be a metal having a low work function.

Examples thereof include alkali metals such as sodium and cesium and alkaline earth metals such as barium and calcium. The thickness of the layer is generally preferably 0.1 nm or more and is more preferably 5 nm or less.

Furthermore, doping of an organic electron transport compound represented by a nitrogen-containing heterocyclic compound, e.g., bathophenanthroline, or a metal complex, e.g., an aluminum complex of 8-hydroxyquinoline, with an alkali metal such as sodium, potassium, cesium, lithium, or rubidium (described in JP-A-10-270171, JP-A-2002-100478, JP-A-2002-100482, etc.) is preferred because this doping improves suitability for electron injection and transport and enables the layer to combine the improved suitability and excellent film quality.

The thickness of the film in this case is generally preferably 5 nm or more, more preferably 10 nm or more, and is generally preferably 200 nm or less, more preferably 100 nm or less.

One material only may be used for forming the electron injection layer 8, or two or more materials may be used for forming the layer 8 in any desired combination and proportion.

Methods for forming the electron injection layer 8 are not limited. Consequently, the electron injection layer 8 can be formed by a wet film formation method, vapor deposition method, and other methods.

[Cathode]

The cathode 9 serves to inject electrons into a layer located on the luminescent layer 5 side (e.g., the electron injection layer 8 or the luminescent layer 5).

As the material of the cathode 9, the materials usable for the anode 2 can be used. However, metals having a low work function are preferred from the standpoint of efficiently injecting electrons.

Examples thereof include suitable metals such as tin, magnesium, indium, calcium, aluminum, and silver and alloys of these. Specific examples thereof include electrodes of alloys having a low work function, such as magnesium-silver alloys, magnesium-indium alloys, and aluminum-lithium alloys.

One material only may be used for forming the cathode 9, or two or more materials may be used for forming the cathode 9 in any desired combination and proportion.

The thickness of the cathode 9 is generally the same as that of the anode 2.

For the purpose of protecting the cathode 9 made of a metal having a low work function, a layer of a metal which has a high work function and is stable to the air may be formed on the cathode 9. This layer formation is preferred because the stability of the element is enhanced thereby.

For that purpose, metals such as, for example, aluminum, silver, copper, nickel, chromium, gold, and platinum are used. One of these materials may be used alone, or two or more thereof may be used in any desired combination and proportion.

[Other Layers]

The organic electroluminescent element according to the invention may have other configurations unless the configurations depart from the spirit of the invention. For example, unless the performance of the element is impaired, the element may have any desired layer other than the layers described above, between the anode 2 and the cathode 9, or any layer may have been omitted.

[Electron Blocking Layer]

Examples of the layers which may be possessed include an electron blocking layer.

The electron blocking layer is disposed between the hole injection layer 3 or hole transport layer 4 and the luminescent layer 5. The electron blocking layer serves to block electrons sent from the luminescent layer 5 and prevent the electrodes from reaching the hole injection layer 3. The electron blocking layer thus functions to heighten the probability of recombination of holes with electrons within the luminescent layer 5 and to confine the resultant excitons in the luminescent layer 5. The electron blocking layer further has the function of efficiently transporting, toward the luminescent layer 5, holes injected from the hole injection layer 3.

To dispose the electron blocking layer is effective especially when a phosphorescent material or a blue luminescent material is used as a luminescent material.

Examples of properties which are required of the electron blocking layer include high hole-transporting properties, a large energy gap (difference between HOMO and LUMO), and a high excited-triplet level (T1).

Furthermore, in the invention, when the luminescent layer 5 is to be formed by a wet film formation method, the electron blocking layer also is required to have suitability for the wet film formation. Examples of materials usable for forming such an electron blocking layer include copolymers of dioctylfluorene and triphenylamine which are represented by F8-TFB (International Publication No. 2004/084260).

One material only may be used for forming the electron blocking layer, or two or more materials may be used for forming the layer in any desired combination and proportion.

Methods for forming the electron blocking layer are not limited. Consequently, the electron blocking layer can be formed by a wet film formation method, vapor deposition method, or another method.

Furthermore, to interpose an ultrathin insulating film (0.1-5 nm) made of, for example, lithium fluoride (LiF), magnesium fluoride ($MgF_2$), lithium oxide ($Li_2O$), and cesium(II) carbonate ($CsCO_3$) at the interface between the cathode 9 and the luminescent layer 5 or electron transport layer 7 is an effective technique for improving the efficiency of the element (see, for example, *Applied Physics Letters*, Vol. 70, p. 152, 1997; JP-A-10-74586; *IEEE Transactions on Electron Devices*, Vol. 44, p. 1245, 1997; and *SID 04 Digest*, p. 154).

The configuration of the organic electroluminescent element of the invention should not be construed as being limited to the configuration described above, and the sequence of layer superposition can be changed. Specifically, the element may have a structure including a substrate 1 and, superposed thereon in the following order, a cathode 9, electron injection layer 8, electron transport layer 7, hole blocking layer 6, luminescent layer 5, hole transport layer 4, hole injection layer 3, and anode 2.

It is also possible to constitute an organic electroluminescent element according to the invention by superposing the constituent elements other than the substrate between two substrates, at least one of which is transparent.

A structure composed of a stack of stages each composed of constituent elements other than substrates (luminescent units) (i.e., a structure composed of a plurality of stacked luminescent units) is also possible.

In this case, when a carrier generation layer (CGL) containing, for example, vanadium pentoxide ($V_2O_5$) is disposed in place of the interfacial layers located between the stages (i.e., between the luminescent units) (when the anode is ITO and the cathode is aluminum, the interfacial layers are these two layers), then the barrier between the stages is reduced. This configuration is more preferred from the standpoints of luminescent efficiency and operating voltage.

Furthermore, the organic electroluminescent element according to the invention may be configured so as to be a single organic electroluminescent element, or may be applied to a configuration in which a plurality of organic electroluminescent elements have been disposed in an array arrangement. The organic electroluminescent element may also be applied to a configuration in which anodes and cathodes have been disposed in an X-Y matrix arrangement.

Each of the layers described above may contain ingredients other than those described above, unless the effects of the invention are considerably lessened thereby.

<Organic EL Display and Organic EL Lighting>

The organic EL display and organic EL lighting of the invention are equipped with the organic electroluminescent element of the invention described above. The types and structures of the organic EL display and organic EL lighting of the invention are not particularly limited, and can be fabricated using the organic electroluminescent element of the invention according to ordinary methods.

For example, the organic EL display and organic EL lighting of the invention can be formed by the methods described in *Yūki EL Dispurei* (Ohmsha, Ltd., published on Aug. 20, 2004, written by TOKITO Shizuo, ADACHI Chihaya, and MURATA Hideyuki).

EXAMPLES

The invention will be explained below in more detail by reference to Examples. However, the invention should not be construed as being limited to the following Examples, and the invention can be modified at will unless the modifications depart from the spirit of the invention.

Synthesis of Compound 1

Synthesis of Compound 1

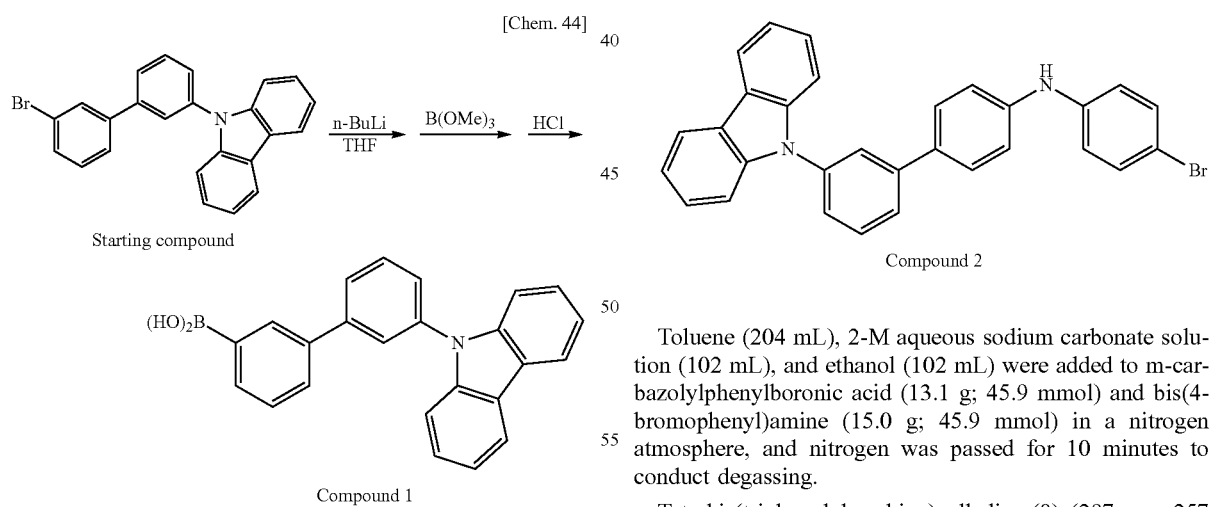

Compound 1

The starting compound (15.0 g; 37 mmol) was introduced into a 500-mL four-necked flask, and nitrogen displacement was conducted for 30 minutes. Into the reaction vessel was introduced 200 mL of anhydrous THF. Thereafter, the solution was cooled to −80° C. A hexane solution of n-BuLi (1.65 M; 24.0 mL) was added dropwise thereto over 30 minutes while taking care that the liquid temperature did not rise, and this mixture was reacted for 4 hours. Trimethoxyborane (11.8 g; 112 mmol) was added dropwise thereto over 10 minutes, and the resultant mixture was reacted for 2 hours.

The reaction solution was warmed to room temperature and stirred for 30 minutes. Two hundred milliliters of 1-N aqueous HCl solution was added to the reaction solution, and this solution was stirred for further 30 minutes. Five hundred milliliters of ethyl acetate was added to the reaction solution to extract the target substance with the organic layer. Thereafter, the organic phase was washed with an aqueous sodium chloride solution. The organic layer was dried with magnesium sulfate and then concentrated with an evaporator. The yellow solid obtained was suspended in and washed with hexane to obtain compound 1 (15.2 g).

Synthesis of Compound 2

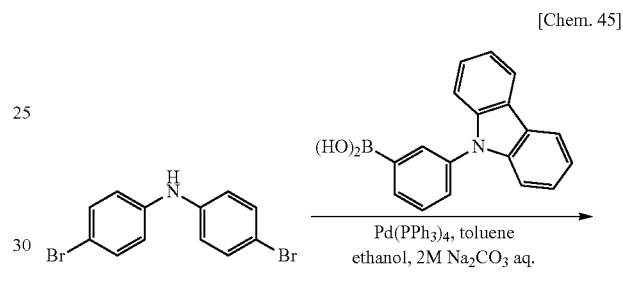

Compound 2

Toluene (204 mL), 2-M aqueous sodium carbonate solution (102 mL), and ethanol (102 mL) were added to m-carbazolylphenylboronic acid (13.1 g; 45.9 mmol) and bis(4-bromophenyl)amine (15.0 g; 45.9 mmol) in a nitrogen atmosphere, and nitrogen was passed for 10 minutes to conduct degassing.

Tetrakis(triphenylphosphine)palladium(0) (297 mg; 257 mol) was added to the mixture, and the resultant mixture was stirred for 3 hours with refluxing. After completion of the reaction, the reaction solution was poured into water and extracted with toluene. The organic layer was washed with purified water and dried with magnesium sulfate. Thereafter, the solvent was distilled off under reduced pressure. The residue was purified by silica gel column chromatography to obtain compound 2 (13.4 g). This compound had a mass spectrometric value of 488 ($M^+$).

Synthesis of Compound 3 introduced into a 500-mL four-necked flask, and nitrogen bubbling was conducted at 60° C. for 1 hour.

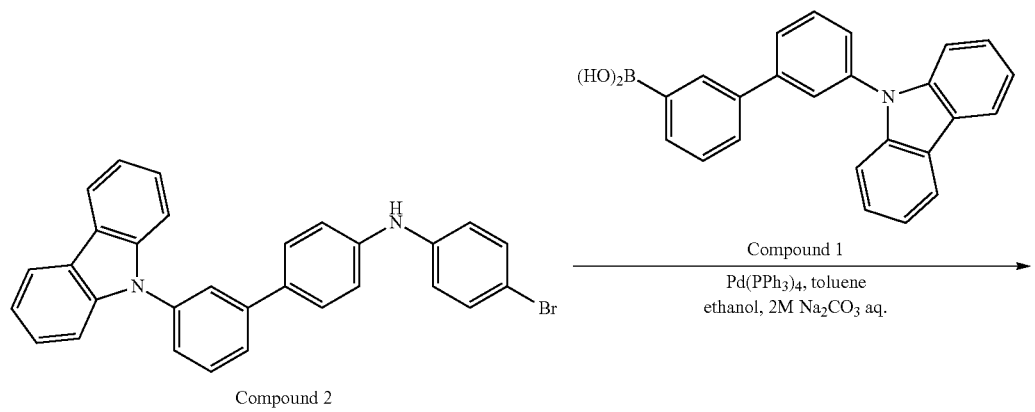

[Chem. 46]

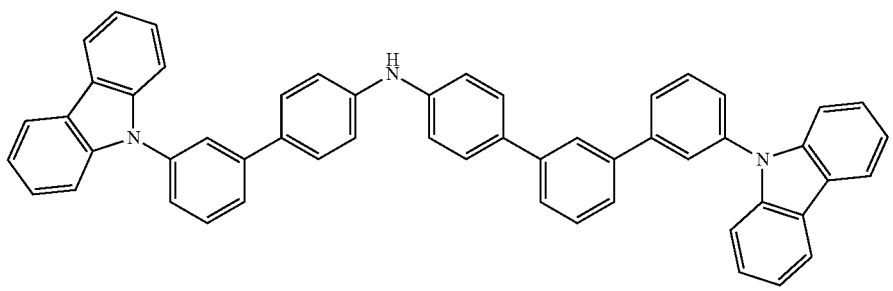

Compound 3

The compound 2 (3.5 g; 7.1 mmol), the compound 1 (5.2 g; 14.3 mol; 2 MR), 122 mL of toluene, 88 mL of ethanol, and 62 mL of aqueous sodium carbonate solution were Tetrakis(triphenylphosphine)palladium(0) (580 mg; 7 mol %) was added to the reaction solution, and the mixture was refluxed for 3 hours. After completion of the reaction, the reaction solution was poured into water and extracted with toluene. The organic layer was washed with purified water and dried with magnesium sulfate. Thereafter, the solvent was distilled off under reduced pressure. The residue was purified by silica gel column chromatography to obtain compound 3 (5.11 g).

Synthesis of Compound 4

[Chem. 47]

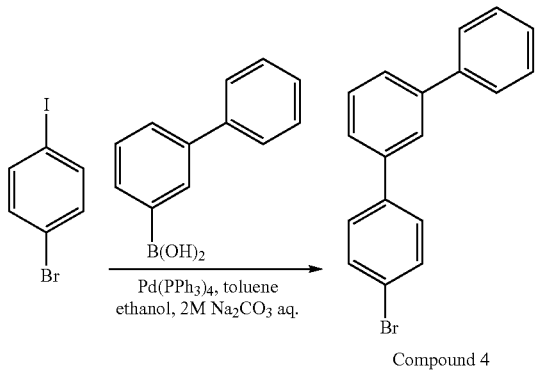

Compound 4

Toluene (176 mL), 2-M aqueous sodium carbonate solution (88 mL), and ethanol (88 mL) were added to 3-biphenylboronic acid (18.3 g; 92.5 mmol) and 4-iodobromobenzene (24.9 g; 87.9 mmol) in a nitrogen atmosphere, and nitrogen was passed for 10 minutes to conduct degassing.

Tetrakis(triphenylphosphine)palladium(0) (1.5 g; 1.29 mmol) was added to the mixture, and the resultant mixture was stirred for 3 hours with refluxing. After completion of the reaction, the reaction solution was poured into water and extracted with toluene.

The organic layer was washed with purified water and dried with magnesium sulfate. Thereafter, the solvent was distilled off under reduced pressure. The residue was purified by silica gel column chromatography to obtain compound 4 (22.6 g). This compound had a mass spectrometric value of 308 (M$^+$).

Synthesis of Compound I

[Chem. 48]

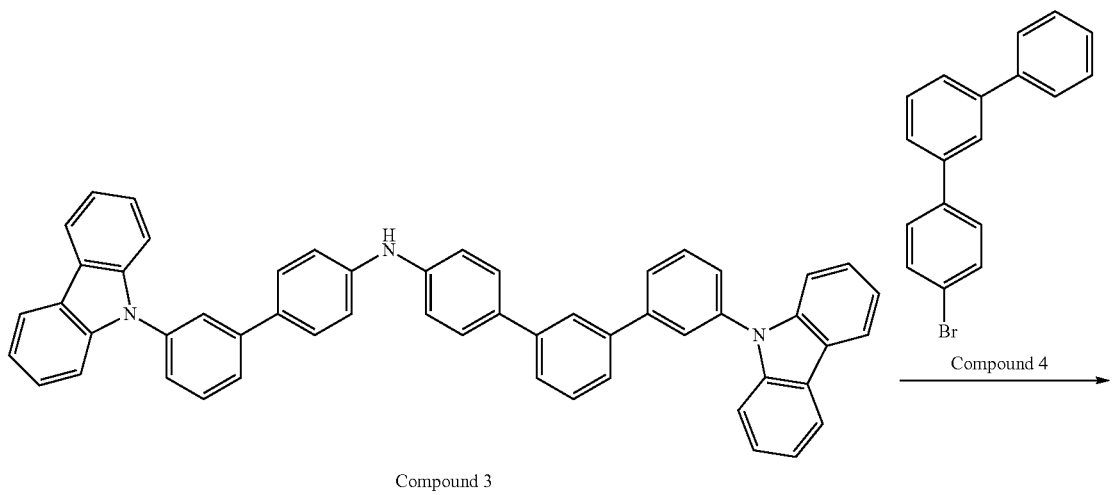

Compound 3

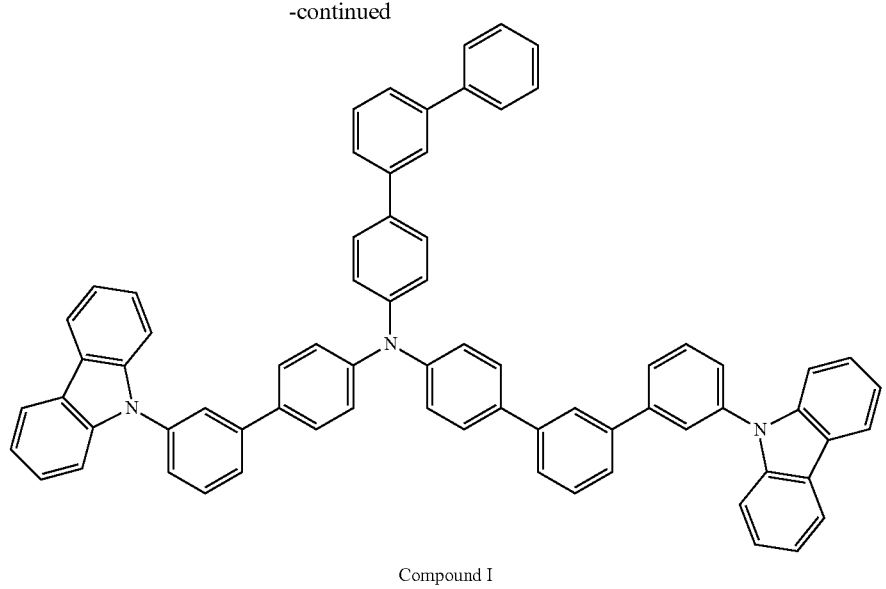

Compound I

The compound 3 (5.11 g; 7.0 mmol), the compound 4 (2.82 g; 2.5 mmol), NaOtBu (1.35 g; 8.8 mmol; 2 MR), and 100 mL of toluene were introduced into a 300-mL four-necked flask, and nitrogen bubbling was conducted for 30 minutes (solution A).

On the other hand, tri-t-butylphosphine (284 mg) was added to a toluene solution (5 mL) of a tris(dibenzylideneacetone)dipalladium chloroform complex (181 mg), and the mixture was heated to 65° C. (solution B). In a nitrogen stream, solution B was added to solution A, and this mixture was reacted with heating and refluxing for 4 hours. The organic layer was washed with purified water and dried with magnesium sulfate. Thereafter, the solvent was distilled off under reduced pressure. The residue was purified by silica gel column chromatography and sublimation purification to obtain compound I (2.1 g).

<Measurement of Solubility in m-Xylene>

The compound I synthesized in [Synthesis of Compound I] above and the comparative compounds X-A and X-B represented by the following structural formulae were examined for solubility in m-xylene. The results thereof are shown in Table 1.

[Chem. 49]

X-A

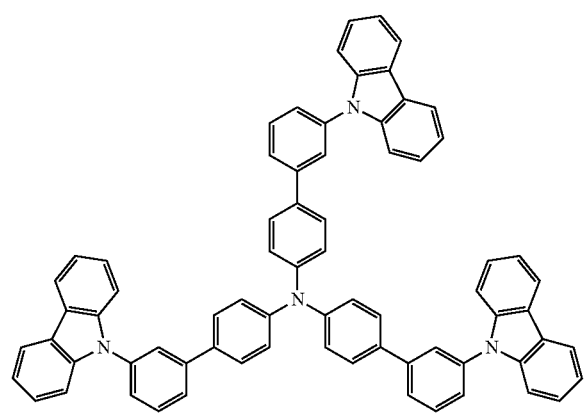

X-B

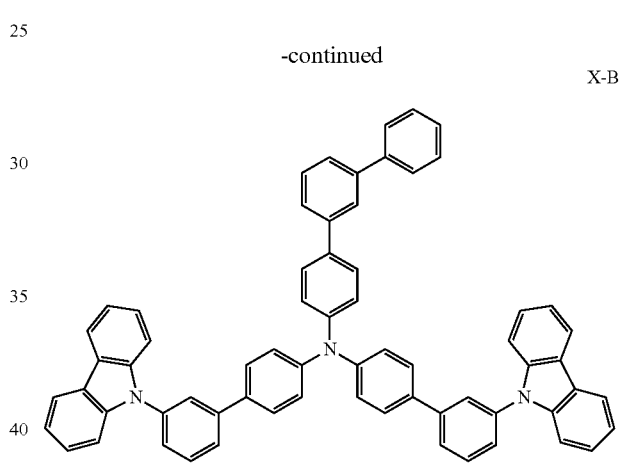

TABLE 1

| | Compound | Glass transition temperature | Concentration | | |
|---|---|---|---|---|---|
| | | | 1.0 mass % | 5.0 mass % | 10 mass % |
| Example 1 | I | 127° C. | + | + | + |
| Comparative Example 1 | X-A | 159° C. | + | − | − |
| Comparative Example 2 | X-B | 120° C. | − | − | − |

+: The compound dissolved.
−: The compound remained undissolved, giving a suspension, or separated out as crystals in 12 hours.

As shown in Table 1, the charge transport material of the invention was ascertained to have high solubility in the organic solvent.

Production of Organic Electroluminescent Element

Example 1

An organic electroluminescent element of the structure shown in FIG. 1 was produced in the following manner. A glass substrate 1 having a size of 17.5 mm×35 mm (thickness, 0.7 mm) was cleaned by subjecting the substrate to ultrasonic cleaning with an aqueous surfactant solution, rinsing with ultrapure water, ultrasonic cleaning with ultrapure water, and rinsing with ultrapure water in this order, subsequently dried by nitrogen blowing, and finally subjected to ultraviolet/ozone cleaning.

A transparent conductive film of indium-tin oxide (ITO) was deposited in a thickness of 150 nm on the glass substrate 1 (the film was deposited by sputtering; sheet resistivity, 15Ω), and this coated substrate was processed by an ordinary technique of photolithography to pattern the conductive film into stripes having a width of 2 mm. Thus, an anode 2 was formed.

The substrate 1 on which the anode 2 had been formed was cleaned by subjecting the substrate to ultrasonic cleaning with acetone, rinsing with pure water, and ultrasonic cleaning with isopropyl alcohol in this order, subsequently dried by nitrogen blowing, and finally subjected to ultraviolet/ozone cleaning.

A composition for hole injection layer formation which included high-molecular compound P-1 having a structure represented by the following formula (weight-average molecular weight (MwA), 93,000; dispersity ratio, 1.69) as a polymeric material for constituting a hole injection layer, compound A-1 having the structure represented by the following formula as an electron-accepting compound and also as a polymerization initiator, and ethyl benzoate as a solvent was prepared. The concentrations of the high-molecular compound P-1 and the compound A-1 in the composition were 2.0% by mass and 0.8% by mass, respectively.

This composition was applied on the anode 2 by spin coating in the air under the conditions of a spinner rotation speed of 1,500 rpm and a spinner rotation period of 30 seconds. The coating film was heated at 230° C. for 3 hours to thereby crosslink the high-molecular compound P-1 and dry the coating film. Thus, an even thin film having a thickness of 45 nm (hole injection layer 3) was formed.

[Chem. 50]

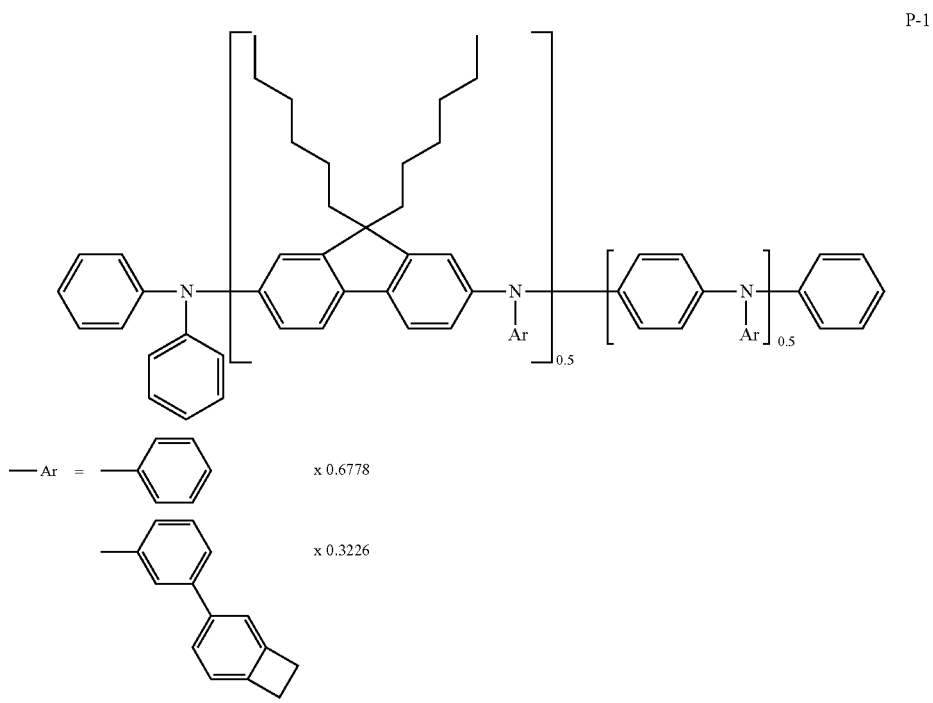

[Chem. 51]

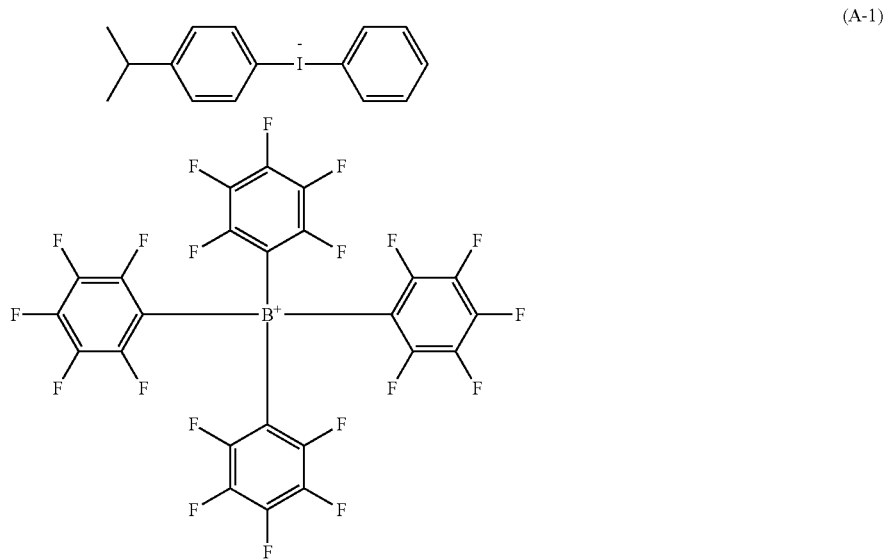

(A-1)

Subsequently, a composition for hole transport layer formation which included a high-molecular compound P-2 having a structure represented by the following formula (weight-average molecular weight (MwB), 66,000; dispersity ratio, 1.56) as a polymeric material for constituting a hole transport layer and cyclohexylbenzene as a solvent was prepared. The concentration of the high-molecular compound P-2 in the composition was 1.4% by mass.

This composition was applied on the hole injection layer 3 by spin coating in nitrogen under the conditions of a spinner rotation speed of 1,500 rpm and a spinner rotation period of 30 seconds. The coating film was heated at 230° C. for 1 hour in nitrogen to thereby crosslink the high-molecular compound P-2 and dry the coating film. Thus, an even thin film having a thickness of 20 nm (hole transport layer 4) was formed.

[Chem. 52]

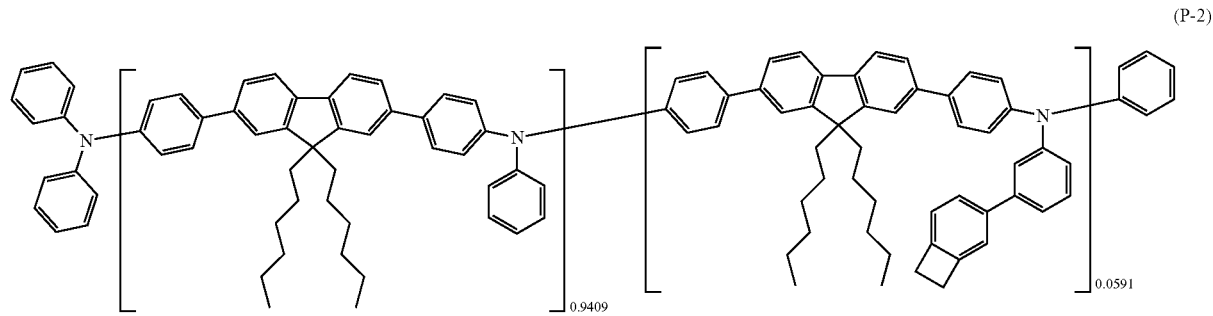

(P-2)

Next, a composition for luminescent-layer formation which included compound C1 represented by the following formula and the compound I obtained in Synthesis Example as charge-transporting compounds, phosphorescent metal complex D1, and cyclohexylbenzene as a solvent was prepared. The concentrations of the compound C1, the compound I, and the phosphorescent metal complex D1 in the composition were 1.1% by mass, 3.4% by mass, and 0.3% by mass, respectively.

This composition was applied on the hole transport layer 4 by spin coating in nitrogen under the conditions of a spinner rotation speed of 1,500 rpm and a spinner rotation period of 30 seconds. The coating film was dried at 130° C. for 1 hour at a reduced pressure (0.1 MPa) to thereby dry the coating film. Thus, an even thin film having a thickness of 50 nm (luminescent layer 5) was formed.

[Chem. 53]

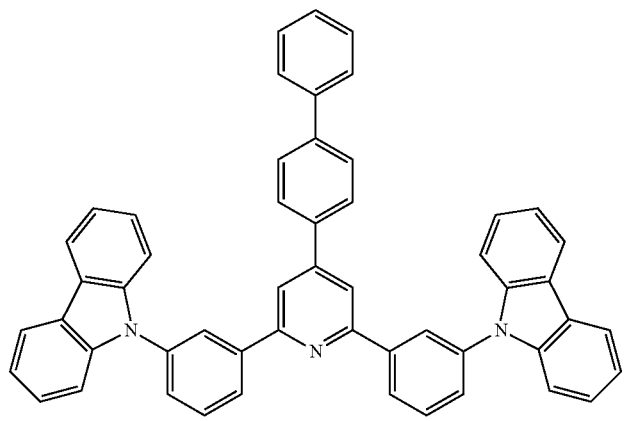

Compound C1

[Chem. 54]

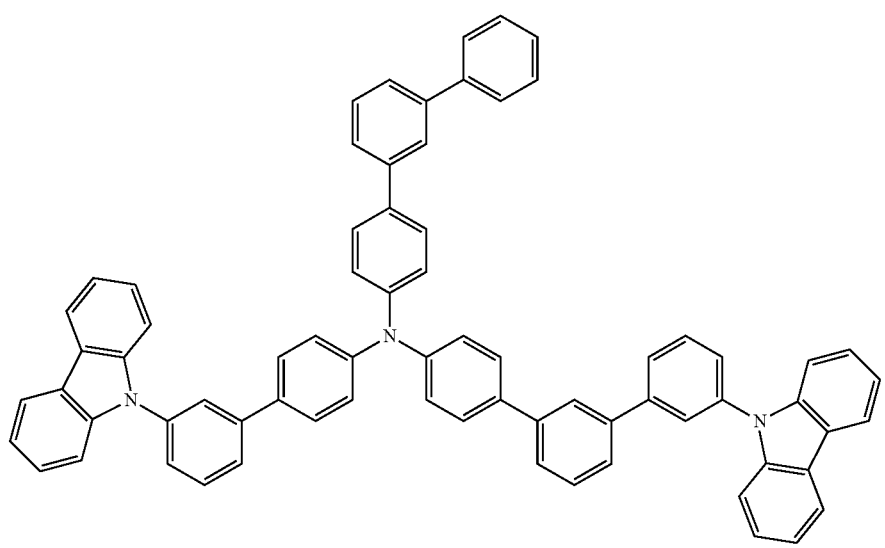

Compound I

[Chem. 55]

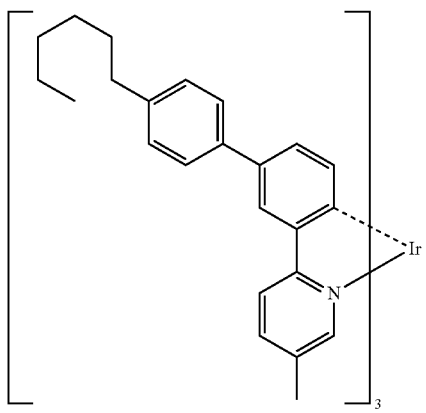

Here, the substrate on which the layers including the luminescent layer 5 had been formed was transferred into a vacuum deposition apparatus, and the apparatus was evacuated to a degree of vacuum within the apparatus of at least $1.3 \times 10^{-4}$ Pa. Thereafter, a layer of compound C2 shown below was formed on the luminescent layer 5 by vacuum deposition to obtain a hole blocking layer 6. The rate of deposition was regulated so as to be in the range of 1.4-1.5 Å/sec, and the layer was deposited in a thickness of 10 nm. The degree of vacuum during the deposition was $1.3 \times 10^{-4}$ Pa.

[Chem. 56]

Compound C2

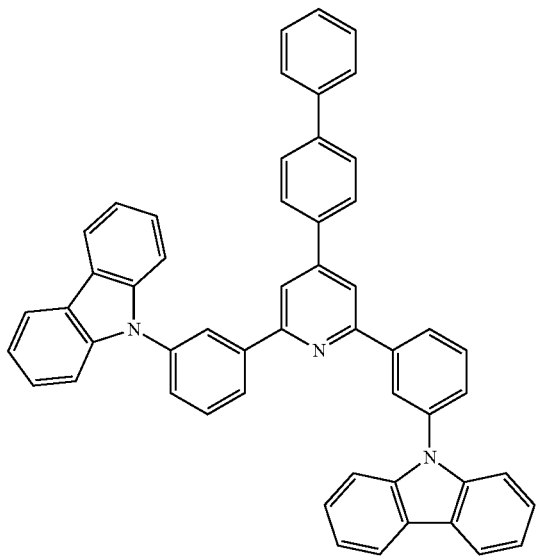

Subsequently, the aluminum 8-hydroxyquinoline complex (ET-1) shown below was heated and vapor-deposited on the hole blocking layer 6 to form an electron transport layer 7. The degree of vacuum during the deposition was regulated to $1.3 \times 10^{-4}$ Pa, and the rate of deposition was regulated so as to be in the range of 1.6-1.8 Å/sec. The layer was deposited in a thickness of 30 nm.

(D1)

[Chem. 57]

ET-1

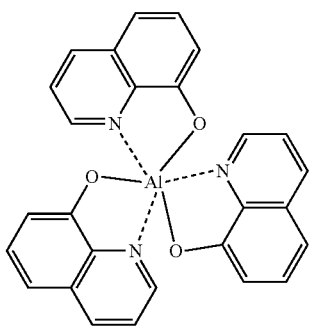

Here, the element in which the layers including the vapor-deposited electron transport layer 7 had been formed was temporarily taken out and disposed in another vacuum deposition apparatus. A shadow mask in the form of stripes with a width of 2 mm was brought, as a mask for cathode deposition, into close contact with the element so that these stripes were perpendicular to the ITO stripes of the anode 2, and the apparatus was evacuated to a degree of vacuum within the apparatus of at least $2.3 \times 10^{-4}$ Pa.

First, lithium fluoride (LiF) was deposited as an electron injection layer 8 in a thickness of 0.5 nm on the electron transport layer 7 at a deposition rate of 0.1 Å/sec using a molybdenum boat. The degree of vacuum during the deposition was $2.6 \times 10^{-4}$ Pa.

Next, aluminum was likewise heated using a molybdenum boat, and an aluminum layer having a thickness of 80 nm was formed as a cathode 9 while regulating the rate of deposition so as to be in the range of 1.0-4.9 Å/sec. The degree of vacuum during the deposition was $2.6 \times 10^{-4}$ Pa. During the deposition of these two layers, the temperature of the substrate was kept at room temperature.

Subsequently, sealing was conducted in the following manner in order to prevent the element from being deteriorated by the action of atmospheric moisture, etc. during storage.

In a gloved nitrogen box, a photocurable resin (30Y-437, manufactured by ThreeBond Co., Ltd.) was applied in a width of about 1 mm to the periphery of a glass plate having a size of 23 mm×23 mm, and a moisture getter sheet (manufactured by Dynic Corp.) was disposed in a central part. The substrate on which the cathode had been formed was laminated to the getter sheet so that the side having the deposited layers faced the desiccant sheet. Thereafter, only the region where the photocurable resin had been applied was irradiated with ultraviolet light to cure the resin.

Thus, an organic electroluminescent element having a luminescent area with a size of 2 mm×2 mm was obtained. This element had the following luminescent characteristics. The operating voltage thereof at 1,000 cd/m$^2$ was 7.9 V, and the luminescent efficiency thereof at 1,000 cd/m$^2$ was 40.0 cd/A. The operating voltage (V) thereof at 10 mA was 9.4 V.

Those results showed that the organic electroluminescent element of the invention had a high luminescent efficiency.

Synthesis of Compound 11

Synthesis of Compound 5

[Chem. 58]

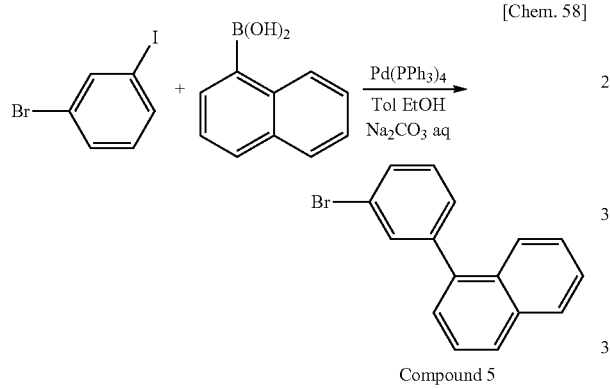

Compound 5

Toluene (174 mL), 2-M aqueous sodium carbonate solution (181 mL), and ethanol (88 mL) were added to 1-naphthylboronic acid (20.0 g; 116.3 mmol) and 3-iodobromobenzene (36.2 g; 128 mmol) in a nitrogen atmosphere, and nitrogen was passed for 10 minutes to conduct degassing.

Tetrakis(triphenylphosphine)palladium(0) (1.34 g) was added to the mixture, and the resultant mixture was stirred for 6 hours with refluxing. After completion of the reaction, the reaction solution was poured into water and extracted with toluene. The organic layer was washed with purified water and dried with magnesium sulfate. Thereafter, the solvent was distilled off under reduced pressure. The residue was purified by silica gel column chromatography to obtain compound 5 (26.7 g).

Synthesis of Compound 6

[Chem. 59]

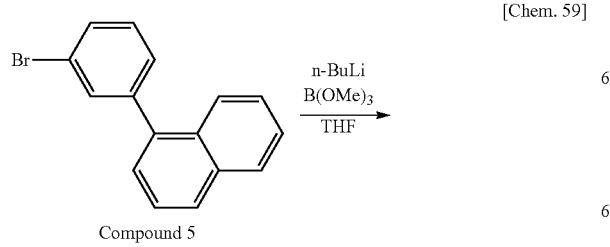

Compound 5

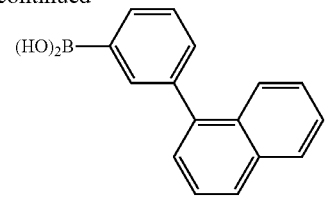

Compound 6

In a nitrogen atmosphere, 353.7 mL of dehydrated THF was added to the compound 5 (27.2 g; 96 mmol), and nitrogen was passed for 10 minutes to conduct degassing. The solution was cooled to −75° C. Thereafter, 72.0 mL of a 1.6-M hexane solution of n-butyllithium was added dropwise thereto. After stirring for 1 hour at −75° C., trimethoxyborane (31.9 g; 307 mmol) was added dropwise thereto.

The resultant mixture was stirred at −75° C. for 2 hours and then warmed to room temperature. To this solution was added 177 mL of 1-N hydrochloric acid solution. This mixture was stirred for 30 minutes. To the resultant solution was added 101 mL of ethyl acetate. The organic layer was washed with purified water and dried with magnesium sulfate. Thereafter, the solvent was distilled off under reduced pressure. Thus, compound 6 (29.8 g) was obtained.

Synthesis of Compound 7

[Chem. 60]

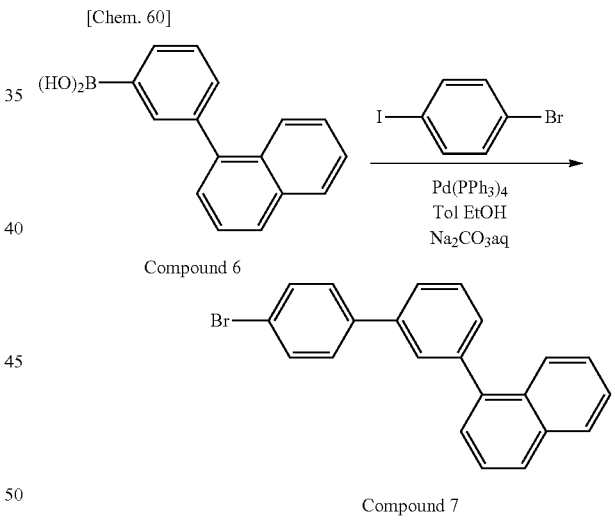

Compound 7

Toluene (631.7 mL), 2-M aqueous sodium carbonate solution (327.8 mL), and ethanol (315.7 mL) were added to the compound 6 (29.8 g; 120 mmol) and 4-iodobromobenzene (40.78 g; 144 mmol) in a nitrogen atmosphere, and nitrogen was passed for 10 minutes to conduct degassing.

Tetrakis(triphenylphosphine)palladium(0) (2.01 g) was added to the mixture, and the resultant mixture was stirred for 6 hours with refluxing. After completion of the reaction, the reaction solution was poured into water and extracted with toluene.

The organic layer was washed with purified water and dried with magnesium sulfate. Thereafter, the solvent was distilled off under reduced pressure. The residue was purified by silica gel column chromatography to obtain compound 7 (27.32 g).

Synthesis of Compound 8

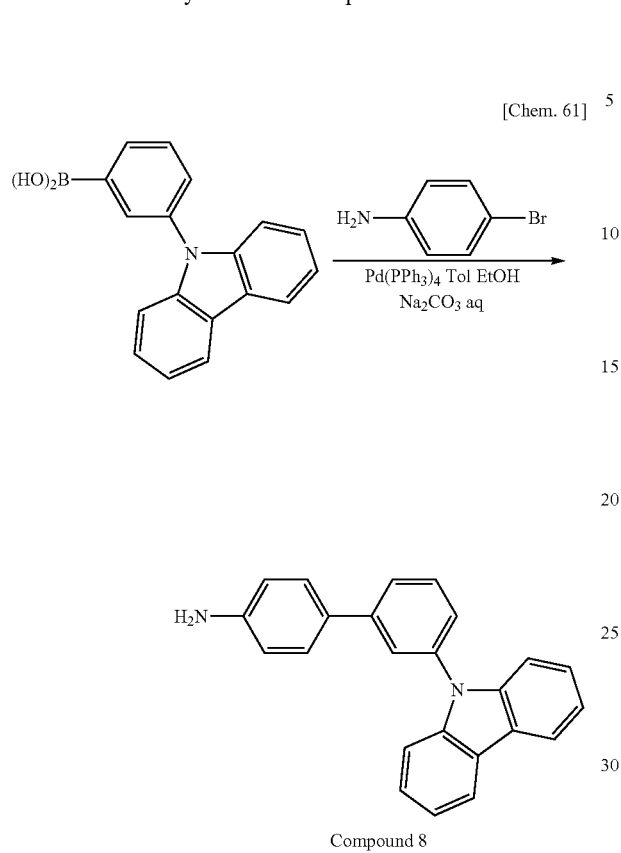

Compound 8

Toluene (558.4 mL), 2-M aqueous sodium carbonate solution (278.7 mL), and ethanol (279.5 mL) were added to m-carbazolylphenylboronic acid (28.04 g; 98 mmol) and 4-bromoaniline (16.00 g; 93 mmol) in a nitrogen atmosphere, and nitrogen was passed for 10 minutes to conduct degassing.

Tetrakis(triphenylphosphine)palladium(0) (2.15 g) was added to the mixture, and the resultant mixture was stirred for 6 hours with refluxing. After completion of the reaction, the reaction solution was poured into water and extracted with toluene.

The organic layer was washed with purified water and dried with magnesium sulfate. Thereafter, the solvent was distilled off under reduced pressure. The residue was purified by silica gel column chromatography to obtain compound 8 (27.37 g).

[Chem. 62]

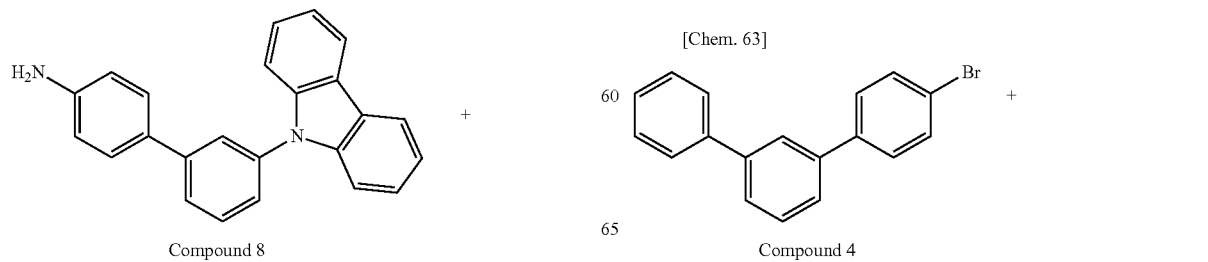

Into a 200-mL four-necked flask were introduced the compound 8 (5.0 g; 615.0 mmol), the compound 7 (4.8 g; 13.5 mmol), NaOtBu (4.88 g; 50 mmol), and 100 mL of toluene. Nitrogen bubbling was conducted for 30 minutes (solution A).

On the other hand, tri-t-butylphosphine (121 mg) was added to a toluene solution (6 mL) of a tris(dibenzylideneacetone)dipalladium chloroform complex (77 mg), and the mixture was heated to 65° C. (solution B).

In a nitrogen stream, solution B was added to solution A, and this mixture was reacted with heating and refluxing for 4 hours. The organic layer was washed with purified water and dried with magnesium sulfate. Thereafter, the solvent was distilled off under reduced pressure. The residue was purified by silica gel column chromatography to obtain compound 9 (6.4 g).

[Chem. 63]

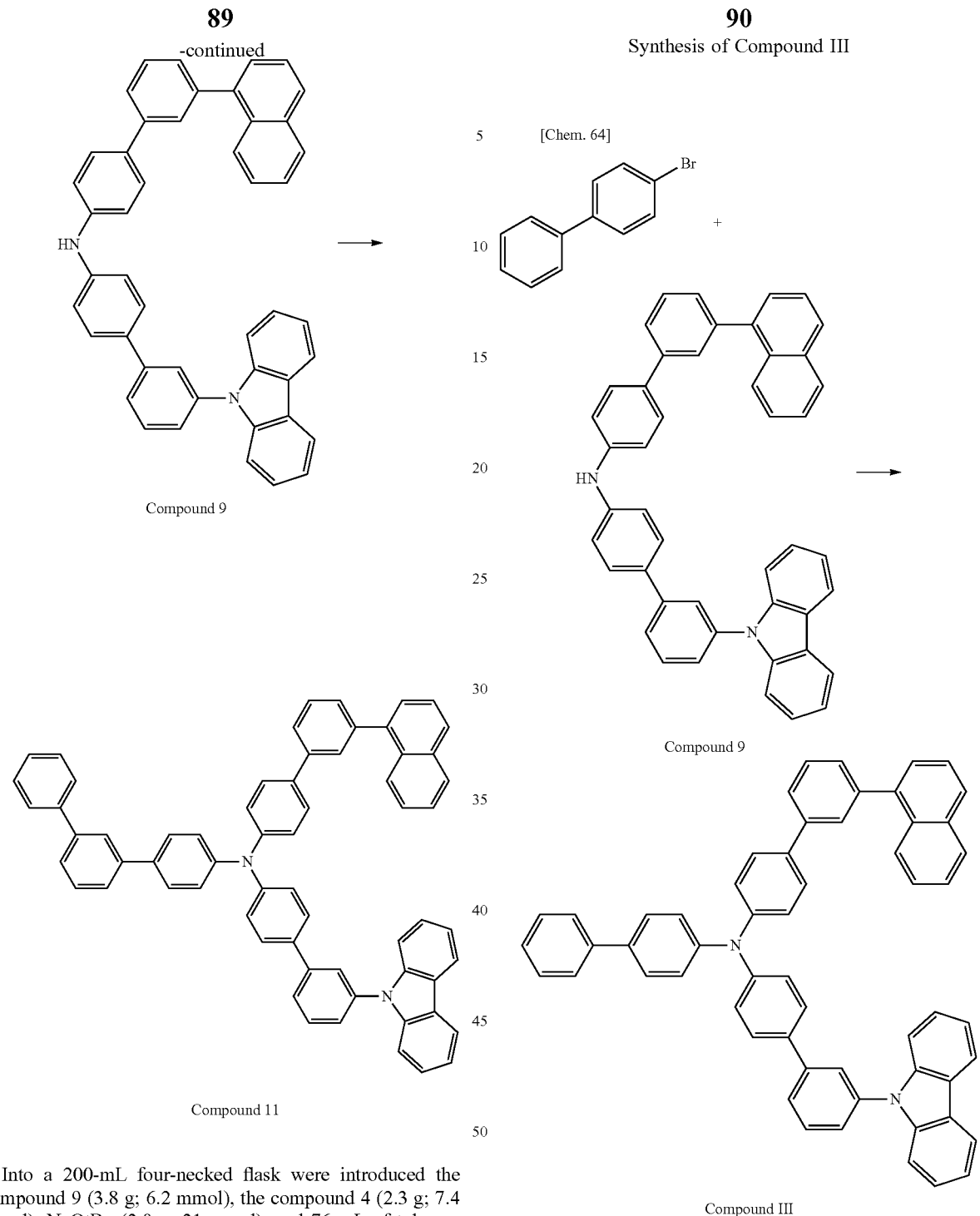

Compound 9

Compound 11

Synthesis of Compound III

[Chem. 64]

Compound 9

Compound III

Into a 200-mL four-necked flask were introduced the compound 9 (3.8 g; 6.2 mmol), the compound 4 (2.3 g; 7.4 mmol), NaOtBu (2.0 g; 21 mmol), and 76 mL of toluene. Nitrogen bubbling was conducted for 30 minutes (solution A).

On the other hand, tri-t-butylphosphine (50 mg) was added to a toluene solution (6 mL) of a tris(dibenzylideneacetone)dipalladium chloroform complex (32 mg), and the mixture was heated to 65° C. (solution B). In a nitrogen stream, solution B was added to solution A, and this mixture was reacted with heating and refluxing for 4 hours. The organic layer was washed with purified water and dried with magnesium sulfate. Thereafter, the solvent was distilled off under reduced pressure. The residue was purified by silica gel column chromatography to obtain compound II (4.4 g).

Into a 100-mL four-necked flask were introduced the compound 9 (0.65 g; 1.1 mmol), 4-bromobiphenyl (0.36 g; 1.3 mmol), NaOtBu (0.35 g; 3.6 mmol), and 30 mL of toluene. Nitrogen bubbling was conducted for 30 minutes (solution A).

On the other hand, tri-t-butylphosphine (8.6 mg) was added to a toluene solution (5 mL) of a tris(dibenzylideneacetone)dipalladium chloroform complex (5.5 mg), and the mixture was heated to 65° C. (solution B). In a nitrogen stream, solution B was added to solution A, and this mixture was reacted with heating and refluxing for 4 hours. The organic layer was washed with purified water and dried with magnesium sulfate. Thereafter, the solvent was distilled off under reduced pressure. The residue was purified by silica gel column chromatography and with a sublimation purification device to obtain compound III (0.44 g).

Synthesis of Compound X-C

[Chem. 65]

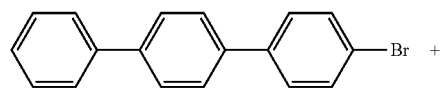

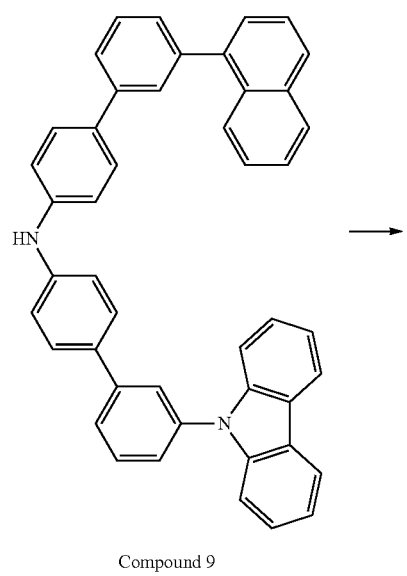

Compound 9

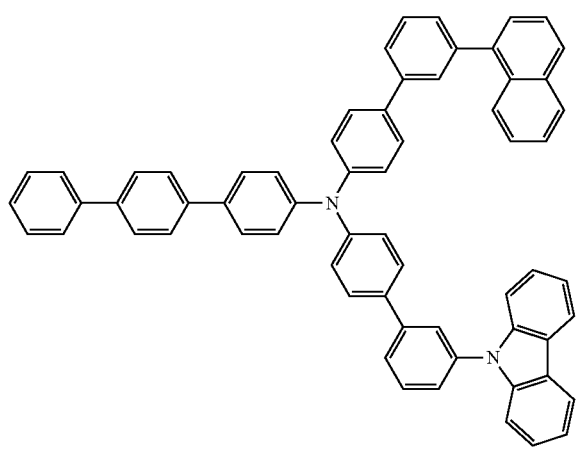

Compound X-C

Into a 300-mL four-necked flask were introduced the compound 9 (0.43 g; 0.70 mmol), 4-bromoterphenyl (0.26 g; 0.84 mmol), NaOtBu (0.23 g; 2.4 mmol), and 10 mL of toluene. Nitrogen bubbling was conducted for 30 minutes (solution A).

On the other hand, tri-t-butylphosphine (5.7 mg) was added to a toluene solution (5 mL) of a tris(dibenzylideneacetone)dipalladium chloroform complex (3.6 mg), and the mixture was heated to 65° C. (solution B). In a nitrogen stream, solution B was added to solution A, and this mixture was reacted with heating and refluxing for 4 hours. The organic layer was washed with purified water and dried with magnesium sulfate. Thereafter, the solvent was distilled off under reduced pressure. The residue was purified by silica gel column chromatography and with a sublimation purification device to obtain compound X-C (0.13 g).

Example 2

An organic electroluminescent element of the structure shown in FIG. 1 was produced in the following manner. A glass substrate 1 having a size of 25 mm×37.5 mm (thickness, 0.7 mm) was cleaned by subjecting the substrate to ultrasonic cleaning with an aqueous surfactant solution, rinsing with ultrapure water, ultrasonic cleaning with ultrapure water, and rinsing with ultrapure water in this order, subsequently dried by nitrogen blowing, and finally subjected to ultraviolet/ozone cleaning.

A transparent conductive film of indium-tin oxide (ITO) was deposited in a thickness of 70 nm on the glass substrate 1 (the film was deposited by sputtering; sheet resistivity, 15Ω), and this coated substrate was processed by an ordinary technique of photolithography to pattern the conductive film into stripes having a width of 2 mm. Thus, an anode 2 was formed.

The substrate 1 on which the anode 2 had been formed was cleaned by subjecting the substrate to ultrasonic cleaning with an aqueous surfactant solution, rinsing with ultrapure water, ultrasonic cleaning with ultrapure water, and rinsing with ultrapure water in this order, subsequently dried by nitrogen blowing, and finally subjected to ultraviolet/ozone cleaning.

The composition used in Example 1 was used as a polymeric material for constituting a hole injection layer. This composition was applied on the anode 2 by spin coating in the air under the conditions of a spinner rotation speed of 1,500 rpm and a spinner rotation period of 30 seconds. The coating film was heated at 230° C. for 1 hour to thereby crosslink the high-molecular compound P-1 and dry the coating film. Thus, an even thin film having a thickness of 30 nm (hole injection layer 3) was formed.

[Chem. 66]
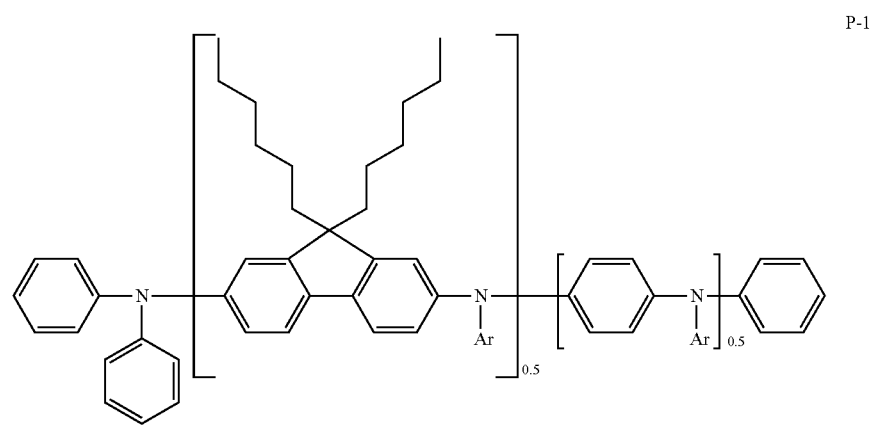
P-1
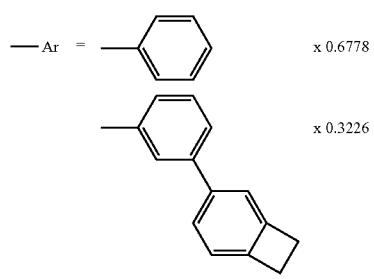
x 0.6778
x 0.3226

[Chem. 67]

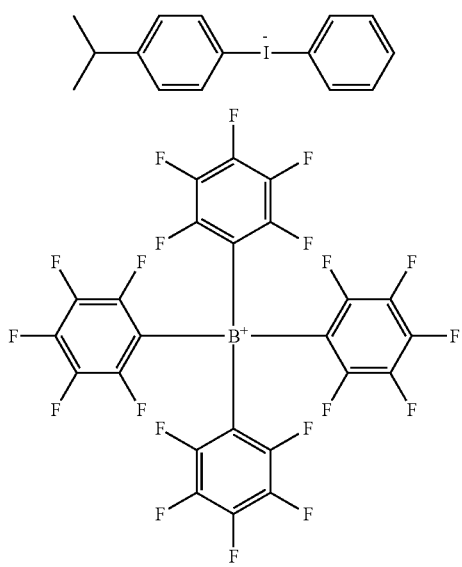

(A-1)

Subsequently, a composition for hole transport layer formation which included a high-molecular compound P-2 having a structure represented by the following formula (weight-average molecular weight (MwB), 66,000; dispersity ratio, 1.56) as a polymeric material for constituting a hole transport layer and cyclohexylbenzene as a solvent was prepared. The concentration of the high-molecular compound P-2 in the composition was 1.1% by mass.

This composition was applied on the hole injection layer 3 by spin coating in nitrogen under the conditions of a spinner rotation speed of 1,500 rpm and a spinner rotation period of 120 seconds. The coating film was heated at 230° C. for 1 hour in nitrogen to thereby crosslink the high-molecular compound P-2 and dry the coating film. Thus, an even thin film having a thickness of 14 nm (hole transport layer 4) was formed.

[Chem. 68]

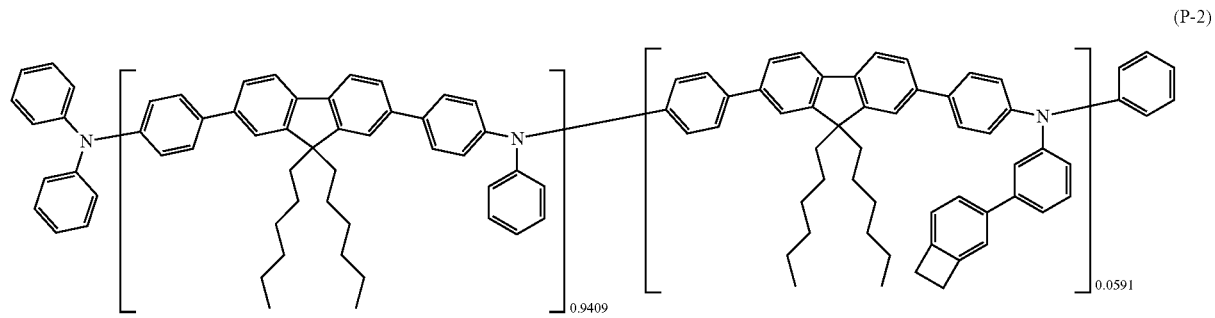

(P-2)

Next, a composition for luminescent-layer formation which included compound C3 represented by the following formula and the compound II obtained in Synthesis Example as charge-transporting compounds, phosphorescent metal complex D2, and cyclohexylbenzene as a solvent was prepared. The concentrations of the compound C3, the compound II, and the phosphorescent metal complex D2 in the composition were 1.25% by mass, 3.75% by mass, and 0.7% by mass, respectively.

This composition was applied on the hole transport layer 4 by spin coating in nitrogen under the conditions of a spinner rotation speed of 1,700 rpm and a spinner rotation period of 120 seconds. The coating film was dried at 130° C. for 10 minutes in nitrogen to thereby dry the coating film. Thus, an even thin film having a thickness of 63 nm (luminescent layer 5) was formed.

[Chem. 69]

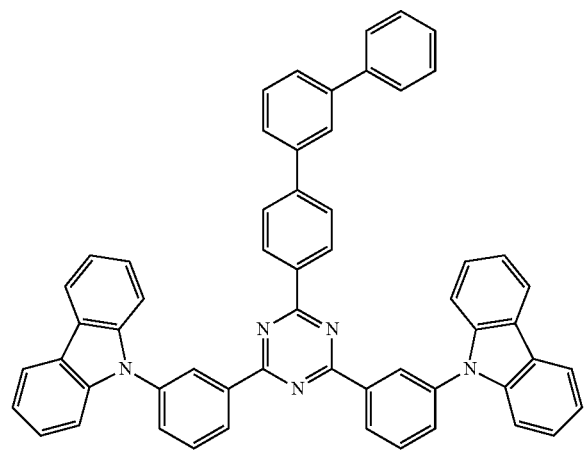

(C3)

[Chem. 70]

Compound II

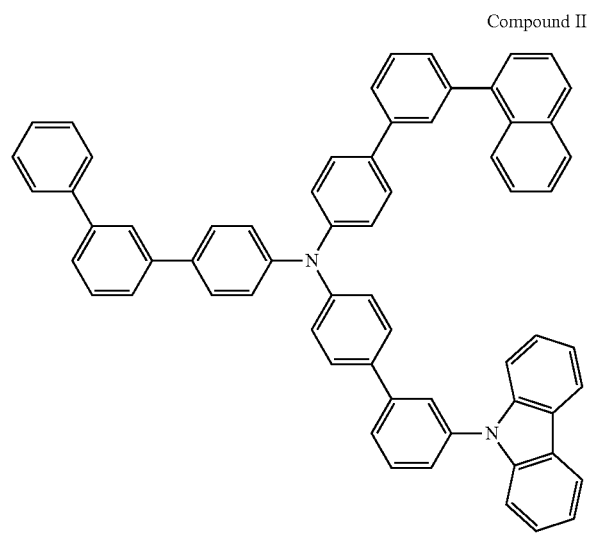

[Chem. 71]

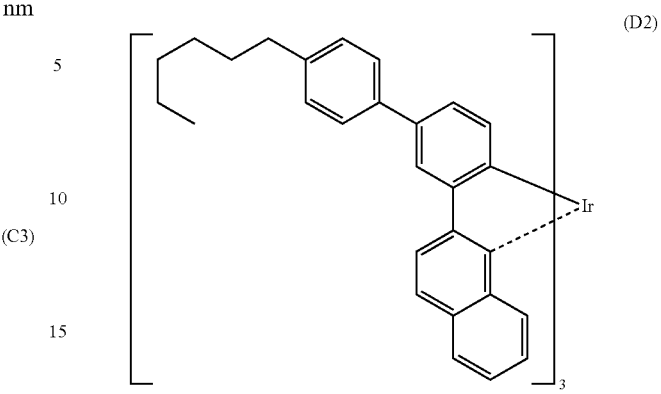

(D2)

Here, the substrate on which the layers including the luminescent layer 5 had been formed was transferred into a vacuum deposition apparatus, and the apparatus was evacuated to a degree of vacuum within the apparatus of at least $0.9 \times 10^{-6}$ Torr. Thereafter, a layer of the compound C2 used in Example 1 was formed on the luminescent layer 5 by vacuum deposition to obtain a hole blocking layer 6. The rate of deposition was regulated so as to be in the range of 0.8-1.0 Å/sec, and the layer was deposited in a thickness of 10 nm. The degree of vacuum during the deposition was $0.9 \times 10^{-6}$ Pa.

Subsequently, (ET-1) used in Example 1 was heated and vapor-deposited on the hole blocking layer 6 to form an electron transport layer 7. The degree of vacuum during the deposition was regulated to $0.8 \times 10^{-6}$ Torr, and the rate of deposition was regulated so as to be in the range of 0.8-1.0 Å/sec. The layer was deposited in a thickness of 20 nm.

Here, the element in which the layers including the vapor-deposited electron transport layer 7 had been formed was temporarily taken out and disposed in another vacuum deposition apparatus. A shadow mask in the form of stripes with a width of 2 mm was brought, as a mask for cathode deposition, into close contact with the element so that these stripes were perpendicular to the ITO stripes of the anode 2, and the apparatus was evacuated to a degree of vacuum within the apparatus of at least $2.1 \times 10^{-4}$ Pa.

First, lithium fluoride (LiF) was deposited as an electron injection layer 8 in a thickness of 0.5 nm on the electron transport layer 7 at a deposition rate of 0.08-0.14 Å/sec using a molybdenum boat. The degree of vacuum during the deposition was $2.7 \times 10^{-4}$ Pa.

Next, aluminum was likewise heated using a molybdenum boat, and an aluminum layer having a thickness of 80 nm was formed as a cathode 9 while regulating the rate of deposition so as to be in the range of 1.0-5.1 Å/sec. The degree of vacuum during the deposition was $5.1 \times 10^{-4}$ Pa. During the deposition of these two layers, the temperature of the substrate was kept at room temperature.

Subsequently, the same sealing as in Example 1 was conducted in order to prevent the element from being deteriorated by the action of atmospheric moisture, etc. during storage.

Thus, an organic electroluminescent element having a luminescent area with a size of 2 mm×2 mm was obtained. This element had the following luminescent characteristics. The operating voltage thereof at 10 mA/cm² was 7.18 V. The time period required for the luminance thereof to decrease to 95% of the initial luminance was 40 hours, and the increase in operating voltage which was observed when the luminance of the element had decreased to 95% of the initial luminance was 0.05 V.

Example 3

The same procedure as in Example 2 was conducted, except that compound III was used in place of the compound II.

[Chem. 72]

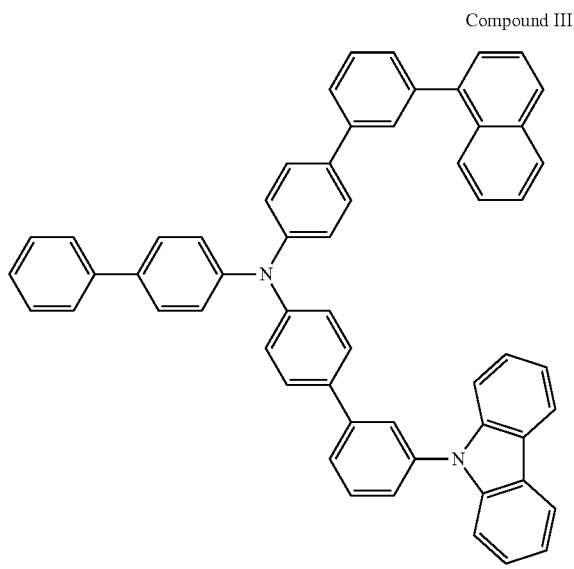

Compound III

This element had the following luminescent characteristics. The operating voltage thereof at 10 mA/cm$^2$ was 7.12 V. The time period required for the luminance thereof to decrease to 95% of the initial luminance was 40 hours, and the increase in operating voltage which was observed when the luminance of the element had decreased to 95% of the initial luminance was 0.06 V.

COMPARATIVE EXAMPLE 3

The same procedure as in Example 2 was conducted, except that the compound X-A was used in place of the compound II. This element had the following luminescent characteristics. The operating voltage thereof at 10 mA/cm$^2$ was 8.63 V. The time period required for the luminance thereof to decrease to 95% of the initial luminance was 20 hours, and the increase in operating voltage which was observed when the luminance of the element had decreased to 95% of the initial luminance was 0.19 V.

COMPARATIVE EXAMPLE 4

The same procedure as in Example 2 was conducted, except that the compound X-C was used in place of the compound II. The compound X-C crystallized after dissolved, and production of an element was impossible.

The results obtained above are summarized in Table 2.

TABLE 2

| | Time period to decrease to 95% of initial luminance | Operating voltage | Increase in operating voltage in constant-current driving |
|---|---|---|---|
| Example 2 | 40 h | 7.18 V | +0.05 V |
| Example 3 | 40 h | 7.12 V | +0.06 V |
| Comparative Example 3 | 20 h | 8.63 V | +0.19 V |
| Comparative Example 4 | production of element was impossible because of insufficient solubility | | |

The results showed that the organic electroluminescent elements employing the charge transport materials of the invention had a low operating voltage and a long working life and showed only a slight increase in voltage during driving.

INDUSTRIAL APPLICABILITY

The charge transport material of the invention is suitable for use in various fields in which organic EL elements are used, for example, in the fields of flat panel displays (e.g., displays for OA computers and wall-mounted TV receivers), light sources taking advantage of the feature of a surface light emitter (e.g., the light source of a copier and the backlight of a liquid-crystal display or instrument), display panels, marker lights, and the like.

Furthermore, since the charge transport material of the invention essentially has excellent stability to oxidation and reduction, the material is useful not only in organic electroluminescent elements but also in general organic devices including electrophotographic photoreceptors and organic solar cells.

While the invention has been described in detail and with reference to specific embodiments thereof, it will be apparent to one skilled in the art that various changes and modifications can be made therein without departing from the spirit and scope thereof. This application is based on a Japanese patent application filed on Aug. 27, 2009 (Application No. 2009-196782), the entire contents thereof being incorporated herein by reference.

DESCRIPTION OF THE REFERENCE NUMERALS

1 Substrate
2 Anode
3 Hole injection layer
4 Hole transport layer
5 Luminescent layer
6 Hole blocking layer
7 Electron transport layer
8 Electron injection layer
9 Cathode

The invention claimed is:

1. A monoamine compound represented by formula (1):

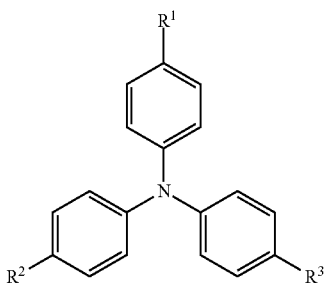

(1)

wherein $R^1$ to $R^3$ each independently represent a phenyl group which may have one or more substituents, provided that at least one of $R^1$ to $R^3$ independently represents a phenyl group having as a substituent an aromatic heterocyclic group which may have a substituent;

at least one of said substituents of each of $R^1$ to $R^3$, when present, is in the ortho or meta positions;

said substituents may be bonded to each other to form a cyclic structure;

a difference between a carbon number of the group having the greatest carbon numbers among $R^1$ to $R^3$ and a carbon number of the group having the smallest carbon numbers among $R^1$ to $R^3$ is 10 or more; and the carbon number also include a carbon number of the substituents of $R^1$ to $R^3$, with the proviso that none of $R^1$, $R^2$ and $R^3$ is a group which is the same as the other.

2. A monoamine compound represented by formula (1):

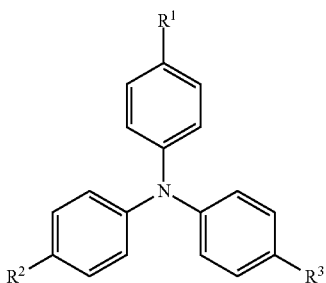

(1)

wherein $R^1$ to $R^3$ each independently represent a phenyl group which may have one or more substituents, provided that at least one of $R^1$ to $R^3$ independently represents a phenyl group having as a substituent an aromatic heterocyclic group which may have a substituent;

at least one of said substituents of each of $R^1$ to $R^3$, when present, is in the ortho or meta positions;

said substituents may be bonded to each other to form a cyclic structure;

a difference between a carbon number of the group having the greatest carbon numbers among $R^1$ to $R^3$ and a carbon number of the group having the second greater carbon numbers among $R^1$ to $R^3$ is 5 or more; and the carbon number also include a carbon number of the substituent of $R^1$ to $R^3$, with the proviso that none of $R^1$, $R^2$ and $R^3$ is a group which is the same as the other.

3. A monoamine compound represented by formula (1):

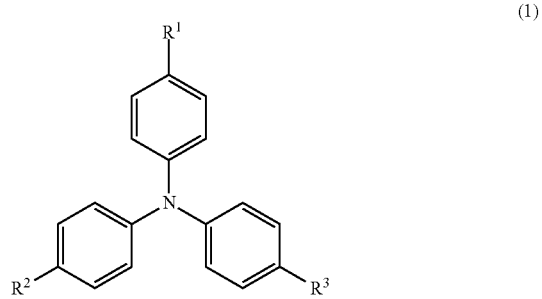

(1)

wherein $R^1$ to $R^3$ each independently represent a phenyl group which may have one or more substituents, provided that at least one of $R^1$ to $R^3$ independently represents a phenyl group having as a substituent an aromatic heterocyclic group which may have a substituent;

at least one of said substituents of each of $R^1$ to $R^3$, when present, is in the ortho or meta positions;

said substituents may be bonded to each other to form a cyclic structure;

a difference between a carbon number of the group having the smallest carbon numbers among $R^1$ to $R^3$ and a carbon number of the group having the second greater carbon numbers among $R^1$ to $R^3$ is 5 or more; and the carbon number also include a carbon number of the substituents of $R^1$ to $R^3$, with the proviso that none of $R^1$, $R^2$ and $R^3$ is a group which is the same as the other.

4. The monoamine compound according to claim 1, wherein when one or more of $R^1$ to $R^3$ independently represent a group other than a phenyl group having as a substituent an aromatic heterocyclic group which may have a substituent, $R^1$ to $R^3$ each independently represent a phenyl group having as a substituent an aromatic hydrocarbon group which may have a substituent.

5. The monoamine compound according to claim 1, wherein a difference between a carbon number of the group having the greatest carbon numbers among $R^1$ to $R^3$ and a carbon number of the group having the second greater carbon numbers among $R^1$ to $R^3$ is 5 or more.

6. The monoamine compound according to claim 1, wherein a difference between a carbon number of the group having the smallest carbon numbers among $R^1$ to $R^3$ and a carbon number of the group having the second greater carbon numbers among $R^1$ to $R^3$ is 5 or more.

7. The monoamine compound according to claim 5, wherein a difference between a carbon number of the group having the smallest carbon numbers among $R^1$ to $R^3$ and a carbon number of the group having the second greater carbon numbers among $R^1$ to $R^3$ is 5 or more.

8. The monoamine compound according to claim 2, wherein when one or more of $R^1$ to $R^3$ independently represent a group other than a phenyl group having as a substituent an aromatic heterocyclic group which may have a substituent, $R^1$ to $R^3$ each independently represent a phenyl group having as a substituent an aromatic hydrocarbon group which may have a substituent.

9. The monoamine compound according to claim 3, wherein when one or more of $R^1$ to $R^3$ independently represent a group other than a phenyl group having as a substituent an aromatic heterocyclic group which may have a substituent, $R^1$ to $R^3$ each independently represent a phenyl group having as a substituent an aromatic hydrocarbon group which may have a substituent.

10. The monoamine compound according to claim 1, wherein at least one of $R^1$ to $R^3$ comprises a partial structure represented by formula (2-1):

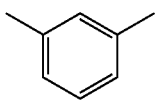

(2-1)

wherein structural formula (2-1) may have one or more substituents, and the substituent may have been bonded to each other to form a cyclic structure.

11. The monoamine compound according to claim 1, wherein in formula (1), $R^1$ to $R^3$ each independently are a phenyl group which may have a substituent in an m-position.

12. The monoamine compound according to claim 1, wherein in formula (1), at least one of $R^1$ to $R^3$ is a group including a partial structure represented by formula (2-2):

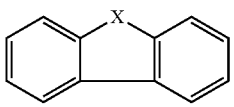

(2-2)

wherein X represents any one of —NR$^4$— where R$^4$ represents an aryl group which may have a substituent, —O—, and —S—; and the X-containing fused ring in formula (2-2) may have one or more substituents which may be bonded to each other to form a cyclic structure.

13. The monoamine compound according to claim 12, wherein the partial structure represented by formula (2-2) is a partial structure represented by formula (3):

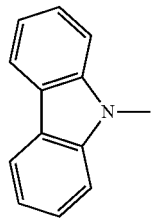

(3)

wherein the N-carbazole ring may further have one or more substituents, and the substituents may be bonded to each other to form a cyclic structure.

14. The monoamine compound according to claim 1, wherein in formula (1) at least one of $R^1$ to $R^3$ is a group represented by the following formula (11):

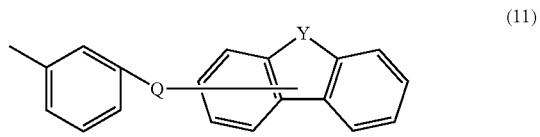

(11)

wherein Q represents a direct bond or a linking group; Y represents any one of —NR$^4$— where R$^4$ represents an aryl group which may have a substituent, —O—, and —S—; and the Y-containing fused ring in formula (11) may have one or more substituents which may be bonded to each other to form a cyclic structure.

15. The monoamine compound according to claim 1, which has a solubility in m-xylene of 5% by mass or more at 25° C. and atmospheric pressure.

16. The monoamine compound according to claim 1, wherein $R^1$ to $R^3$ each independently represent a phenyl group which may have as substituents one or more aromatic hydrocarbon groups or aromatic heterocyclic groups.

17. The monoamine compound according to claim 2, wherein $R^1$ to $R^3$ each independently represent a phenyl group which may have as substituents one or more aromatic hydrocarbon groups or aromatic heterocyclic groups.

18. The monoamine compound according to claim 3, wherein $R^1$ to $R^3$ each independently represent a phenyl group which may have as substituents one or more aromatic hydrocarbon groups or aromatic heterocyclic groups.

* * * * *